(12) United States Patent
Schroeder et al.

(10) Patent No.: US 7,326,549 B2
(45) Date of Patent: Feb. 5, 2008

(54) MYO-INOSITOL OXYGENASES

(75) Inventors: William A. Schroeder, Brooklyn Park, MN (US); Paula M. Hicks, Eden Prairie, MN (US); Sara C. McFarlan, St. Paul, MN (US); Timothy W. Abraham, Wayzata, MN (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 10/472,317

(22) PCT Filed: Mar. 19, 2002

(86) PCT No.: PCT/US02/08404

§ 371 (c)(1),
(2), (4) Date: Apr. 2, 2004

(87) PCT Pub. No.: WO02/074926

PCT Pub. Date: Sep. 26, 2002

(65) Prior Publication Data

US 2004/0185562 A1    Sep. 23, 2004

Related U.S. Application Data

(60) Provisional application No. 60/277,148, filed on Mar. 19, 2001.

(51) Int. Cl.
   *C12N 9/02*    (2006.01)
   *C12N 15/00*   (2006.01)
   *C12N 15/74*   (2006.01)
   *C12N 15/75*   (2006.01)
   *C12P 7/00*    (2006.01)
   *C12P 21/06*   (2006.01)
   *C12Q 21/06*   (2006.01)

(52) U.S. Cl. .................. 435/137; 435/25; 435/69.1; 435/132; 435/155; 435/455; 435/471; 435/483; 435/488

(58) Field of Classification Search .......... 435/320.1, 435/325, 252.3, 254.11, 254.2, 183, 91.1, 435/455, 471
See application file for complete search history.

(56) References Cited

U.S. PATENT DOCUMENTS

| 3,410,929 | A | 11/1968 | Ledding et al. |
|---|---|---|---|
| 4,259,443 | A | 3/1981 | Danehy |
| 4,337,202 | A | 6/1982 | Hearon et al. |
| 4,668,813 | A | 5/1987 | Ogawa et al. |
| 4,683,195 | A | 7/1987 | Mullis et al. |
| 4,965,197 | A | 10/1990 | Liebl et al. |
| 5,034,323 | A | 7/1991 | Jorgensen et al. |
| 5,250,428 | A | 10/1993 | Hoshino et al. |
| 5,268,526 | A | 12/1993 | Hershey et al. |
| 5,296,364 | A | 3/1994 | Agrawal |
| 5,510,471 | A | 4/1996 | Lebrun et al. |
| 5,529,912 | A | 6/1996 | Henry et al. |
| 5,538,880 | A | 7/1996 | Lundquist et al. |
| 5,538,885 | A | 7/1996 | Hollis et al. |
| 5,571,706 | A | 11/1996 | Baker et al. |
| 5,589,615 | A | 12/1996 | De Clercq et al. |
| 5,597,945 | A | 1/1997 | Jaynes et al. |
| 5,599,701 | A | 2/1997 | Henry et al. |
| 5,610,042 | A | 3/1997 | Chang et al. |
| 5,677,175 | A | 10/1997 | Hodges et al. |
| 5,736,369 | A | 4/1998 | Bowen et al. |
| 5,750,386 | A | 5/1998 | Conkling et al. |
| 5,750,871 | A | 5/1998 | Moloney et al. |
| 5,773,269 | A | 6/1998 | Somers et al. |
| 5,780,708 | A | 7/1998 | Lundquist et al. |
| 5,817,870 | A | 10/1998 | Haas et al. |
| 5,830,716 | A | 11/1998 | Kojima et al. |
| 5,830,732 | A | 11/1998 | Mochizuki et al. |
| 5,830,733 | A | 11/1998 | Nevalainen et al. |
| 5,840,561 | A | 11/1998 | Mochizuki et al. |
| 6,037,480 | A | 3/2000 | Eyal et al. |
| 6,169,187 | B1 | 1/2001 | Eyal |
| 6,251,626 | B1 | 6/2001 | Stougaard et al. |
| 6,630,330 | B1 | 10/2003 | Porro et al. |

OTHER PUBLICATIONS

Chotani et al., The commercial production of chemicals using pathway engineering. Biochimica et Biophysica Acta 1543: 434-455, 2000.*
Reddy et al., myo-Inositol Oxygenae from Hog Kidney. JBC., 256 (16): 8510-8518, 1981.*
Arner et al., myo-Inositol oxygenase: molecular cloning and expressionof a unique enzyme that oxidizes myo-inositol and D-chiro-inositol. Biochem. J. 360: 313-320, 2001.*
Molina et al., Inositol synthesis and catabolism in *Cryptococcus neoformans*. Yeast 15: 1657-1667, 1999.*
Chotani et al., The commercial productionof chemicals using pathway engineering. Biochi. et Biophysica Acta 1543: 434-455, 2000.*
GenBank Accession No. AAB49376, Oct. 25, 2000.
GenBank Accession No. AF298179, Oct. 2, 2000.
GenBank Accession No. AI277890, Jan. 29, 1999.
GenBank Accession No. AJ010734, Sep. 7, 1998.
GenBank Accession No. BAA23804, Dec. 10, 1997.
GenBank Accession No. BAA34218, Nov. 27, 1999.
GenBank Accession No. D90352, Dec. 17, 2002.
GenBank Accession No. D90353, Dec. 17, 2002.
GenBank Accession No. J04453, May 11, 1995.

(Continued)

*Primary Examiner*—Rebecca E. Prouty
*Assistant Examiner*—Ganapathirama Raghu
(74) *Attorney, Agent, or Firm*—Klarquist Sparkman, LLP

(57) ABSTRACT

The invention provides methods and materials related to the production of organic products such as glucuronic acid, ascorbic acid, and glucaric acid. Specifically, the invention provides cells, methods for culturing cells, isolated nucleic acid molecules, and methods and materials for producing various organic products such as glucuronic acid, ascorbic acid, and glucaric acid.

26 Claims, 23 Drawing Sheets

OTHER PUBLICATIONS

GenBank Accession No. L14019, Jan. 5, 1994.
GenBank Accession No. M58708, Apr. 4, 2002.
GenBank Accession No. NM_001072, Mar. 30, 2004.
GenBank Accession No. NM_005536, Dec. 21, 2003.
GenBank Accession No. NP_403959, Jun. 4, 2004.
GenBank Accession No. NP_518171, Jun. 4, 2004.
GenBank Accession No. P07102, Jun. 15, 2004.
GenBank Accession No. P10867, Jun. 15, 2004.
GenBank Accession No. S53050, Jul. 23, 1999.
GenBank Accession No. U07993, Jul. 22, 1994.
GenBank Accession No. X67189, Jun. 30, 1993.
GenBank Accession No. X72016, Mar. 15, 1994.
GenBank Accession No. X99626, Oct. 11, 1996.
Adams et al., *Methods in Yeast Genetics*, 1997, Cold Spring Harbor Laboratory Press, (TOC only).
Ainley et al., "Regulatable endogenous production of cytokinins up to 'toxic' levels in transgenic plants and plant tissues," *Plant Molecular Biology*, 1993, 22:13-23.
An et al., "Organ-Specific and Developmental Regulation of the Nopaline Synthase Promoter in Transgenic Tobacco Plants," *Plant Physiol.*, 1988, 88:547-552.
Arner, "Myo-Inositol Oxygenase: Molecular Enzymology and Tissue Specific Expression," 2002, Graduate Thesis, The Pennsylvania State University.
Becker et al., "High-Efficiency Transformation of Yeast by Electroporation," *Methods in Enzymology*, 1991, 194:182-187.
Benfey et al., "The Cauliflower Mosaic Virus 35S Promoter: Combinatorial Regulation of Transcription in Plants," *Science*, 1990, 250:959-966.
Bett et al., "An efficient and flexible system for construction of adenovirus vectors with insertions or deletions in early regions 1 and 3," *Proc. Natl. Acad. Sci. USA*, 1994, 91:8802-8806.
Bradford, "A Rapid and Sensitive Method for the Quantitation of Microgram Quantities of Protein Utilizing the Principle of Protein-Dye Binding," *Analytical Biochemistry*, 1976, 72:248-254.
Burritt et al., "Filamentous Phage Display of Oligopeptide Libraries," *Analytical Biochemistry*, 1996, 238:1-13.
Bustos et al., "Regulation of β-Glucuronidase Expression in Transgenic Tobacco Plants by an A/T-Rich, cis-Acting Sequence Found Upstream of a French Bean β-Phaseolin Gene," *The Plant Cell*, 1989, 1:839-853.
Rosario, "*Cryptococcus neoformans*' inositol catabolic gene and protein," 1998, Thesis, California State University.
Callis et al., "Heat Inducible Expression of a Chimeric Maize hsp70CAT Gene in Maize Protoplasts," *Plant Physiol.*, 1988, 88:965-968.
Carpenter et al., "Preferential Expression of an α-Tubulin Gene of Arabidopsis in Pollen," *The Plant Cell*, 1992, 4:557-571.
Caruso et al., "Adenovirus-mediated interleukin-12 gene therapy for metastatic colon carcinoma," *Proc. Natl. Acad. Sci. USA*, 1996, 93:11302-11306.
Charalampous et al., "Biochemical Studies on Inositol; Conversion of Inositol to Glucuronic Acid by Rat Kidney Extracts," *J. Biol. Chem.*, 1957, 228:1-13.
Chittum et al., "Rabbit β-Globin Is Extended Beyond Its UGA Stop Codon by Multiple Suppressions and Translational Reading Gaps," *Biochemistry*, 1998, 37:10866-10870.
Cosgrove, "Inositol Hexakisphosphates," *Inositol Phosphates Their Chemistry, Biochemistry and Physiology*, 1980, Chapter 4, pp. 26-43 Elsevier Scientific Publishing Company.
Crawford et al., "Synthesis of ι-Ascorbic Acid," *Advances in Carbohydrate Chemistry and Biochemistry*, 1980, 37:79-155.
Dekeyser et al., "Transient Gene Expression in Intact and Organized Rice Tissues," *The Plant Cell*, 1990, 2:591-602.
Del Poeta et al., "*Cryptococcus neoformans* Differential Gene Expression Detected In Vitro and In Vivo with Green Fluorescent Protein," *Infection and Immunity*, 1999, 67:1812-1820.
Denis et al., "Expression of Engineered Nuclear Male Sterility in *Brassica napus*," *Plant Physiol.*, 1993, 101:1295-1304.

Ausubel et al. (eds.), "Cell Disruption Using Glass Beads," *Current Protocols in Molecular Biology*, vol. 2, 1999, Supplement 12, Section 13.13.4, John Wiley & Sons, Inc.
Eng et al., "An Approach to Correlate Tandem Mass Spectral Data of Peptides with Amino Acid Sequences in a Protein Database," *J. Am. Soc. Mass Spectrom.*, 1994, 5:976-989.
Fang et al., "Gene therapy for phenylketonuria: phenotypic correction in a genetically deficient mouse model by adenovirus-mediated hepatic gene transfer," *Gene Therapy*, 1994, 1:247-254.
Fromm et al., "An Octopine Synthase Enhancer Element Directs Tissue-Specific Expression and Binds ASF-1, a Factor from Tobacco Nuclear Extracts," *The Plant Cell*, 1989, 1:977-984.
Gatz, "Chemical Control of Gene Expression," *Annu. Rev. Plant Physiol. Plant Mol. Biol.*, 1997, 48:89-108.
Gilmartin et al., "Characterization of a Gene Encoding a DNA Binding Protein with Specificity for a Light-Responsive Element," *The Plant Cell*, 1992, 4:839-849.
Horton et al., "Conformations of the $_D$-Glucarolactones and $_D$-Glucaric Acid in Solution," *Carbohydrate Research*, 1982, 105:95-109.
Hu et al., "Identification of a novel kidney-specific gene downregulated in acute ischemic renal failure," *Am. J. Physiol. Renal Physiol.*, 2000, 279:F426-F439.
Ito et al., "Transformation of Intact Yeast Cells Treated with Alkali Cations," *J. Bacteriol.*, 1983, 153:163-168.
Keegstra et al., "Isolation and Characterization of Chloroplast Envelope Membranes," Methods for Plant Molecular Biology, 1988, 5:173-182.
Keil et al., "Primary structure of a proteinase inhibitor II gene from potato (*Solanum tuberosum*)," *Nucleic Acids Research*, 1986, 14:5641-5650.
Kiers et al., "Regulation of Alcoholic Fermentation in Batch and Chemostat Cultures of *Kluyveromyces lactis* CBS 2359," *Yeast*, 1998, 14:459-469.
Kobayashi et al., "Lactone-ring-cleaving enzyme: Genetic analysis, novel RNA editing, and evolutionary implications," *Proc. Natl. Acad. Sci. USA*, 1998, 95:12787-12792.
Koller and Koller, "Affinity Chromatography of *Myo*-Inositol Oxygenase From Rat Kidney by Means of an Insoluble $_D$-*Galacto*-Hexodialdose Derivative," *J. Chromatography*, 1984, 283:191-197.
Koller and Koller, "*myo*-Inositol oxygenase from rat kidneys; Substrate-dependent oligomerization," *Eur. J. Biochem.*, 1990, 193:421-427.
Koller and Koller, "*myo*-Inositol Oxygenase from Rat Kidneys; Purification by Affinity Chromatography; Physical and Catalytic Properties," *Hoppe-Seyler's Z. Physiol. Chem.*, 1979, 360:507-513.
Kuhlemeier et al., "The Pea *rbcS-3A* Promoter Mediates Light Responsiveness but not Organ Specificity," *The Plant Cell*, 1989, 1:471-478.
Laemmli, "Cleavage of Structural Proteins during the Assembly of the Head of Bacteriophage T4," *Nature*, 1970, 227:680-685.
Logemann et al., Expression of a Barley Ribosome-Inactivating Protein Leads to Increased Fungal Protection in Transgenic Tobacco Plants, *Bio/Technology*, 1992, 10:305-308.
Lykkesfeldt, "Determination of Ascorbic Acid and Dehydroascorbic Acid in Biological Samples by High-Performance Liquid Chromatography Using Subtraction Methods: Reliable Reduction with Tris[2-carboxyethyl]phosphine Hydrochloride," *Analytical Biochemistry*, 2000, 282:89-93.
Naber et al., "Concerning the mechanism for transfer of $_D$-glucuronate from *myo*-inositol oxygenase to $_D$-glucuronate reductase," *Biochimica et Biophysica Acta*, 1987, 911:365-368.
Naber et al., "$_L$-*myo*-Inosose-1 as a Probable Intermediate in the Reaction Catalyzed by *myo*-Inositol Oxygenase," *Biochemistry*, 1986, 25:7201-7207.
Napoli et al., "Introduction of a Chimeric Chalcone Synthase Gene into Petunia Results in Reversible Co-Suppression of Homologous Genes in trans," *The Plant Cell*, 1990, 2:279-289.
Nelson et al., *Myo*-Inositol-Dependent Sodium Uptake in Ice Plant, *Plant Physiol.*, 1999, 119:165-172.
Nelson et al., "Regulation of Cell-Specific Inositol Metabolism and Transport in Plant Salinity Tolerance," *Plant Cell*, 1998, 10:753-764.

Nishikimi, L-Gulono-γ-lactone Oxidase (Rat and Goat Liver), *Methods in Enzymology*, 1979, 62:24-30.

Nissen et al., "Expression of a cytoplasmic transhydrogenase in *Saccharomyces cerevisiae* results in formation of 2-oxoglutarate due to depletion of the NADPH pool," *Yeast*, 2001, 18:19-32.

O'Farrell, "High Resolution Two-Dimensional Electrophoresis of Proteins," *J. Biol. Chem.*, 1975, 250:4007-4021.

Odell et al., "Identification of DNA sequences required for activity of the cauliflower mosaic virus 35S promoter," *Nature*, 1985, 313:810-812.

Opperman et al., "Root-Knot Nematode-Directed Expression of a Plant Root-Specific Gene," *Science*, 1994, 263:221-223.

Pouwels et al., *Cloning Vectors A Laboratory Manual*, 1985, Elsevier Science Publishers B.V., (TOC only).

Reddy et al., "*myo*-Inositol Oxygenase from Hog Kidney; Purification and Characterization of the Oxygenase and of an Enzyme Complex Containing the Oxygenase and D-Glucuronate Reductase," *J. Biol. Chem.*, 1981, 256:8510-8518.

Rosahl et al., "Expression of a tuber-specific storage protein in foreign plants: demonstration of an esterase activity," *Embo J.*, 1987, 6:1155-1159.

Sambrook et al., *Molecular Cloning*, 2nd edition, 1989, Cold Spring Harbor Laboratory Press, Sections 7.39-7.52.

Schäffner et al., "Maize *rbcS* Promoter Activity Depends on Sequence Elements Not Found in Dicot *rbcS* Promoters," *The Plant Cell*, 1991, 3:997-1012.

Schernthaner et al., "Endosperm-specific activity of a zein gene promoter in transgenic tobacco plants," *EMBO J.*, 1988, 7:1249-1255.

Shimizu et al., "Purification and characterization of a novel lactonohydrolase, catalyzing the hydrolysis of aldonate lactones and aromatic lactones, from *Fusarium oxysporum*," *Eur. J. Biochem.*, 1992, 209:383-390.

Stockhaus et al., "The Promoter of the Gene Encoding the $C_4$ Form of Phosphoenolpyruvate Carboxylase Directs Mesophyll-Specific Expression in Transgenic $C_4$ *Flaveria* spp," *The Plant Cell*, 1997, 9:479-489.

Sullivan and Clarke, "A Highly Specific Procedure for Ascorbic Acid," *J. Assoc. Offic. Agr. Chemists*, 1955, 38:514-518.

Sullivan et al., "Purification and Characterization of Hexose Oxidase from the Red Alga *Chondrus Crispus*," *Biochimica et Biophysica Acta*, 1973, 309:11-22.

Terada et al., "Expression of CaMV35S-GUS gene in transgenic rice plants," *Mol. Gen. Genet.*, 1990, 220:389-392.

Toffaletti et al., "Gene Transfer in *Cryptococcus neoformans* by Use of Biolistic Delivery of DNA," *J. Bacteriol.*, 1993, 175:1405-1411.

Wiese et al., "Structural organization and differential expression of three stilbene synthase genes located on a 13 kb grapevine DNA fragment," *Plant Molecular Biology*, 1994, 26:667-677.

Wheeler et al., "The biosynthetic pathway of vitamin C in higher plants," *Nature*, 1998, 393:365-369.

Yamamoto et al., "Characterization of *cis*-Acting Sequences Regulating Root-Specific Gene Expression in Tobacco," *The Plant Cell*, 1991, 3:371-382.

Yang et al., "Identification of a renal-specific oxido-reductase in newborn diabetic mice," *Proc. Natl. Acad. Sci. USA*, 2000, 97:9896-9901.

Yoshida et al., "Temporal and Spatial Patterns of Accumulation of the Transcript of *Myo*-Inositol-1-Phosphate Synthase and Phytin-Containing Particles during Seed Development in Rice," *Plant Physiol.*, 1999, 119:65-72.

Zannoni et al., "A Rapid Micromethod for the Determination of Ascorbic Acid in Plasma and Tissues," *Biochemical Medicine*, 1974, 11:41-48.

Arner, R. J., "Cloning, expression, and characterization of myo-inositol oxygenase from hog kidney." FASEB Journal, 2001, 15:4, A535, abstract #44.27.

Arner, R. J., "*myo*-Inositol oxygenase: molecular cloning and expression of a unique enzyme that oxidizes *myo*-inositol and D-*chiro*-inositol," *Biochem J.*, 2001, 360:2, 313-20.

Molina et al., "Inositol Synthesis and Catabolism in *Cryptococcus neoformans*," *Yeast*, 1999, 15:1657-1667.

Rosario et al., "Inositol Oxygenase from *Cryptococcus neoformans*: Purification and Cloning," *Abstracts of the General Meeting of the American Society for Microbiology*, 1998, 98:267, Abstract No. F-85.

Gallezot et al., "Catalytic Oxidations with Air for Clean and Selective Transformations of Polyols," *Chem. Ind.*, 1995, 62:331-340.

* cited by examiner

FIG. 7A

```
                      10         20         30         40
                       *          *          *          *
SEQ ID NO:19  MHAPEVNDYIKHKAVKLDQVSDEIDEVNVLKLKQKDAVEKTQA-EIDYDL
SEQ ID NO:20  MNISVENPVFVHE----DSTTQKTGE---LRLDSDIPMSKISS-DDEVFL
SEQ ID NO:21  --------------------------------------------------
SEQ ID NO:22  -MSQILQNFIKQA---------QYNPLHSLEEWEEDLLNRYP------DP
SEQ ID NO:23  MTISVEKPIFEEEVSAFEKSGDNIGE---LKLDGGFSMPKMDT-NDDEAF
SEQ ID NO:24  --------------------------------------------------
SEQ ID NO:25  --------------------------------------------------
SEQ ID NO:26  -------------------------MKVTV----GPDPSLVYRP-DVDPEV
SEQ ID NO:27  ----------------MKVD--------------VGPDPSLVYRP-DVDPEV
SEQ ID NO:28  --------------------------------------------------
SEQ ID NO:29  ----------------MKVD--------------VGPDPSLVYRP-DVDPEM
SEQ ID NO:30  -----------------------------TQGPDPSLVYRP-DVDPEV
SEQ ID NO:31  -------------------------MKVTV----GPDPSLVYRP-DVDPEV
SEQ ID NO:32  -------------------------MKVTV----GPDPSLVYRP-DVDPEV
SEQ ID NO:33  ----------------MKVD--------------LGPDPSLVYRP-DVDPEM
SEQ ID NO:34  -------------MTILIDRHSDQNGDEIVEKNQGNGKEEETEL-VLDAGF
SEQ ID NO:35  ---MQVSRLL--TPTLLVAPSGRYIHIRDCKIKSLIFIYLCCCHERDYDA 60         70         80
                       *          *          *
SEQ ID NO:19  ASKFDQEKDKAAFRQYEEA--C-DR-------VKNFYAEQHLKQTYEYNV
SEQ ID NO:20  APEMN------AFGRQFRDY--T-DTNSERQKSVEHFYATQHTNQTLDFVQ
SEQ ID NO:21  --------------------------------------------------
SEQ ID NO:22  HSIVKEGKTTQEYRNYETP--TRET-------VKEFYRLNHINQTYNFVL
SEQ ID NO:23  LAP-EMNAFGRQFRDYDVE--S-ERQKG----VEEFYRLQHINQTVDFVK
SEQ ID NO:24  ------------------------------------MQHIHQTYDFVK
SEQ ID NO:25  --------------------------------------------------
SEQ ID NO:26  A------KDKASFRNYTSGPLL-DR-------VFTTYKLMHTHQTVDFVR
SEQ ID NO:27  A------KDKASFRNYTSGPLL-DR-------VFTTYKLMHTHQTVDFVR
SEQ ID NO:28  ------------------------------------MQHIHQTYDFVK
SEQ ID NO:29  A------KSKDSFRNYTSGPLL-DR-------VFTTYKLMHTHQTVDFVS
SEQ ID NO:30  A------KDKASFRNYTSGPLL-DR-------VFTTYKLMHTHQTVDFVR
SEQ ID NO:31  A------KDKASFRNYTSGPLL-DR-------VFTTYKLMHTHQTVDFVR
SEQ ID NO:32  A------KDKASFRNYTSGPLL-DR-------VFTTYKLMHTHQTVDFVR
SEQ ID NO:33  A------KSKGSFRNYTSGPLL-DR-------VFTTYKLMHTHQTVDFVM
SEQ ID NO:34  EAPHTNSFGR-TFRDYDAE--S-ERRRG----VEEFYRVNHIGQTVDFVR
SEQ ID NO:35  ES--------------ER--R-RG-------VEEFYRVNHIGQTVDFVR 100        110        120        130
                       *          *          *          *
SEQ ID NO:19  KIRQEFRNTVRARMSIWEAMELLDNLVDESDPDTSVGQIEHLLQTAEAIR
SEQ ID NO:20  KMRSEYGKLDKMVMNIWECCELSKEVVDESDPDLDEPQIQHLLQSAEAIR
SEQ ID NO:21  ----------------MTIWEAMEKLNTLIDNSDPDTELSQIQHLLQTAEAMR
SEQ ID NO:22  EKEKNFLKFDKKEMSVWDAVEFLNQLVDDSDPDTEMDQLQHLLQTSEAIR
SEQ ID NO:23  KMRAEYGKLDKMVMSIWECCELLNEVVDESDPDLDEPQIQHLLQSAEAIR
SEQ ID NO:24  KMRKEYGKLNKMEMSIWECCELLNNVVDESDPDLDEPQIQHLLQTAEAIR
SEQ ID NO:25  ---------------MSIWESCELLNEFVDESDPDLDEPQIEHLIQTAEAIR
SEQ ID NO:26  SKHAQFGGFSYKKMTVMEAVDLLDGLVDESDPDVDFPNSFHAFQTAEGIR
SEQ ID NO:27  SKHAQFGGFSYKKMTVMEAVDLLDGLVDESDPDVDFPNSFHAFQTAEGIR
SEQ ID NO:28  KMRKEYGKLNKMEMSIWECCELLNNVVDESDPDLDEPQIQHLLQTAEAIR
SEQ ID NO:29  RKRIQYGGFSYKKMTIMEAVGMLDDLVDESDPDVDFPNSFHAFQTAEGIR
SEQ ID NO:30  SKHAQFGGFSYKKMTVMEAVDLLDGLVDESDPDVDFPNSFHAFQTAEGIR
SEQ ID NO:31  SKHAQFGGFSYKKMTVMEAVDLLDGLVDESDPDVDFPNSFHAFQTAEGIR
```

FIG. 7B

```
SEQ ID NO:32  SKHAQFGSFSYKKMTVMEAVDMLDDLVDESDPDVDFPNSFHAFQTAEGIR
SEQ ID NO:33  RKRIQFGSFSYKKMTVMEAVDMLDDLVDESDPDVDFPNSFHAFQTAEGIR
SEQ ID NO:34  KMREEYEKLNRTEMSIWECCELLNEFIDESDPDLDEPQIEHLLQTAEAIR
SEQ ID NO:35  KMREEYEKLNRTEMSIWECCELLNEFIDESDPDLDEPQIEHLLQTAEAIR 150       160       170       180
                          *         *         *         *
SEQ ID NO:19  R-D-GKPE-WMQVTGLIHDLGKLLCF--FGADGQWDVVGDTFVVGCKFSD
SEQ ID NO:20  K-D-YPNEDWLHLTALIHDLGKVLTLPQFGGLPQWAVVGDTFPVGCAFDE
SEQ ID NO:21  R-D-GKPR-WMQLTGLIHDLGKLLFF--YGAEGQWDVVGDTFPVGCAFDN
SEQ ID NO:22  A-D-GHPD-WMVLTGFFHDMGKVLCL--FG-EPQWATVGDTYPVGCAFSD
SEQ ID NO:23  K-D-YPNEDWLHLTALIHDLGKVITLPQFGGLPQWAVVGDTFPVGCAFDE
SEQ ID NO:24  R-D-YPDEDWLHLTALIHDLGKVLLLPEFGGLPQWAVVGDTFPVGCTFDS
SEQ ID NO:25  K-DYPNEE-WLHLTGLIHDLGKVLLHPDFGSEPQWAVVGDTFPLGCAFSE
SEQ ID NO:26  KAH-PDKD-WFHLVGLLHDLGKVLAL--FG-EPQWAVVGDTFPVGCRPQA
SEQ ID NO:27  KAH-PDKD-WFHLVGLLHDLGKVLAL--FG-EPQWAVVGDTFPVGCRPQA
SEQ ID NO:28  R-D-YPDEDWLHLTALIHDLGKVLLLPEFGGLPQWAVVGDTFPVGCTFDS
SEQ ID NO:29  KAH-PDKD-WFHLVGLLHDLGKIMAL--WG-EPQWAVVGDTFPVGCRPQA
SEQ ID NO:30  KAH-PDKD-WFHLVGLLHDLGKVLAL--FG-EPQWAVVGDTFPVGCRPQA
SEQ ID NO:31  KAH-PDKD-WFHLVGLLHDLGKVLAL--FG-EPQWAVVGDTFPVGCRPQA
SEQ ID NO:32  KAH-PDKD-WFHLVGLLHDLGKILAL--WG-EPQWAVVGDTFPVGCRPQA
SEQ ID NO:33  KAH-PDKD-WFHLVGLLHDLGKILAL--WG-EPQWAVVGDTFPVGCRPQA
SEQ ID NO:34  K-D-YPDEDWLHLTGLIHDLGKVLLHSSFGELPQWAVVGDTFPVGCAFDE
SEQ ID NO:35  K-D-YPDEDWLHLTGLIHDLGKVLLHSSFGELPQWAVVGDTFPVGCAFDE 190       200       210       220       230
                          *         *         *         *         *
SEQ ID NO:19  KIIYPD-T---FKSNPDYNNPKLNTKYGVYEPNCGLDNVLLSWGHDEYMY
SEQ ID NO:20  SNVHHK-Y---FMENPDFNNPKYNTKAGIYSEGCGLENVLMSWGHDDYMY
SEQ ID NO:21  RIVLPT-T---FEGNPDIHHPVYSTKHGIYKPGCGIENLMISWGHDEYMY
SEQ ID NO:22  KIVFSE-F---FQENPDYNNPNYNTKYGIYEPNCGLINVHISWGHDEYFY
SEQ ID NO:23  SNVHHK-Y---FVENPDFHNETYNTKNGIYSEGCGLNNVMMSWGHDDYMY
SEQ ID NO:24  ANIHHK-Y---FKGNHDINNPKYNTKNGVYTEGCGLDNVLMSWGHDDYMY
SEQ ID NO:25  TIVHHE-F---FKDNPDFHNPKYNTKYGVYSEKCGLDNVLMSWGHDEYMY
SEQ ID NO:26  SVVFCDST---FQDNPDLQDPRYSTELGMYQPHCGLDRVLMSWGHDEYMY
SEQ ID NO:27  SVVFCDST---FQDNPDLQDPRYSTELGMYQPHCGLDRVLMSWGHDEYMY
SEQ ID NO:28  ANIHHK-Y---FKGNHDINNPKYNTKNGVYTEGCGLDNVLMSWGHDDYMY
SEQ ID NO:29  SVVFCDST---FQDNPDLQDPRYSTELGMYQPHCGLENVLMSWGHDEYLY
SEQ ID NO:30  SVVFCDST---FQDNPDLQDPRYSTELGMYQPHCGLDRVLMSWGHDEYMY
SEQ ID NO:31  SVVFCDST---FQDNPDLQDPRYSTELGMYQPHCGLDRVLMSWGHDEYMF
SEQ ID NO:32  SVVFCDST---FQDNPDLQDPRYSTELGMYQPHCGLENVLMSWGHDEYLY
SEQ ID NO:33  SVVFCDST---FQDNPDLQDPRYSTELGMYQPHCGLENVLMSWGHDEYLY
SEQ ID NO:34  SIVHHK-Y---FKENPDYDNPSYNSKYGIYTEGCGLDNVLMSWGHDDYMY
SEQ ID NO:35  SIVHHK-VHKYFKENPDYDNPSYNSKYGIYTEGCGLDNVLMSWGHDDYMY 240       250       260
                               *         *         *
SEQ ID NO:19  EIC---------------K-NQSTLPQEALAMIRYHSFYPWHREGAYEH
SEQ ID NO:20  LVA---------------KENGSTLPSPGLFIIRYHSFYPLHKAGAYTH
SEQ ID NO:21  TVC---------------K-EQSKLPREALAMIRYHSFYPWHREGAYRE
SEQ ID NO:22  QMM---------------K-NY--LPEPALYMLRYHSFYPQHRENAYKH
SEQ ID NO:23  LVA---------------KENGSTLPSAGQFIIRYHSFYPLHTAGEYTH
SEQ ID NO:24  LVA---------------KKNGTTLPHAGLFIIRYHSFYPLHKAGAYTH
SEQ ID NO:25  LVA---------------KMNNTTLPPAALFIIRFHSFYPLHREGAYMH
SEQ ID NO:26  QVM---------------KFNKFSLPPEAFYMIRFHSFYPWHTGRDYQQ
SEQ ID NO:27  QVM---------------KFNKFSLPPEAFYMIRFHSFYPWHTGRDYQQ
SEQ ID NO:28  LVA---------------KKNGTTLPHAGLFIIRYHSFYPLHKAGAYTH
```

FIG. 7C

```
SEQ ID NO:26  ------------------------------L-SW------------------
SEQ ID NO:27  ------------------------------L-SW------------------
SEQ ID NO:28  ------------------------------T-KMVR----------------
SEQ ID NO:29  ------------------------------L-SW------------------
SEQ ID NO:30  ------------------------------L-SW------------------
SEQ ID NO:31  ------------------------------L-SW------------------
SEQ ID NO:32  ------------------------------L-SW------------------
SEQ ID NO:33  ------------------------------L-SW------------------
SEQ ID NO:34  MIELDGGSLIEKSLTILLHQKETPWYLV-DWLSFGWKAKIVEMLGEATGI
SEQ ID NO:35  MIELDGGSLIEKSLTILLHQKETPWYLV-DWLSFGWKAKIVEMLGEATGI

SEQ ID NO:19  --------------------------------------------------
SEQ ID NO:20  --------------------------------------------------
SEQ ID NO:21  --------------------------------------------------
SEQ ID NO:22  --------------------------------------------------
SEQ ID NO:23  --------------------------------------------------
SEQ ID NO:24  --------------------------------------------------
SEQ ID NO:25  --------------------------------------------------
SEQ ID NO:26  --------------------------------------------------
SEQ ID NO:27  --------------------------------------------------
SEQ ID NO:28  --------------------------------------------------
SEQ ID NO:29  --------------------------------------------------
SEQ ID NO:30  --------------------------------------------------
SEQ ID NO:31  --------------------------------------------------
SEQ ID NO:32  --------------------------------------------------
SEQ ID NO:33  --------------------------------------------------
SEQ ID NO:34  LASVDGRRRPLRYGLR----------------------
SEQ ID NO:35  LASISDDDLHNQLWASGGWTEKTTALWASLISNWAFS
```

Figure 9

MTASSVLLHTGQKMPLIGLGTWKSEPGQVKAAIKYALSVGYRHIDCASVYGNET
EIGEALKESVGAGKAVPREELFVTSKLWNTKHHPEDVEPAVRKTLADLQLEYLD
LYLMHWPYAFERGDNPFPKNADGTVKYDSTHYKETWKALEALVAKGLVKALG
LSNFSSRQIDDVLSVASVRPAVLQVECHPYLAQNELIAHCQARGLEVTAYSPLGS
SDRAWRHPDEPVLLEEPVVLALAEKHGRSPAQILLRWQVQRKVICIPKSITPSRIL
QNIQVFDFTFSPEEMKQLDALNKNWRYIVPMITVDGKRVPRDAGHPLYPFNDPY
(SEQ ID NO:36)

Figure 10

MTTGRMSRRECLSAAVMVPIAAMTATATITGSAEAAKNNMNGSTIGKITKFSPRL
DAILDVSTPIEVIASDIQWSEGPVWVKNGNFLLFSDPPANIMRKWTPDAGVSIFLK
PSGHAEPIPAGQFREPGSNGMKVGPDGKIWVADSGTRAIMKVDPVTRQRSVVDN
YKGKRFNSPNDLFFSKSGAVYFTDPPYGLTNLDESDIKEMNYNGVFRLSPDGRLD
LIEAGLSRPNGLALSPDETKLYVSNSDRASPNIWVYSLDSNGLPTSRTLLRNFRKE
YFDQGLAGLPDGMNIDKQGNLFASAPGGIYIFAPDGECLGLIFW (SEQ ID NO:37)

Figure 11

MPSSISVLAGVLVPVLGAVAAKLPSTAQIIDQKSFNVLKDVPPPAVANDSLVFTW
PGVTEESLVEKPFHVYDEEFYDVIGKDPSLTLIATSDTDPIFHEAVVWYPPTEEVFF
VQNAGAPAAGTGLNKSSIIQKISLKEADAVRKGKQDEVKVTVVDSNPQVINPNG
GTYYKGNIIFAGEGQGDDVPSALYLMNPLPPYNTTTLLNNYFGRQFNSLNDVGIN
PRNGDLYFTDTLGYLQDFRPVPGLRNQVYRYNFDTGAVTVVADDFTLPNGIGF
GPDGKKVYVTDTGIALGFYGRNLSSPASVYSFDVNQDGTLQNRKTFAYVASFIPD
GVHTDSKGRVYAGCGDGVHVWNPSGKLIGKIYTGTVAANFQFAGKGRMIITGQ
TKLFYVTLGASGPKLYD (SEQ ID NO:38)

Figure 12

MVHGYKGVQFQNWAKTYGCSPEVYYQPTSVEEVREVLALAREQKKKVKVVGG
GHSPSDIACTDGFMIHMGKMNRVLQVDKEKKQITVEAGILLADLHPQLDEHGLA
MSNLGAVSDVTVAGVIGSGTHNTGIKHGILATQVVALTLMTADGEVLECSESRN
ADVFQAARVHLGCLGIILTVTLQCVPQFQLQETSFPSTLKEVLDNLDSHLKRSEYF
RFLWFPHTENVSIIYQDHTNKAPSSASNWFWDYAIGFYLLEFLLWTSTYLPCLVG
WINRFFFWMLFNCKKESSNLSHKIFTYECRFKQHVQDWAIPREKTKEALLELKA
MLEAHPKVVAHYPVEVRFTRGDDILLSPCFQRDSCYMNIIMYRPYGKDVPRLDY
WLAYETIMKKFGGRPHWAKAHNCTQKDFEEMYPTFHKFCDIREKLDPTGMFLN
SYLEKVFY (SEQ ID NO:39)

Figure 13

MSTIPFRKNYVFKNWAGIYSAKPERYFQPSSIDEVVELVKSARLAEKSLVTVGSG
HSPSNMCVTDEWLVNLDRLDKVQKFVEYPELHYADVTVDAGMRLYQLNEFLG
AKGYSIQNLGSISEQSVAGIISTGSHGSSPYHGLISSQYVNLTIVNGKGELKFLDAE
NDPEVFKAALLSVGKIGIIVSATIRVVPGFNIKSTQEVITFENLLKQWDTLWTSSEF
IRVWWYPYTRKCVLWRGNKTTDAQNGPAKSWWGTKLGRFFYETLLWISTKIYA
PLTPFVEKFVFNRQYGKLEKSSTGDVNVTDSISGFNMDCLFSQFVDEWGCPMDN
GLEVLRSLDHSIAQAAINKEFYVHVPMEVRCSNTTLPSEPLDTSKRTNTSPGPVYG
NVCRPFLDNTPSHCRFAPLENVTNSQLTLYINPTIYRPFGCNTPIHKWFTLFENTM
MVAGGKPHWAKNFLGSTTLAAGPVKKDTDYDDFEMRGMALKVEEWYGEDLK
KFRKIRKEQDPDNVFLANKQWAIINGIIDPSELSD (SEQ ID NO:40)

Figure 14

MKAILIPFLSLLIPLTPQSAFAQSEPELKLESVVIVSRHGVRAPTKATQLMQDVTPD
AWPTWPVKLGWLTPRGGELIAYLGHYQRQRLVADGLLAKKGCPQSGQVAIIAD
VDERTRKTGEAFAAGLAPDCAITVHTQADTSSPDPLFNPLKTGVCQLDNANVTD
AILSRAGGSIADFTGHRQTAFRELERVLNFPQSNLCLKREKQDESCSLTQALPSEL
KVSADNVSLTGAVSLASMLTEIFLLQQAQGMPEPGWGRITDSHQWNTLLSLHNA
QFYLLQRTPEVARSRATPLLDLIKTALTPHPPQKQAYGVTLPTSVLFIAGHDTNLA
NLGGALELNWTLPGQPDNTPPGGELVFERWRRLSDNSQWIQVSLVFQTLQQMR
DKTPLSLNTPPGEVKLTLAGCEERNAQGMCSLAGFTQIVNEARIPACSL (SEQ ID
NO:41)

Figure 15

LSDPYHFTVNAAAETEPVDTAGDAADDPAIWLDPKNPQNSKLITTNKKSGLVVY
SLEGKTLHSYHTGKLNNVDIRYDFPLNGKKVDIAAASNRSEGKNTIEIYAIDGKN
GTLQSITDPDRPIASAIDEVYGFSLYHSQKTGRYYAMVTGKEGEFEQYELNADKN
GYISGKKVRAFKMNSQTEGMAADDEYGSLYIAEEDEAIWKFSAEPDGGSNGTVI
DRADGRHLTPDIEGLTIYYAADGKGYLLASSQGNSSYAIYERQGQNKYVADFQIT
DGPETDGTSDTDGIDVLGFGLGPEYPFGLFVAQDGENIDHGQKVNQNFKMVPWE
RIADKIGFHPQVNKQVDPRELTDRSGK (SEQ ID NO:42)

Figure 16

MVSISKLINNGLLLAGQSVYQDLATPQQSSVEQYNIIRFLGGSGPYIQRSGYGISTD
IPDQCTIKQVQLMSRHGERYPSKNSGKKLKTIYGKLKSYNGTFTGSLAFLNDYEY
FVPDDSLYEKETSALNSQGLFAGTTDALRHGAAFRAKYGSLYKQNSTLPVFTSNS
NRVYQTSEYFARGFLGDEFSDATVHFAIIIDEDPKMGVNSLTPRAACDNYNEDVN
DGIVNQYSTDYLDEALKRFQSSNPGLNLTSEDVYQLFAYCAYETNVKGASPFCD
LFTNEEYIQYSYSVDLSNYYSHGAGHNLTKTIGSTLLNASLTLLKDGTNDNKIWL
SFSHDTDLEIFHSALGIVEPAEDLPVDYIPFPSPYIHSQIVPQGARIYTEKYSCGNET
YVRYILNDAVVPIPKCSSGPGFSCELSKFEEYINKRLRDVDFVEQCDLKDAPTEVT
FYWDYTSVNYSASLING (SEQ ID NO:43)

Figure 17

MASERDPLLPVHGEGPESPSRRNWKTWIKHGILLILVLSTVIFFYFFSSHKSKGTNE
KPKFVIMMVSDGMGPGSLSMTRSFVETLNDKEGYRLPLDEHLIGSSRTRSSSSLIT
DSAAGATAFSCANKTYNGAVGVLDNEKPCGTILEAAKEAGYLTGIVVTSRVTDA
TPASFSAHAANRFMQDLIAEYQVGMGPLGRSVDLLFGGGLCSFLPKSTYRSCRSD
NLDLLKYARKKEGFQILLNRTDFDELSNAQLPLLGLFSDYHLSYDIDYQPEVQPK
LSEMVETALDVLLNATNEDTSKGFFLLIEGSRIDMASHNNDPIAHVYEVMEYNRA
FEIASAFVEKNGGSLISTSDHETGGLTVGRQVSKKYPEYLWKPQVLSLALHSIEYL
ASAVNHNQNTLLPYIEQFVLPAIGIPDPNPKQIHDIYVARHNIFNLINVLSDIVSVE
AQIGWTTHGHTAVDVNVYGVGEVTEHLRGNMENIEIGQFMEIYLNVSLSDVTEK
LKDAPIHGAPDRHCLVETSFSDRLVGFGADLF (SEQ ID NO:44)

Figure 21
A
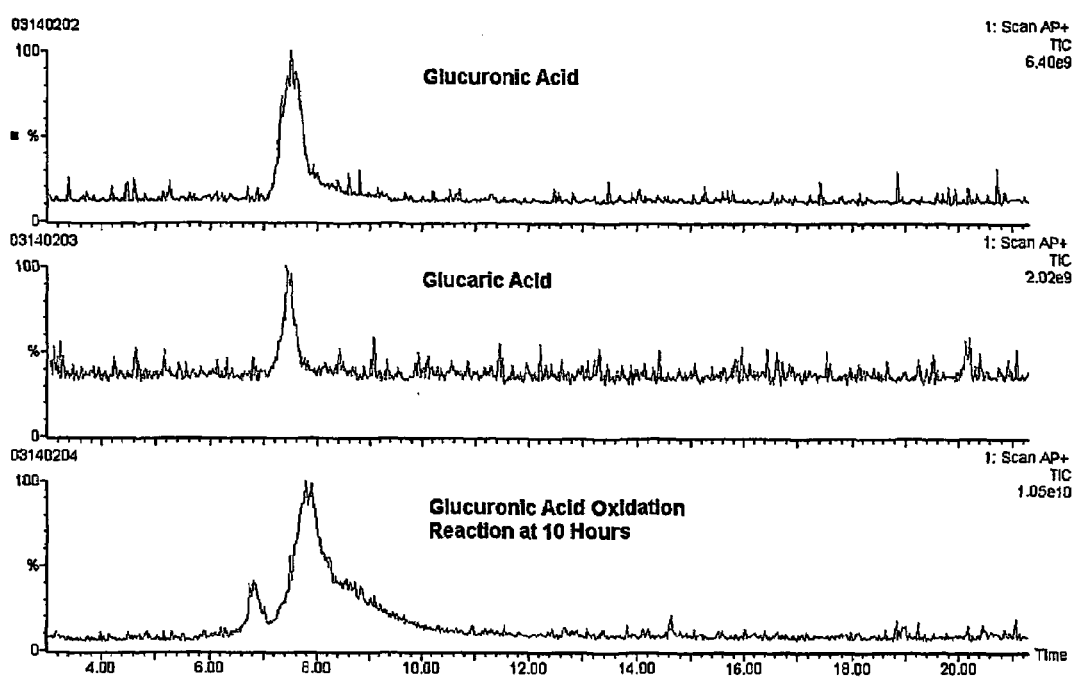
B
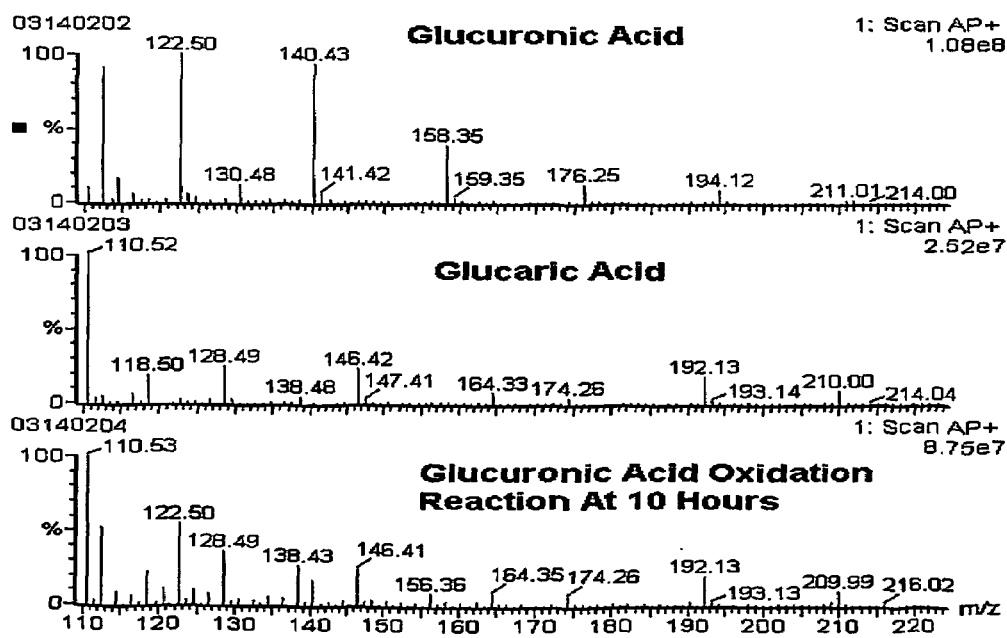

US 7,326,549 B2

MYO-INOSITOL OXYGENASES

CROSS REFERENCE TO RELATED APPLICATIONS

This application is a National Stage application under 35 U.S.C. §371 that claims the benefit of PCT/US02/08404, filed Mar. 19, 2002, which claims the benefit of U.S. Provisional application Ser. No. 60/277,148, filed Mar. 19, 2001.

BACKGROUND

1. Technical Field

The invention relates to methods and materials involved in producing organic compounds such as organic acids.

2. Background Information

Ascorbic acid (vitamin C) has many important nutritional uses. In fact, ascorbic acid is an essential nutrient to humans, and must be obtained from diet to prevent vitamin C deficiencies such as scurvy. In addition, some medical practitioners claim that ascorbic acid has the potential to prevent and treat the common cold, flu, and cancer. Thus, diet supplements containing ascorbic acid are widely used.

Ascorbic acid also has many important industrial uses. For example, ascorbic acid can be used in meat processing, nutritional supplements, and animal foods. In fact, several industrial manufactures can produce 10,000 metric tons annually of ascorbic acid and related ascorbic acid compounds such as calcium ascorbate and sodium ascorbate.

The "Reichstein" method is a commonly used method for producing ascorbic acid from D-glucose or a D-glucose precursor such as corn syrup. This method involves six discrete chemical steps as well as a fermentation step. For example, one of the chemical steps involves converting 2-keto-L-gulonic acid into ascorbic acid by treating the 2-keto-L-gulonic acid with acid at a temperature greater than 60° C.

Several other manufacturing processes containing at least one chemical step are also used to produce ascorbic acid. Specifically, ascorbic acid has been produced using methods that chemically convert D-glucose into L-sorbitol prior to a fermentation step, methods that chemically convert 2-keto-L-gulonic acid into ascorbic acid after a fermentation step, and methods that chemically convert D-glucose into L-sorbitol prior to a fermentation step in addition to chemically converting 2-keto-L-gulonic acid into ascorbic acid after a fermentation step.

SUMMARY

The present invention relates generally to methods and materials for producing organic compounds such as myo-inositol, glucuronic acid, glucaric acid, and ascorbic acid. Specifically, the invention provides cells (e.g., bacterial, fungal, and insect cells), methods for culturing cells, isolated nucleic acid molecules, and methods and materials for producing various organic compounds. The invention is based on the discovery that cells can be genetically manipulated such that they have the ability to produce a desired organic product. For example, the cells provided herein can produce ascorbic acid. It will be understood that the terms "ascorbate," "ascorbic acid," "L-ascorbate," "L-ascorbic acid," and "vitamin C" can be used interchangeably to refer to L-ascorbic acid. It also will be understood that the term "glucaric acid" as used herein refers to glucaric acid, glucaro-1,4-lactone, and glucaro-6,3-lactone since these three compounds freely interconvert when in solution.

The invention also is based on the discovery of efficient metabolic pathways that utilize glucose and/or phytic acid to produce ascorbic acid. Specifically, ascorbic acid can be produced from glucose and/or phytic acid using a metabolic pathway that can convert myo-inositol into glucuronate. In general, such pathways require less enzymatic steps than the native metabolic pathways used by plants and animals to produce ascorbic acid from glucose. Any method that can efficiently produce ascorbic acid from a carbon source such as glucose or phytic acid would be useful for large-scale production efforts. In addition, the methods and materials provided herein can be used to produce organic compounds without the need of chemical steps such as an acid treatment at high temperature (e.g., a temperature greater than 60° C.).

In general, one aspect of the invention features a method of providing a cell with a polypeptide having myo-inositol oxygenase activity. The method includes introducing a nucleic acid molecule into the cell, where the nucleic acid molecule encodes the polypeptide, and where the cell expresses the polypeptide. The cell can be a prokaryotic cell (e.g., a *Pseudomonas, Bacillus, Lactobacillus, Lactococcus*, or *Corynebacterium* cell). The cell can be a eukaryotic cell (e.g., a yeast, fungi, insect, or mammalian cell). The cell can be a *Saccharomyces, Pichia, Aspergillus, Cryptococcus, Schwanniomyces, Schizosaccharomyces, Spodoptera, Cricetulus*, or *Homo sapiens* cell. The nucleic acid molecule can be integrated into the genome of the cell. The polypeptide can contain an amino acid sequence at least about 50 percent identical (e.g., at least about 55, 60, 70, 75, 80, or 90 percent identical) to the sequence set forth in SEQ ID NO:12, 19, 20, 21, 22, 23, 24, 25, 26, 27, 28, 29, 30, 31, 32, 33, 34, or 35. The polypeptide can contain an amino acid sequence at least about 70 percent identical to the sequence set forth in SEQ ID NO:12, 19, 20, 21, 22, 23, 24, 25, 26, 27, 28, 29, 30, 31, 32, 33, 34, or 35. The cell can produce L-ascorbic acid. The cell can have glucuronate reductase activity. The cell can have 1,4-lactone hydroxyacylhydrolase activity, D-glucono-1,5-lactone lactonohydrolase activity, and/or uronolactonase activity. The cell can have gulono-γ-lactone oxidase activity, galactono-γ-lactone oxidase activity, and/or gulono-γ-lactone dehydrogenase activity. The cell can have phosphatase activity and/or phytase activity. The cell can lack L-gulonate 3-dehydrogenase activity. The cell can contain myo-inositol oxygenase activity with a specific activity greater than 40 mg glucuronic acid per gram dry cell weight per hour. The cell can contain myo-inositol oxygenase activity such that an extract from $1 \times 10^6$ cells contains a specific activity greater than 150 μg glucuronic acid formed per 10 mg total protein per 10 minutes, where each of the $1 \times 10^6$ cells is the cell or a progeny of the cell. The nucleic acid molecule can contain a promoter that is lactose unresponsive. The polypeptide can lack an N-terminal polyhistidine tag. The polypeptide can lack a glutathione-S-transferase sequence.

In another embodiment, the invention features methods of producing glucaric acid as well as cells capable of producing glucaric acid. These methods involve converting myo-inositol to glucuronic acid and converting glucuronic acid to glucaric acid. The substrates (e.g., myo-inositol and glucuronic acid) can be converted to their respective products using polypeptides or chemical conversions. A "chemical conversion" as used herein refers to the changing of a substrate to a product without the aid of a polypeptide having enzymatic activity. Moreover, these methods can be practiced in vivo, in vitro, or by using combinations of in vitro and in vivo steps. When polypeptides are used to convert glucuronic acid to glucaric acid, the polypeptides can have either aldehyde dehydrogenase activity, hexose oxidase activity, or aldehyde oxidase activity. When polypeptides are used to convert myo-inositol to glucuronic acid, the polypeptides can have myo-inositol oxygenase activity.

In another embodiment, the invention features a cell containing an exogenous nucleic acid molecule, where the exogenous nucleic acid molecule encodes a polypeptide having myo-inositol oxygenase activity, and where the cell expresses the polypeptide. The cell can be a prokaryotic cell (e.g., a *Pseudomonas, Bacillus, Lactobacillus, Lactococcus,* or *Corynebacterium* cell). The cell can be a eukaryotic cell (e.g., a yeast, fungi, insect, or mammalian cell). The cell can be a *Saccharomyces, Pichia, Aspergillus, Cryptococcus, Schwanniomyces, Schizosaccharomyces, Spodoptera, Cricetulus,* or *Homo sapiens* cell. The polypeptide can contain an amino acid sequence at least about 50 percent identical (e.g., at least about 55, 60, 70, 75, 80, or 90 percent identical) to the sequence set forth in SEQ ID NO:12, 19, 20, 21, 22, 23, 24, 25, 26, 27, 28, 29, 30, 31, 32, 33, 34, or 35. The polypeptide can contain an amino acid sequence at least about 70 percent identical to the sequence set forth in SEQ ID NO:12, 19, 20, 21, 22, 23, 24, 25, 26, 27, 28, 29, 30, 31, 32, 33, 34, or 35. The cell can contain a second exogenous nucleic acid molecule, where the second exogenous nucleic acid molecule encodes a second polypeptide, and where the cell expresses the second polypeptide. The second polypeptide can have glucuronate reductase activity. The second polypeptide can contain an amino acid sequence at least about 50 percent identical to the amino acid sequence set forth in SEQ ID NO:36. The second polypeptide can have 1,4-lactone hydroxyacylhydrolase activity, D-glucono-1,5-lactone lactonohydrolase activity, or uronolactonase activity. The second polypeptide can contain an amino acid sequence at least about 50 percent identical to the amino acid sequence set forth in SEQ ID NO:37 or 38. The second polypeptide can have gulono-γ-lactone oxidase activity, galactono-γ-lactone oxidase activity, or gulono-γ-lactone dehydrogenase activity. The second polypeptide can contain an amino acid sequence at least about 50 percent identical to the amino acid sequence set forth in SEQ ID NO:39 or 40. The second polypeptide can have phosphatase activity. The second polypeptide can contain an amino acid sequence at least about 50 percent identical to the amino acid sequence set forth in SEQ ID NO:41 or 44. The second polypeptide can have phytase activity. The second polypeptide can contain an amino acid sequence at least about 50 percent identical to the amino acid sequence set forth in SEQ ID NO:42 or 43. The cell can contain a second exogenous nucleic acid molecule and a third exogenous nucleic acid molecule, where the second exogenous nucleic acid molecule encodes a second polypeptide, where the third exogenous nucleic acid molecule encodes a third polypeptide, and where the cell expresses the second polypeptide and the third polypeptide. The second polypeptide can have glucuronate reductase activity, 1,4-lactone hydroxyacylhydrolase activity, D-glucono-1,5-lactone lactonohydrolase activity, gulono-γ-lactone oxidase activity, gulono-γ-lactone dehydrogenase activity, uronolactonase activity, galactono-γ-lactone oxidase activity, pyridine nucleotide transhydrogenase activity, phytase, and/or phosphatase activity. The third polypeptide can have glucuronate reductase activity, 1,4-lactone hydroxyacylhydrolase activity, D-glucono-1,5-lactone lactonohydrolase activity, gulono-γ-lactone oxidase activity, gulono-γ-lactone dehydrogenase activity, uronolactonase activity, galactono-γ-lactone oxidase activity, pyridine nucleotide transhydrogenase activity, phytase activity, and/or phosphatase activity. The cell can lack L-gulonate 3-dehydrogenase activity. The cell can have a genetic modification that reduces L-gulonate 3-dehydrogenase activity. The genetic modification can include a nucleic acid deletion in the genome of the cell. The cell can produce ascorbic acid. The cell can have pyridine nucleotide transhydrogenase activity. The cell can have myo-inositol oxygenase activity with a specific activity greater than 40 mg glucuronic acid per gram dry cell weight per hour. The cell can have myo-inositol oxygenase activity such that an extract from $1\times10^6$ cells comprises a specific activity greater than 150 µg glucuronic acid formed per 10 mg total protein per 10 minutes, where each of the $1\times10^6$ cells is the cell or a progeny of the cell. The exogenous nucleic acid molecule can contain a promoter that is lactose unresponsive. The polypeptide can lack an N-terminal polyhistidine tag. The polypeptide can lack a glutathione-S-transferase sequence. The exogenous nucleic acid molecule can be integrated into the genome of the cell.

In another aspect, the invention features a method of reducing myo-inositol oxygenase activity in a cell. The method includes genetically modifying the genome of the cell such that the expression of a polypeptide having the myo-inositol oxygenase activity is reduced. The cell can be a eukaryotic cell (e.g., a plant cell). The genetic modification can contain a nucleic acid deletion in the genome of the cell.

Another embodiment of the invention features a cell containing a genetic modification that reduces myo-inositol oxygenase activity. The cell can be a eukaryotic cell (e.g., a plant cell). The genetic modification can include a nucleic acid deletion in the genome of the cell. The cell can lack the myo-inositol oxygenase activity.

Another embodiment of the invention features a cell containing a genetic modification that reduces L-gulonate 3-dehydrogenase activity. The cell can be a eukaryotic cell. The genetic modification can include a nucleic acid deletion in the genome of the cell. The cell can lack the L-gulonate 3-dehydrogenase activity.

Another aspect of the invention features an isolated nucleic acid molecule containing a nucleic acid sequence at least about 50 percent identical to the sequence set forth in SEQ ID NO:1. The isolated nucleic acid molecule can encode a polypeptide having myo-inositol oxygenase activity. The nucleic acid sequence can be as set forth in SEQ ID NO:1.

In another embodiment, the invention features an isolated nucleic acid molecule that encodes a polypeptide having an amino acid sequence at least about 50 percent identical to the sequence set forth in SEQ ID NO:19. The polypeptide can have myo-inositol oxygenase activity. The amino acid sequence can be as set forth in SEQ ID NO:19.

Another aspect of the invention features a method for producing ascorbic acid. The method includes (a) contacting myo-inositol with a first polypeptide having myo-inositol oxygenase activity to form glucuronate, where the first polypeptide is within a cell, (b) contacting the glucuronate with a second polypeptide having glucuronate reductase activity to form gulonate, (c) contacting the gulonate with a third polypeptide to form gulono-γ-lactone, the third polypeptide having 1,4-lactone hydroxyacylhydrolase activity and/or D-glucono-1,5-lactone lactonohydrolase activity, and (d) contacting the gulono-γ-lactone with a fourth polypeptide to form the ascorbic acid, the fourth polypeptide having gulono-γ-lactone oxidase activity, galactono-γ-lactone oxidase activity, and/or gulono-γ-lactone dehydrogenase activity, where at least 10 mg (e.g., at least 20, 30, 40, 50, 100, or more mg) of ascorbic acid is produced per gram dry cell weight per hour.

Another embodiment of the invention features a method for producing ascorbic acid. The method includes (a) contacting myo-inositol with a first polypeptide having myo-inositol oxygenase activity to form glucuronate, where the first polypeptide is within a cell, (b) contacting the glucuronate with a second polypeptide having uronolactonase activity to form glucurono-lactone, (c) contacting the glucurono-lactone with a third polypeptide having glucuronolactone reductase activity to form gulono-γ-lactone, and (d) contacting the gulono-γ-lactone with a fourth polypeptide to form the ascorbic acid, the fourth polypeptide having gulono-γ-lactone oxidase activity, galactono-γ-lactone oxidase activity, and/or gulono-γ-lactone dehydrogenase activity, where at least 10 mg (e.g., at least 20, 30, 40, 50, 100, or more mg) of ascorbic acid is produced per gram dry cell weight per hour.

Another embodiment of the invention features a method for producing ascorbic acid. The method includes (a) contacting myo-inositol with a first polypeptide having myo-inositol oxygenase activity to form glucuronate, where the first polypeptide is extraceilular, (b) contacting the glucuronate with a second polypeptide having glucuronate reductase activity to form gulonate, (c) contacting the gulonate with a third polypeptide to form gulono-γ-lactone, the third polypeptide having 1,4-lactone hydroxyacylhydrolase activity and/or D-glucono-1,5-lactone lactonohydrolase activity, and (d) contacting the gulono-γ-lactone with a fourth polypeptide to form the ascorbic acid, the fourth polypeptide having gulono-γ-lactone oxidase activity, galactono-γ-lactone oxidase activity, and/or gulono-γ-lactone dehydrogenase activity.

Another embodiment of the invention features a method for producing ascorbic acid. The method includes (a) contacting myo-inositol with a first polypeptide having myo-inositol oxygenase activity to form glucuronate, where the first polypeptide is extracellular, (b) contacting the glucuronate with a second polypeptide having uronolactonase activity to form glucurono-lactone, (c) contacting the glucurono-lactone with a third polypeptide having glucuronolactone reductase activity to form gulono-γ-lactone, and (d) contacting the gulono-γ-lactone with a fourth polypeptide to form the ascorbic acid, the fourth polypeptide having gulono-γ-lactone oxidase activity, galactono-γ-lactone oxidase activity, and/or gulono-γ-lactone dehydrogenase activity.

Glucaric acid, containing two carboxylic acid functional groups, is potentially useful as an acidulent in the food and animal feed industries. Glucaric acid has also been shown to be useful as a chelating agent and can be used as a biodegradable detergent and an additive for cement. Glucaric acid, because it is a potent inhibitor of the enzyme beta-glucuronidase, has also been shown to be valuable as an anti-cancer agent and has been shown to lower serum cholesterol in mammals. Natural sources with particularly high levels of glucaric acid include fruits such as apples and grapefruit and vegetables such as brussel sprouts and broccoli. Because of its metal chelating properties, it can be used as a chelating agent of 99 Tcm for the detection of myocardial infarction and the radio-imaging of tumors. It also is a raw material for the production of polyhydroxylated polymers and as such can be used for the production of fibers, films, and adhesives.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIGS. 7A-C shows an alignment of 17 amino acid sequences.

FIG. 9 is a sequence listing containing an amino acid sequence from a polypeptide having glucuronate reductase activity. The threonine at position number 2 can be an alanine.

FIG. 10 is a sequence listing containing an amino acid sequence from a polypeptide having D-glucono-1,5-lactone lactonohydrolase activity. The threonine at position number 2 can be an alanine; the valine at position 16 can be an alanine; the methionine at position 17 can be an isoleucine; the glutamic acid at position 34 can be a glutamine; and a valine can be inserted after the valine at position 162.

FIG. 11 is a sequence listing containing an amino acid sequence from a polypeptide having uronolactonase activity. The amino acid residues from position number 2 through position number 20 can be removed to form a mature polypeptide.

FIG. 12 is a sequence listing containing an amino acid sequence from a polypeptide having gulono-γ-lactone oxidase activity. The isoleucine at position number 85 can be an valine, and the glutamine at position 189 can be a histidine.

FIG. 13 is a sequence listing containing an amino acid sequence from a polypeptide having galactono-γ-lactone oxidase activity.

FIG. 14 is a sequence listing containing an amino acid sequence from a polypeptide having acid phosphatase activity.

FIG. 15 is a sequence listing containing an amino acid sequence from a polypeptide having phytase activity.

FIG. 16 is a sequence listing containing an amino acid sequence from a polypeptide having phytase activity.

FIG. 17 is a sequence listing containing an amino acid sequence from a polypeptide having phosphatase activity.

FIG. 21 contains HPLC and mass spectrometry graphs demonstrating the conversion of glucuronic acid into glucaric acid.

DETAILED DESCRIPTION

The invention provides methods and materials related to producing organic compounds such as myo-inositol and ascorbic acid. Specifically, the invention provides cells, methods for culturing cells, isolated nucleic acid molecules, and methods and materials for producing various organic compounds. In addition, the invention provides several metabolic pathways that can be used to produce ascorbic acid.

1. Seven Step Metabolic Pathways

Figure 1:
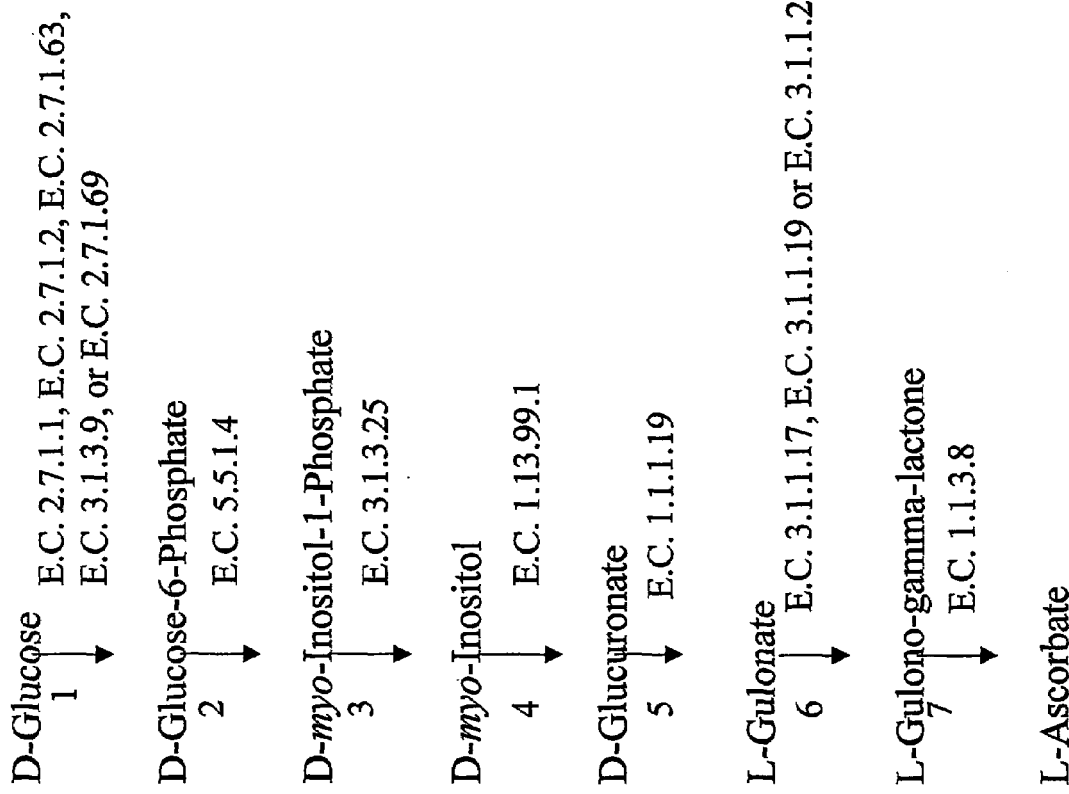
FIG. 1 is a diagram depicting a seven step metabolic pathway that can produce ascorbic acid from glucose using D-myo-inositol and L-gulonate as intermediates.
Figure 2:
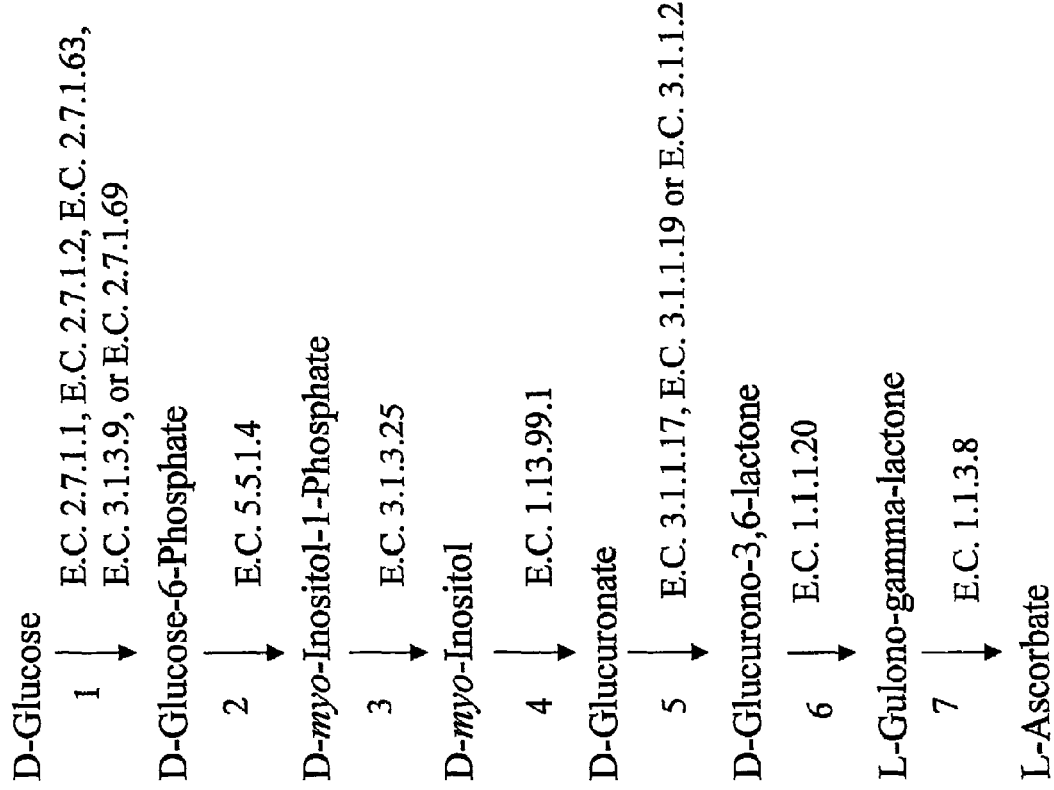
FIG. 2 is a diagram depicting a seven step metabolic pathway that can produce ascorbic acid from glucose using D-myo-inositol and D-glucurono-3,6-lactone as intermediates.

The invention provides several seven step metabolic pathways that can produce ascorbic acid from glucose (FIGS. 1 and 2). As depicted in step one of FIG. 1, D-glucose can be converted into D-glucose-6-phosphate by a polypeptide having either hexokinase activity (EC 2.7.1.1) or glucokinase activity (EC 2.7.1.2). Polypeptides having hexokinase activity as well as nucleic acid encoding such polypeptides can be obtained from various species including, without limitation, *Homo sapiens, Rattus norvegicus, Saccharomyces cerevisiae, Arabidopsis thaliana*, and *Aspergillus niger*. Polypeptides having glucolinase activity as well as nucleic acid encoding such polypeptides can be obtained from various species including, without limitation, *Bos taurus, Rattus norvegicus, Mus musculus, Homo sapiens, Saccharomyces cerevisiae, Schistosoma mansoni, Aspergillus nidulans, Schizosaccharomyces pombe, Arabidopsis thaliana, Kluyveromyces lactis, Schwanniomyces occidentalis* (also known as *Debaryomyces occidentalis*), *Plasmodium falciporm, Bacillus subtilis, Aspergillus niger, Staphylococcus xylosus, Brucella abortus, Zymomonas mobilis, Escherichia coli*, and *Streptomyces coelicolor*. For example, nucleic acid that encodes a polypeptide having glucokinase activity can be obtained from *Aspergillus niger* and can have a sequence as set forth in GenBank® Accession Number X99626.

Alternatively, D-glucose can be converted into D-glucose-6-phosphate by a polypeptide having either polyphosphate:D-glucose 6-phosphotransferase activity (EC 2.7.1.63) or D-glucose-6-phosphate phosphohydrolase activity (EC 3.1.3.9), or extracellular D-glucose can be transported into a cell and converted into D-glucose-6-phosphate by a polypeptide having protein-N(pai)-phosphohistidine-sugar phosphotransferase activity (EC 2.7.1.69). Polypeptides having polyphosphate:D-glucose 6-phosphotransferase activity as well as nucleic acid encoding such polypeptides can be obtained from various species including, without limitation, *Mycobacterium tuberculosis*. Polypeptides having D-glucose-6-phosphate phosphohydrolase activity as well as nucleic acid encoding such polypeptides can be obtained from various species including, without limitation, *Rattus norvegicus* and *Homo sapiens*. For example, nucleic acid that encodes a polypeptide having D-glucose-6-phosphate phosphohydrolase activity can be obtained from *Rattus norvegicus* and can have a sequence as set forth in GenBank® Accession Number U07993. Polypeptides having protein-N(pai)-phosphohistidine-sugar phosphotransferase activity as well as nucleic acid encoding such polypeptides can be obtained from various species including, without limitation, *Escherichia coli* and *Bacillus subtilis*.

In step two, the resulting D-glucose-6-phosphate can be converted into D-myo-inositol-1-phosphate by a polypeptide having myo-inositol-1-phosphate synthase activity (EC 5.5.1.4). Polypeptides having myo-inositol-1-phosphate synthase activity as well as nucleic acid encoding such polypeptides can be obtained from various species including, without limitation, *Arabidopsis thaliana, Saccharomyces cerevisiae, Citrus paradisi, Candida albicans*, and *Spirodela polyrrhiza*. For example, nucleic acid that encodes a polypeptide having myo-inositol-1-phosphate synthase activity can be obtained from *Saccharomyces cerevisiae* and can have a sequence as set forth in GenBank® Accession Number J04453.

In step three, D-myo-inositol-1-phosphate can be converted into D-myo-inositol by a polypeptide having myo-inositol-1 (or 4) monophosphatase activity (EC 3.1.3.25). Polypeptides having myo-inositol-1(or 4) monophosphatase activity as well as nucleic acid encoding such polypeptides can be obtained from various species including, without limitation, *Homo sapiens, Bos taurus, Mus musculus, Rattus norvegicus, Lycopersicon esculentum, Xenopus laevis*, and *Mesembryanthemum crystallinum*. For example, nucleic acid that encodes a polypeptide having myo-inositol-1(or 4) monophosphatase activity can be obtained from *Homo sapiens* and can have a sequence as set forth in GenBank® Accession Number NM_005536.

In step four, the resulting D-myo-inositol can be converted into D-glucuronate by a polypeptide having myo-inositol oxygenase activity (EC 1.13.99.1). Polypeptides having myo-inositol oxygenase activity as well as nucleic acid encoding such polypeptides can be obtained from various species including, without limitation, *Rattus norvegicus, Sus scrofa, Bos taurus, Cryptococcus neoformans, Schwanniomyces occidentalis, Homo sapiens, Avena sativa, Pinus radiata, Cryptococcus terreus, Arabidopsis thaliana*, and *Pleurotus ostreatus*.

In step five, D-glucuronate can be converted into L-gulonate by a polypeptide having glucuronate reductase activity (EC 1.1.1.19). Polypeptides having glucuronate reductase activity as well as nucleic acid encoding such polypeptides can be obtained from various species including, without limitation, *Rattus norvegicus, Sus scrofa*, and *Bos taurus*.

In step six, the resulting L-gulonate can be converted into L-gulono-γ-lactone by a polypeptide having 1,4-lactone hydroxyacylhydrolase activity (EC 3.1.1.25), D-glucono-1,5-lactone lactonohydrolase activity (EC 3.1.1.17), or uronolactonase activity (E.C. 3.1.1.19). Polypeptides having 1,4-lactone hydroxyacylhydrolase activity as well as nucleic acid encoding such polypeptides can be obtained from various species including, without limitation, *Homo sapiens* and *Rattus norvegicus*. Polypeptides having D-glucono-1,5-lactone lactonohydrolase activity as well as nucleic acid encoding such polypeptides can be obtained from various species including, without limitation, *Zymomonas mobilis, Escherichia coli, Saccharomyces cerevisiae, Aspergillus niger, Rattus norvegicus, Sus scrofa,* and *Bos taurus.* For example, nucleic acid that encodes a polypeptide having D-glucono-1,5-lactone lactonohydrolase activity can be obtained from *Zymomonas mobilis* and can have a sequence as set forth in GenBank® Accession Number X67189. Polypeptides having uronolactonase activity as well as nucleic acid encoding such polypeptides can be obtained from various species including, without limitation, *Fusarium oxysporum, Aryctolagus cuniculas, Cavia parcellus, Canis familiaris, Macaca philippinensis, Rattus norvegicus, Sus scrofa,* and *Bos taurus.* For example, nucleic acid that encodes a polypeptide having uronolactonase activity can be obtained from *Fusarium oxysporum* and can encode a sequence as set forth in GenBank® Accession Number BAA34218.

In step seven, L-gulono-γ-lactone can be converted into L-ascorbate by a polypeptide having gulono-γ-lactone oxidase activity (EC 1.1.3.8), apolypeptide having galactono-γ-lactone oxidase activity (EC 1.1.3.24), or a polypeptide having gulono-γ-lactone dehydrogenase activity. Polypeptides having gulono-γ-lactone oxidase activity as well as nucleic acid encoding such polypeptides can be obtained from various species including, without limitation, *Rattus norvegicus, Tachyglossus aculeatus, Ornithorhynchus anatinus, Perameles nasuta, Isoodon macrourus, Macropus rufogiseus, Thylogale thetis, Limulus polyphemus, Gallus gallus, Rana catesbeiana, Capra hircus,* and *Mus musculus.* For example, nucleic acid that encodes a polypeptide having gulono-γ-lactone oxidase activity can be obtained from rat and can encode a sequence as set forth in GenBank® Accession Number P10867. Polypeptides having galactono-γ-lactone oxidase activity as well as nucleic acid encoding such polypeptides can be obtained from various species including, without limitation, *Saccharomyces cerevisiae.* For example, nucleic acid that encodes a polypeptide having galactono-γ-lactone oxidase activity can be obtained from *Saccharomyces cerevisiae* and can encode a sequence as set forth in GenBank® Accession Number BAA23804. Polypeptides having gulono-γ-lactone dehydrogenase activity as well as nucleic acid encoding such polypeptides can be obtained from various species including, without limitation, *Euglena gracilis* (See, e.g., U.S. Pat. No. 5,250,428).

The seven step metabolic pathway depicted in FIG. 2 is identical to the pathway depicted in FIG. 1 except that, in step five, D-glucuronate can be converted into D-glucurono-3,6-lactone by a polypeptide having either 1,4-lactone hydroxyacylhydrolase activity (EC 3.1.1.25) or D-glucono-1,5-lactone lactonohydrolase activity (EC 3.1.1.17) or uronolactonase activity (EC 3.1.1.19) and, in step six, the resulting D-glucurono-3,6-lactone can be converted into L-gulono-γ-lactone by a polypeptide having glucuronolactone reductase activity (EC 1.1.1.20). Polypeptides having uronolactonase activity as well as nucleic acid encoding such polypeptides can be obtained from various species including, without limitation, *Fusarium oxysporum, Oryctolagus cuniculus, Cavia porcellus, Canis familiaris, Macaca philippinensis, Rattus norvegicus, Sus scrofa,* and *Bos taurus,* while polypeptides having glucuronolactone reductase activity as well as nucleic acid encoding such polypeptides can be obtained from various species including, without limitation, *Rattus norvegicus.* For example, nucleic acid that encodes a polypeptide having uronolactonase activity can be obtained from *Fusarium oxysporum* and can encode a sequence as set forth in GenBank® Accession Number BAA34218.

2. Eight Step Metabolic Pathways

Figure 3:
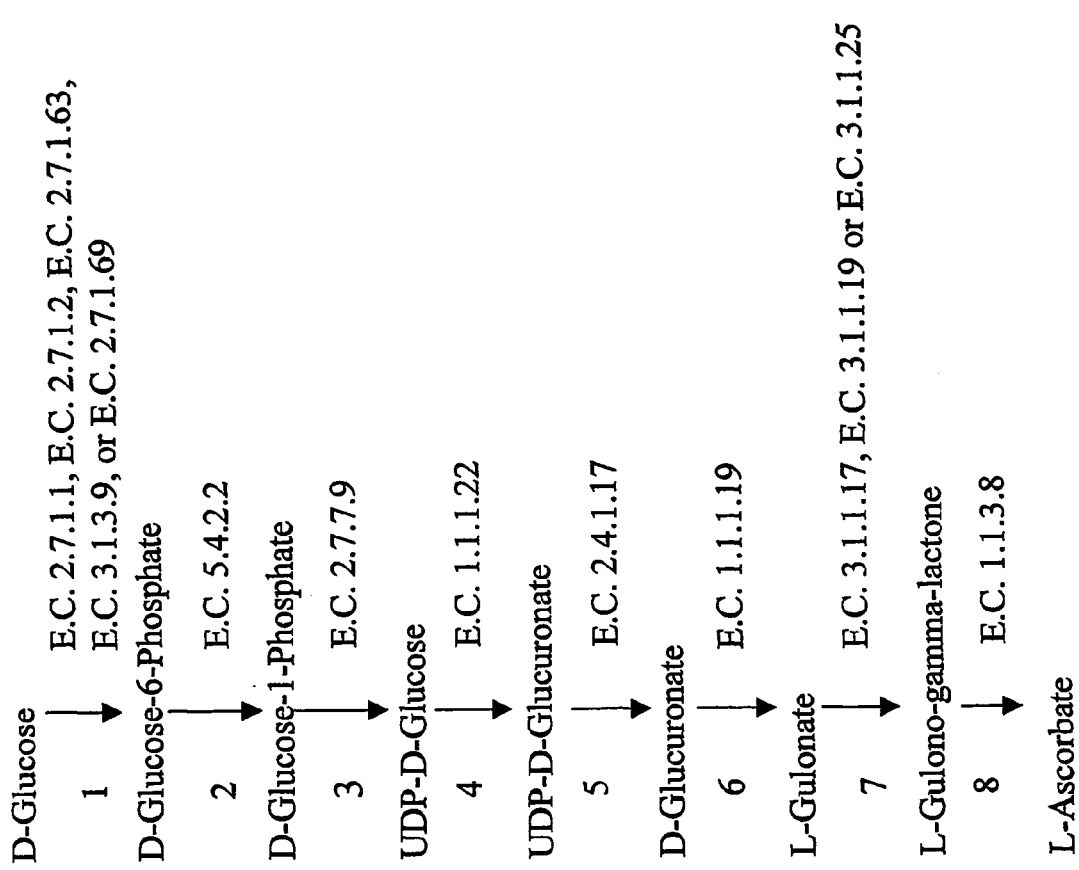
FIG. 3 is a diagram depicting an eight step metabolic pathway that can produce ascorbic acid from glucose using UDP-D-glucuronate and L-gulonate as intermediates.
Figure 4:
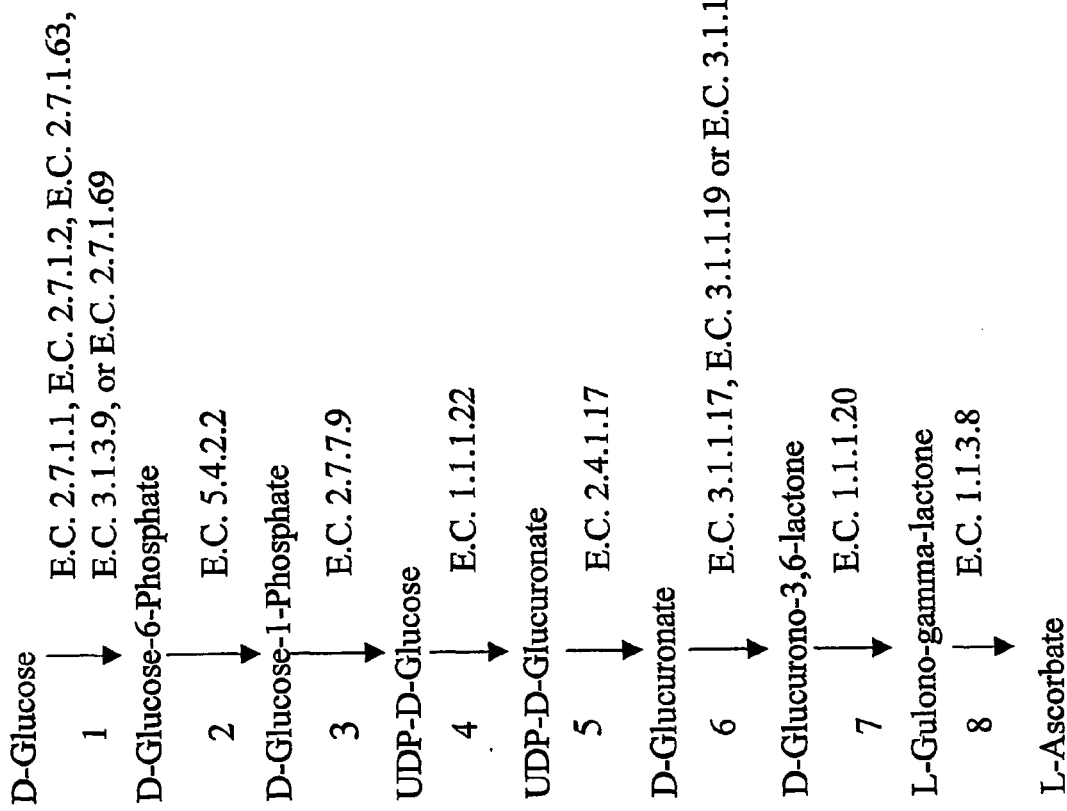
FIG. 4 is a diagram depicting an eight step metabolic pathway that can produce ascorbic acid from glucose using UDP-D-glucuronate and D-glucurono-3,6-lactone as intermediates.

The invention provides several eight step metabolic pathways that can produce ascorbic acid from glucose (FIGS. 3 and 4). As depicted in step one of FIG. 3, D-glucose can be converted into D-glucose-6-phosphate in the same manner as described in the seven step metabolic pathways depicted in FIGS. 1 and 2. For example, D-glucose can be converted into D-glucose-6-phosphate by a polypeptide having hexokinase activity (EC 2.7.1.1), glucokinase activity (EC 2.7.1.2), polyphosphate:D-glucose 6-phosphotransferase activity (EC 2.7.1.63), or D-glucose-6-phosphate phosphohydrolase activity (EC 3.1.3.9), or extracellular D-glucose can be transported into a cell and converted into D-glucose-6-phosphate by a polypeptide having protein-N(pai)-phosphohistidine-sugar phosphotransferase activity (EC 2.7.1.69).

In step two, the resulting D-glucose-6-phosphate can be converted into D-glucose-1-phosphate by a polypeptide having phosphoglucomutase activity (EC 5.4.2.2). Polypeptides having phosphoglucomutase activity as well as nucleic acid encoding such polypeptides can be obtained from various species including, without limitations *Arabidopsis thaliana, Homo sapiens, Saccharomyces cerevisiae,* and *Xanthomonas campestris.* For example, nucleic acid that encodes a polypeptide having phosphoglucomutase activity can be obtained from *Saccharomyces cerevisiae* and can have a sequence as set forth in GenBank® Accession Number X72016.

In step three, D-glucose-1-phosphate can be converted into UDP-D-glucose by a polypeptide having UTP-glucose-phosphate uridylyltransferase activity (EC 2.7.7.9). Polypeptides having UTP-glucose-1-phosphate uridylyltransferase activity as well as nucleic acid encoding such polypeptides can be obtained from various species including, without limitation, *Bos taurus, Solanum tuberosum, Pseudomonas aeruginosa, Bacillus subtilis,* and *Escherichia coli.* For example, nucleic acid that encodes a polypeptide having UTP-glucose-1-phosphate uridylyltransferase activity can be obtained from *Bos taurus* and can have a sequence as set forth in GenBank® Accession Number L14019.

In step four, the resulting UDP-D-glucose can be converted into UDP-D-glucuronate by a polypeptide having UDP-glucose dehydrogenase activity (EC 1.1.1.22). Polypeptides having UDP-glucose dehydrogenase activity as well as nucleic acid encoding such polypeptides can be obtained from various species including, without limitation, *Homo sapiens, Bos taurus, Mus musculus, Drosophila melanogaster,* and *Pseudomonas aeruginosa.* For example, nucleic acid that encodes a polypeptide having UDP-glucose dehydrogenase activity can be obtained from *Pseudomonas aeruginosa* and can have a sequence as set forth in GenBank® Accession Number AJ010734.

In step five, the resulting UDP-D-glucuronate can be converted into D-glucuronate by a polypeptide having UDP-glucuronate β-D-glucuronosyltranferase activity (EC 2.4.1.17). Polypeptides having UDP-glucuronate β-D-glucuronosyltransferase activity as well as nucleic acid encoding such polypeptides can be obtained from various species including, without limitation, *Homo sapiens, Rattus norvegicus,* and *Mus musculus.* For example, nucleic acid that encodes a polypeptide having UDP-glucuronate β-D-glucuronosyltransferase activity can be obtained from *Homo sapiens* and can have a sequence as set forth in GenBank® Accession Number NM_001072.

In step six, D-glucuronate can be converted into L-gulonate by a polypeptide having glucuronate reductase activity (EC 1.1.1.19). Polypeptides having glucuronate reductase activity as well as nucleic acid encoding such polypeptides can be obtained from various species including, without limitation, *Rattus norvegicus*, *Sus scrofa*, and *Bos taurus*.

In step seven, the resulting L-gulonate can be converted into L-gulono-γ-lactone by a polypeptide having either 1,4-lactone hydroxyacylhydrolase activity (EC 3.1.1.25) or D-glucono-1,5-lactone lactonohydrolase activity (EC 3.1.1.17) or uronolactonase activity (EC 3.1.1.19). Polypeptides having 1,4-lactone hydroxyacylhydrolase activity as well as nucleic acid encoding such polypeptides can be obtained from various species including, without limitation, *Rattus norvegicus* and *Homo sapiens*, while polypeptides having D-glucono-1,5-lactone lactonohydrolase activity as well as nucleic acid encoding such polypeptides can be obtained from various species including, without limitation, *Zymomonas mobilis*, *Escherichia coli*, *Saccharomyces cerevisiae*, *Aspergillus niger*, *Rattus norvegicus*, *Sus scrofa*, and *Bos taurus*. For example, nucleic acid that encodes a polypeptide having D-glucono-1,5-lactone lactonohydrolase activity can be obtained from *Zymomonas mobilis* and can have a sequence as set forth in GenBank® Accession Numbers X67189 and S53050.

In step eight, L-gulono-γ-lactone can be converted into L-ascorbate by a polypeptide having gulono-γ-lactone oxidase activity (EC 1.1.3.8), a polypeptide having galactono-γ-lactone oxidase activity (EC1.1. 1.3.24), or a polypeptide having gulono-γ-lactone dehydrogenase activity. Polypeptides having gulono-γ-lactone oxidase activity as well as nucleic acid encoding such polypeptides can be obtained from various species including, without limitation, *Rattus norvegicus*, *Tachyglossus aculeatus*, *Ornithorhynchus anatinus*, *Perameles nasuta*, *Isoodon macrourus*, *Macropus rufogiseus*, *Thylogale thetis*, *Limulus polyphemus*, *Gallus gallus*, *Rana catesbeiana*, and *Capra hircus*. For example, nucleic acid that encodes a polypeptide having gulono-γ-lactone oxidase activity can be obtained from rat and can encode a sequence as set forth in GenBank® Accession Number P10867. Polypeptides having galactono-γ-lactone oxidase activity as well as nucleic acid encoding such polypeptides can be obtained from various species including, without limitation, *Saccharomtyces cerevisiae*. For example, nucleic acid that encodes a polypeptide having galactono-γ-lactone oxidase activity can be obtained from *Saccharomyces cerevisiae* and can encode a sequence as set forth in GenBank® Accession Number BAA23804. Polypeptides having gulono-γ-lactone dehydrogenase as well as nucleic acid encoding such polypeptides can be obtained from various species including, without limitation, *Euglena gracilis* (See, e.g., U.S. Pat. No. 5,250,428).

The eight step metabolic pathway depicted in FIG. 4 is identical to the pathway depicted in FIG. 3 except that, in step six, D-glucuronate can be converted into D-glucurono-3,6-lactone by a polypeptide having either 1,4-lactone hydroxyacylhydrolase activity (EC 3.1.1.25) or D-glucono-1,5-lactone lactonohydrolase activity (EC 3.1.1.17) or uronolactonase activity (EC 3.1.1.19) and, in step seven, the resulting D-glucurono-3,6-lactone can be converted into L-gulono-γ-lactone by a polypeptide having glucuronolactone reductase activity (EC 1.1.1.20). Polypeptides having uronolactonase activity as well as nucleic acid encoding such polypeptides can be obtained from various species including, without limitation, *Fusarium oxysporum*, *Oryctolagus cuniculus*, *Cavia porcellus*, *Canis familiaris*, *Macaca philippinensis*, *Rattus norvegicus*, *Sus scrofa*, and *Bos taurus*, while polypeptides having glucuronolactone reductase activity as well as nucleic acid encoding such polypeptides can be obtained from various species including, without limitation, *Rattus norvegicus*.

3. Nine Step Metabolic Pathways

Figure 5:
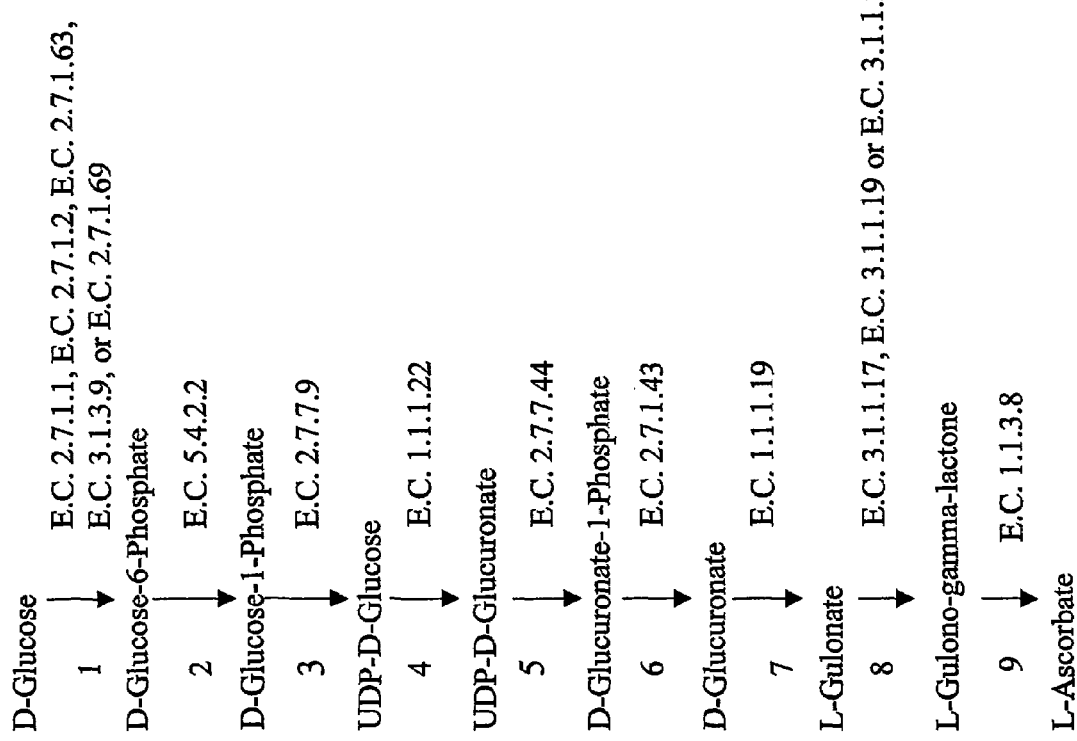
FIG. 5 is a diagram depicting a nine step metabolic pathway that can produce ascorbic acid from glucose using UDP-D-glucuronate and L-gulonate as intermediates.
Figure 6:
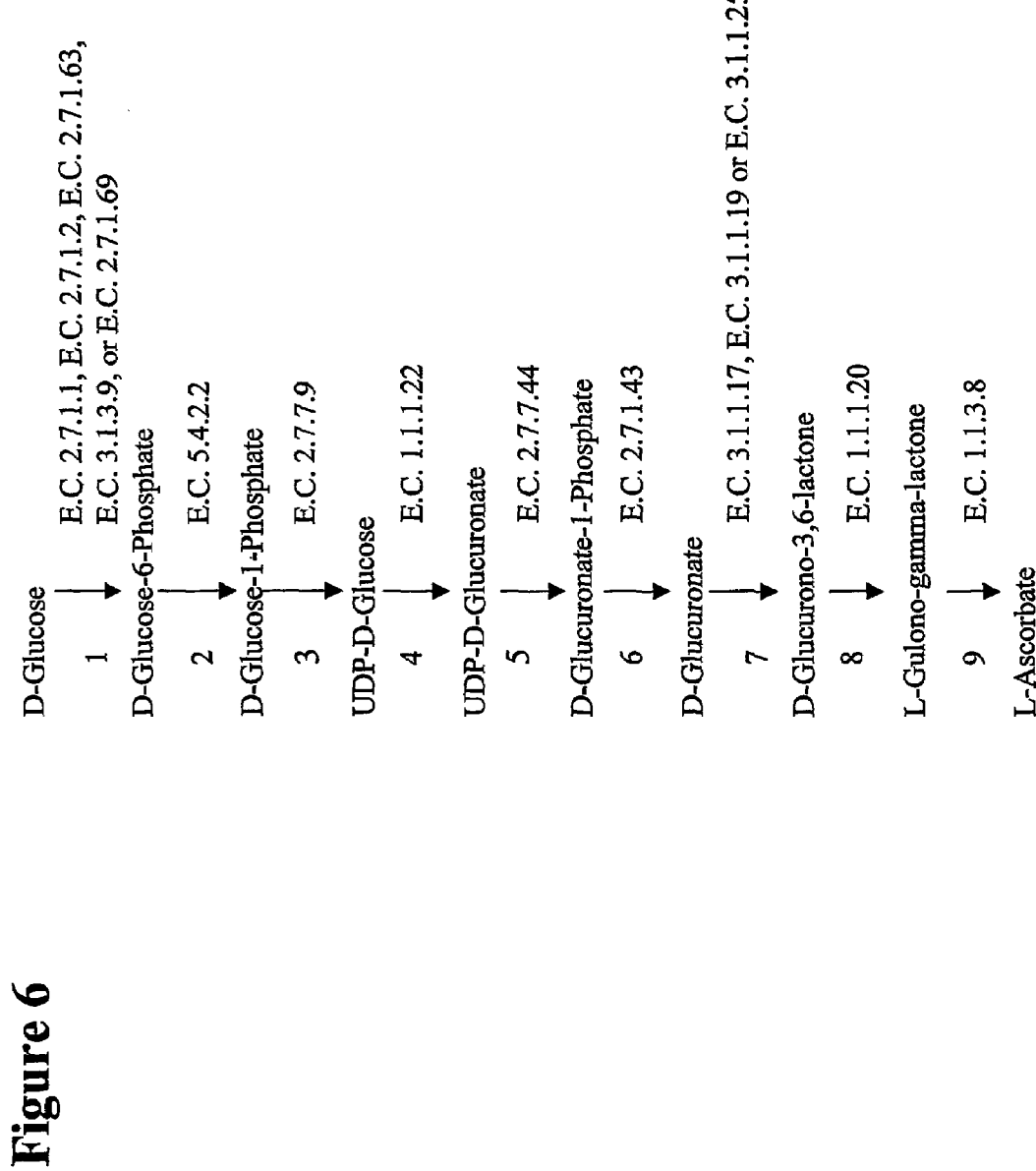
FIG. 6 is a diagram depicting a nine step metabolic pathway that can produce ascorbic acid from glucose using UDP-D-glucuronate and D-glucurono-3,6-lactone as intermediates.

The invention provides several nine step metabolic pathways that can produce ascorbic acid from glucose (FIGS. 5 and 6). The nine step metabolic pathways depicted in FIGS. 5 and 6 are similar to the eight step metabolic pathways depicted in FIGS. 3 and 4, respectively, except that the conversion of UDP-D-glucuronate into D-glucuronate uses a D-glucuronate-1-phosphate intermediate. As depicted in FIGS. 5 and 6, step five involves the conversion of UDP-D-glucuronate into D-glucuronate-1-phosphate by a polypeptide having UTP:1-phospho-α-D-glucuronate uridylyltransferase activity (EC 2.7.7.44). Polypeptides having UTP:1-phospho-α-D-glucuronate uridylyltransferase activity as well as nucleic acid encoding such polypeptides can be obtained from various species including, without limitation, *Hordeum vulgare* and *Typha latifolia*.

In step six, the resulting D-glucuronate-1-phosphate can be converted into D-glucuronate by a polypeptide having ATP:D-glucuronate 1-phosphotransferase activity (EC 2.7.1.43). Polypeptides having ATP:D-glucuronate 1-phosphotransferase activity as well as nucleic acid encoding such polypeptides can be obtained from various species including, without limitation, *Vigna radiata*, *Nicotiana tabacum*, *Lilium longiflorum*, *Zea mays*, and *Glycine max*.

4. Phytic Acid

The invention provides several pathways that can be used to produce myo-inositol or ascorbic acid from phytic acid. For example, phytic acid can be converted into myo-inositol by a polypeptide having phytase activity, by a polypeptide having phosphatase activity (or a collection of polypeptides having different phosphatase activities), or a mixture of polypeptides having phytase activity and polypeptides having phosphatase activity (or a collection of polypeptides having different phosphatase activities). For example, a polypeptide having phytase activity can be used to convert phytic acid into myo-inositol. Polypeptides having phytase activity as well as nucleic acid encoding such polypeptides can be obtained from various species including, without limitation, *Schwanniomyces occidentalis*, *Bacillus subtilis*, *E. coli*, *Aspergillus terreus*, *Homo sapiens*, and *Zea mays*. For example, nucleic acid that encodes a polypeptide having phytase activity can be obtained from *E. coli* and can have a sequence as set forth in GenBank® Accession Number M58708, or can be obtained from *Bacillus subtilis* and can have a sequence as set forth in GenBank® Accession Number AF298179 or AI277890. Also, polypeptides having phytase activity as well as nucleic acid encoding such polypeptides can be obtained as described in U.S. Pat. No. 5,830,733; 5,840,561; or 5,830,732. In one embodiment, a polypeptide having the sequence set forth in FIG. 16 can be used to convert phytic acid into myo-inositol. Alternatively, a polypeptide mixture having multiple inositol polyphosphate phosphatase activities can be used to convert phytic acid into myo-inositol. Polypeptides having phosphatase activity (e.g., acid phosphatase activity) as well as nucleic acid encoding such polypeptides can be obtained from various species including, without limitation, *E. coli*, *Saccharomyces cerevisiae*, *Schizosaccharomyces pombe*, *Candida albicans*, and *Aspergillus niger*. For example, nucleic acid that encodes a polypeptide having phosphatase activity can be obtained from *E. coli* and can encode a sequence as set forth in GenBank® Accession Number P07102. Also, polypeptides having phosphatase activity as well as nucleic acid encoding such polypeptides can be obtained as described in U.S. Pat. No. 5,830,733. A mixture of polypeptides having phytase activity and polypeptides having phosphatase activities can be used to convert phytic acid into inositol as described in U.S. Pat. No. 5,830,733. In addition, phytic acid can be converted into myo-inositol using any chemical technique such as heat or steam treatments.

The resulting myo-inositol can be converted into any other organic compound (e.g., ascorbic acid) using any of the enzymatic steps described herein. For example, myo-inositol can be converted into ascorbic acid using steps four through seven of the seven step metabolic pathway of FIG. 1.

5. Glucaric Acid

Figure 18:
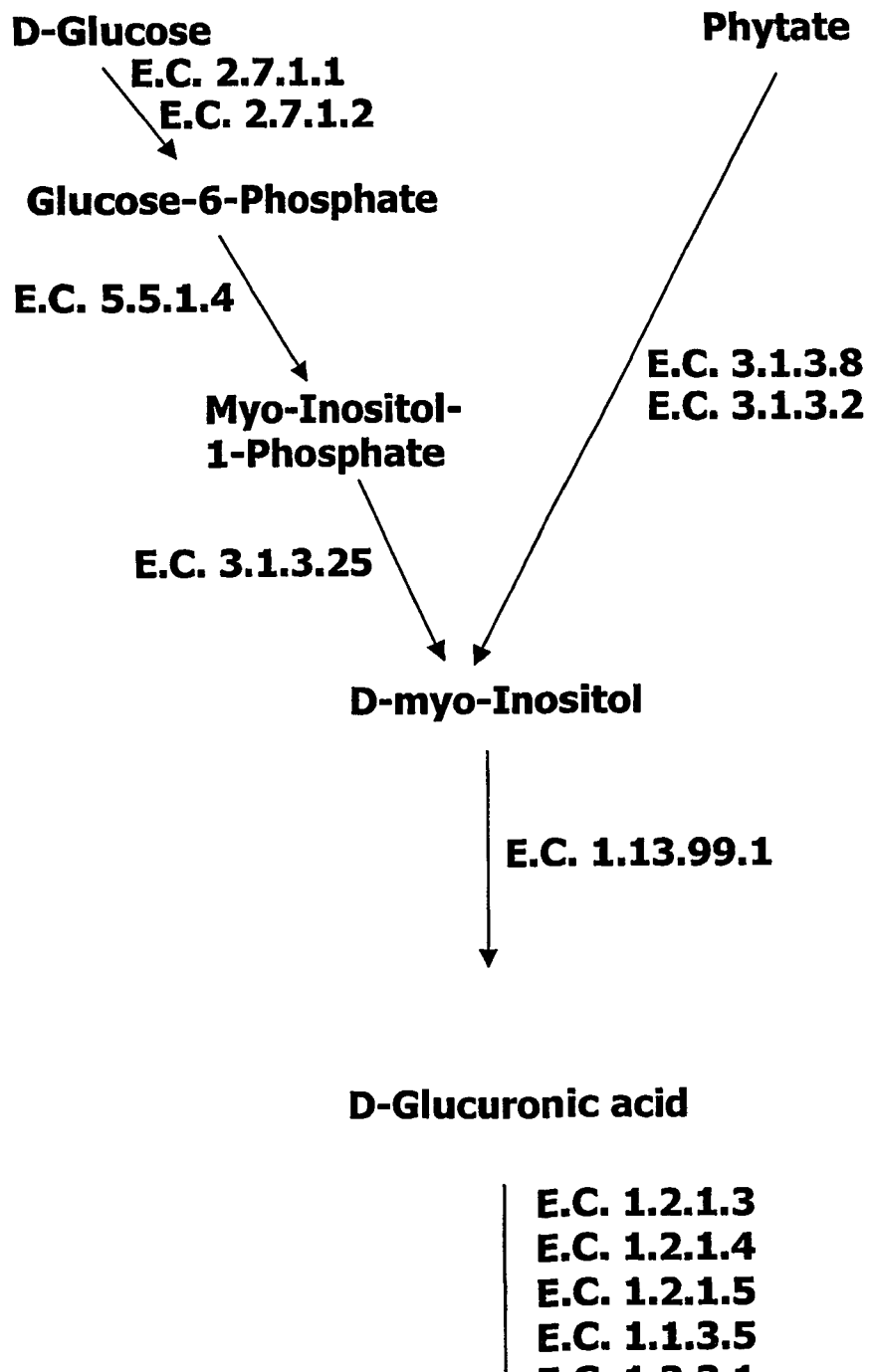
FIG. 18 is a diagram depicting a metabolic pathway that can produce D-glucaric acid from glucose or phytate.

The invention provides pathways that can be used to produce glucaric acid (FIG. 18). For example, glucose or phytic acid can be converted into glucuronic acid as described herein. The resulting glucuronic can be converted into glucaric acid by a polypeptide having non-specific hexose oxidase activity (EC 1.1.3.5), by a polypeptide having aldehyde dehydrogenase [NAD(P)] activity (EC 1.2.1.5, EC 1.2.1.3 (NAD), or EC 1.2.1.4 (NADP)), or by a polypeptide having aldehyde oxidase activity (EC 1.2.3.1). For example, a polypeptide having non-specific hexose oxidase activity can be used to convert glucuronic into glucaric acid. Polypeptides having non-specific hexose oxidase activity as well as nucleic acid encoding such polypeptides can be obtained from various species including, without limitation, *Chondrus crispus, Yersini apestis, Yersinia pseudotuberculosis*, and *Ralstonia solanacearum*. For example, nucleic acid that encodes a polypeptide having non-specific hexose oxidase activity can be obtained from *Chondrus crispus* and can encode an amino acid sequence as set forth in GenBank® Accession Number AAB49376.1, or can be obtained from *Yersinia pestis* and can encode an amino acid sequence as set forth in GenBank® Accession Number NP_403959.1, or can be obtained from *Ralstonia solanacearum* and can encode an amino acid sequence as set forth in GenBank® Accession Number NP_518171.1. Also, polypeptides having hexose oxidase activity as well as nucleic acid encoding such polypeptides can be obtained as described elsewhere (U.S. Pat. No. 6,251,626 and Sullivan and Ikawa, *Biochimica et Biophysica Acta*, 309:11-22 (1973)). In addition, glucuronic can be converted into glucaric acid using any chemical technique such as oxidation using molecular oxygen and a catalyst For example, methods similar to those described in U.S. Pat. No. 5,817,870 or Gallezot et al. (*Chem. Ind. (Dekker)*, 62:331-40 (1995)) can be used to convert glucuronic into glucaric acid.

Additionally, a polypeptide having aldehyde dehydrogenase activity can be used to convert glucuronic into glucaric acid. Polypeptides having aldehyde dehydrogenase activity as well as nucleic acid encoding such polypeptides can be obtained from various species including, without limitation, *Bacillus stearothermophilus* (gi:1169292) and *Bacillus subtilus* (gi:16077316 or NP_388129.1). Similarly, a polypeptide having aldehyde oxidase activity can be used to convert glucuronic into glucaric acid. Polypeptides having aldehyde oxidase activity as well as nucleic acid encoding such polypeptides can be obtained from various species including, without limitation, *Oryza sativa* (gi:1844950 or AAL700116.1), *Zea mays* (BAA23226.1), and *Lycopersicon esculentum* (AAG22607.1 or AF258810).

6. Nucleic Acid

The invention provides isolated nucleic acid molecules that contain a nucleic acid sequence at least about 50 percent identical (e.g., at least about 55, 65, 70, 75, 80, 85, 90, 95, or 99 percent identical) to the sequence set forth in SEQ ID NO:1. The invention also provides isolated nucleic acid molecules that encode a polypeptide having an amino acid sequence at least about 50 percent identical (e.g., at least about 55, 65, 70, 75, 80, 85, 90, 95, or 99 percent identical) to the sequence set forth in SEQ ID NO:19.

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

The term "exogenous" as used herein with reference to nucleic acid and a particular cell refers to any nucleic acid that does not originate from that particular cell as found in nature. Thus, all non-naturally-occurring nucleic acid is considered to be exogenous to a cell once introduced into the cell. It is important to note that non-naturally-occurring nucleic acid can contain nucleic acid sequences or fragments of nucleic acid sequences that are found in nature provided the nucleic acid as a whole does not exist in nature. For example, a nucleic acid molecule containing a genomic DNA sequence within an expression vector is non-naturallyoccurring nucleic acid, and thus is exogenous to a cell once introduced into the cell, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid.

Nucleic acid that is naturally occurring can be exogenous to a particular cell. For example, an entire chromosome isolated from a cell of person X is an exogenous nucleic acid with respect to a cell of person Y once that chromosome is introduced into Y's cell.

The percent identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site or the United States government's National Center for Biotechnology Information web site. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\Bl2seq -i c:.backslash.seq1.txt -j c:.backslash.seq2.txt -p blastn -o c:.backslash.output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt-); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent identity is determined by dividing the number of matches by the length of the sequence set forth in the identified sequence (e.g., SEQ ID NO:1) followed by multiplying the resulting value by 100. For example, a nucleic acid sequence that has 711 matches when aligned with the sequence set forth in SEQ ID NO:1 is 75 percent identical to the sequence set forth in SEQ ID NO:1 (i.e., 711÷948*100=75).

It is noted that the percent identity value is rounded to the nearest tenth. For example, 78.11, 78.12, 78.13, and 78.14 is rounded down to 78.1, while 78.15, 78.16, 78.17, 78:18, and 78.19 is rounded up to 78.2. It also is noted that the length value will always be an integer.

The invention also provides isolated nucleic acid molecules that (1) encode a polypeptide having myo-inositol oxygenase activity and (2) hybridize, under hybridization conditions, to the sense or antisense strand of a nucleic acid having the sequence set forth in SEQ ID NO:1. The hybridization conditions can be moderately or highly stringent hybridization conditions.

For the purpose of this invention, moderately stringent hybridization conditions mean the hybridization is performed at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% dextran sulfate, and 1-15 ng/mL probe (about $5\times10^7$ cpm/µg), while the washes are performed at about 50° C. with a wash solution containing 2×SSC and 0.1% sodium dodecyl sulfate.

Highly stringent hybridization conditions mean the hybridization is performed at about 42° C. in a hybridization solution containing 25 mM $KPO_4$ (pH 7.4), 5×SSC, 5× Denhart's solution, 50 µg/mL denatured, sonicated salmon sperm DNA, 50% formamide, 10% dextran sulfate, and 1-15 ng/mL probe (about $5\times10^7$ cpm/µg), while the washes are performed at about 65° C. with a wash solution containing 0.2×SSC and 0.1% sodium dodecyl sulfate.

Isolated nucleic acid molecules within the scope of the invention can be obtained using any method including, without limitation, common molecular cloning and chemical nucleic acid synthesis techniques. For example, PCR can be used to obtain an isolated nucleic acid molecule containing a nucleic acid sequence sharing similarity to the sequence set forth in SEQ ID NO:1. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

Isolated nucleic acid molecules within the scope of the invention also can be obtained by mutagenesis. For example, an isolated nucleic acid containing a sequence set forth in SEQ ID NO:1 can be mutated using common molecular cloning techniques (e.g., site-directed mutagenesis). Possible mutations include, without limitation, deletions, insertions, and substitutions, as well as combinations of deletions, insertions, and substitutions.

In addition, nucleic acid and amino acid databases (e.g., Genank®) can be used to obtain an isolated nucleic acid molecule within the scope of the invention. For example, any nucleic acid sequence having some homology to a sequence set forth in SEQ ID NO:1, or any amino acid sequence having some homology to a sequence set forth in SEQ ID NO:19 can be used as a query to search GenBank®.

Further, nucleic acid hybridization techniques can be used to obtain an isolated nucleic acid molecule within the scope of the invention. Briefly, any nucleic acid molecule having some homology to a sequence set forth in SEQ ID NO:1 can be used as a probe to identify a similar nucleic acid by hybridization under conditions of moderate to high stringency. Once identified, the nucleic acid molecule then can be purified, sequenced, and analyzed to determine whether it is within the scope of the invention as described herein.

Hybridization can be done by Southern or Northern analysis to identify a DNA or RNA sequence, respectively, which hybridizes to a probe. The probe can be labeled with a biotin, digoxygenin, an enzyme, or a radioisotope such as $^{32}$P. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39-7.52 of Sambrook et al., (1989) Molecular Cloning, second edition, Cold Spring harbor Laboratory, Plainview, N.Y. Typically, a probe is at least about 20 nucleotides in length. For example, a probe corresponding to a 20-nucleotide sequence set forth in SEQ ID NO:1 can be used to identify an identical or similar nucleic acid. In addition, probes longer or shorter than 20 nucleotides can be used.

7. Genetically Modified Cells

The invention provides genetically modified cells (e.g., cells containing an exogenous nucleic acid molecule). Such cells can be used to produce an organic compound such as ascorbic acid, glucuronic acid, and glucaric acid. The cells can be eukaryotic or prokaryotic. For example, genetically modified cells of the invention can be mammalian cells (e.g., human, murine, and bovine cells), plant cells (e.g., corn, wheat, rice, and soybean cells), fungal cells (e.g., yeast cells), or bacterial cells (e.g., *E. coli* cells). A cell of the invention also can be a microorganism. The term "microorganism" as used herein refers to all microscopic organisms including, without limitation, bacteria, algae, fungi, and protozoa Thus, *E. coli, S. cerevisiae, Kluyveromyces lactis, A. niger, Cr. terreus, Sch. occidentalis*, and *Sz. pombe* are considered microorganisms.

Typically, a cell of the invention is genetically modified such that a particular organic compound is produced. Such cells can contain one or more exogenous nucleic acid molecules that encode polypeptides having enzymatic activity. For example, a microorganism can contain exogenous nucleic acid that encodes a polypeptide having myo-inositol oxygenase activity. In this case, D-myo-inositol can be converted into D-glucuronate which can lead to the production of ascorbic acid. It is noted that a cell can be given an exogenous nucleic acid molecule that encodes a polypeptide having an enzymatic activity that catalyzes the production of a compound not normally produced by that cell. Alternatively, a cell can be given an exogenous nucleic acid molecule that encodes a polypeptide having an enzymatic activity that catalyzes the production of a compound that is normally produced by that cell. In this case, the genetically modified cell can produce more of the compound, or can produce the compound more efficiently, than a similar cell not having the genetic modification.

A polypeptide having a particular enzymatic activity can be a polypeptide that is either naturally occurring or non-naturally occurring. A naturally occurring polypeptide is any polypeptide having an amino acid sequence as found in nature, including wild-type and polymorphic polypeptides. Such naturally occurring polypeptides can be obtained from any species including, without limitation, mammalian, fugal, and bacterial species. A non-naturally occurring polypeptide is any polypeptide having an amino acid sequence that is not found in nature. Thus, a non-naturally occurring polypeptide can be a mutated version of a naturally occurring polypeptide or an engineered polypeptide. For example, a non-naturally occurring polypeptide having myo-inositol oxygenase activity can be a mutated version of a naturally occurring polypeptide having myo-inositol oxygenase activity that retains at least some myo-inositol oxygenase activity. A polypeptide can be mutated by, for example, sequence additions, deletions, and/or substitutions using standard methods such as site-directed mutagenesis of the corresponding nucleic acid coding sequence.

The invention provides genetically modified cells that can be used to perform one or more steps of a metabolic pathway described herein. For example, an individual microorganism can contain an exogenous nucleic acid molecule such that each of the polypeptides necessary to perform all seven steps of a seven step metabolic pathway is expressed. It is important to note that such cells can contain any number of exogenous nucleic acid molecules. For example, a particular cell can contain seven exogenous nucleic acid molecules with each one encoding one of the seven polypeptides necessary to perform a seven step metabolic pathway, or a particular cell can endogenously produce polypeptides necessary to perform the first six of the seven steps of a seven step metabolic pathway while containing an exogenous nucleic acid molecule that encodes a polypeptide necessary to perform the seventh step. It is noted that a cell containing an exogenous nucleic acid molecule that encodes a polypeptide having a particular activity can also endogenously express a polypeptide having a similar activity. In such cases, providing a cell with an exogenous nucleic acid molecule that encodes a polypeptide having an activity similar to an endogenously expressed polypeptide is expected to provide that cell with enhanced activity as compared to a similar cell lacking the exogenous nucleic acid molecule. It also is noted that a cell can contain an exogenous nucleic acid molecule that encodes a polypeptide having pyridine nucleotide transhydrogenase activity. Such a polypeptide can be used to generate NADPH within a cell by catalyzing a chemical reaction (e.g., NADH+ NADP→NAD+NADPH). Any source can be used to obtain a polypeptide having pyridine nucleotide transhydrogenase activity or a nucleic acid encoding such a polypeptide. For example, nucleic acid encoding a polypeptide having pyridine nucleotide transhydrogenase activity can be obtained as described elsewhere (e.g., U.S. Pat. No. 5,830,716 and Nissen et al., *Yeast* 18:19-32 (2001)).

In addition, a single exogenous nucleic acid molecule can encode one or more than one polypeptide. For example, a single exogenous nucleic acid molecule can contain sequences that encode three different polypeptides. Further, the cells described herein can contain a single copy, or multiple copies (e.g., about 5, 10, 20, 35, 50, 75, 100 or 150 copies), of a particular exogenous nucleic acid molecule. For example, a particular cell can contain about 50 copies of an exogenous nucleic acid molecule X. Again, the cells described herein can contain more than one particular exogenous nucleic acid molecule. For example, a particular cell can contain about 50 copies of exogenous nucleic acid molecule X as well as about 75 copies of exogenous nucleic acid molecule Y.

In one embodiment, the invention provides a cell containing an exogenous nucleic acid molecule that encodes a polypeptide having enzymatic activity that leads to the formation of ascorbic acid. It is noted that the produced ascorbic acid can be secreted from the cell, eliminating the need to disrupt cell membranes to retrieve the organic compound. Typically, the cell of the invention produces the organic compound with the concentration being at least about 0.1 grams per L (e.g., at least about 1 g/L, 5 g/L, 10 g/L, or 80 g/L). When determining the yield of organic compound production for a particular cell, any method can be used. See, e.g., Kiers et al., *Yeast*, 14(5):459-469 (1998). Typically, a cell within the scope of the invention such as a microorganism catabolizes a hexose carbon source such as glucose. A cell, however, can catabolize a variety of carbon sources such as pentose sugars (e.g., ribose, arabinose, xylose, and lyxose), glycerols, or myo-inositol. In other words, a cell within the scope of the invention can utilize a variety of carbon sources.

In another embodiment, a cell within the scope of the invention can contain an exogenous nucleic acid molecule that encodes a polypeptide having myo-inositol oxygenase activity. Such cells can have any level of myo-inositol oxygenase activity. For example, a cell containing an exogenous nucleic acid molecule that encodes a polypeptide having myo-inositol oxygenase activity can have myo-inositol oxygenase activity with a specific activity greater than about 5 mg glucuronic acid formed per gram dry cell weight per hour (e.g., greater than about 10, 20, 30, 40, 50, 60, 70, 80, 90, 100, 125, 150, 200, 250, 300, 350, 400, 500, or more mg glucuronic acid formed per gram dry cell weight per hour). Alternatively, a cell can have myo-inositol oxygenase activity such that a cell extract from $1 \times 10^6$ cells has a specific activity greater than about 5 µg glucuronic acid formed per 10 mg total protein per 10 minutes (e.g., greater than about 10, 20, 30, 40, 50, 60, 70, 80, 90, 100, 125, 150, 200, 250, 300, 350, 400, 500, or more µg glucuronic acid formed per 10 mg total protein per 10 minutes).

A nucleic acid molecule encoding a polypeptide having enzymatic activity can be identified and obtained using any method. For example, standard nucleic acid sequencing techniques and software programs that translate nucleic acid sequences into amino acid sequences based on the genetic code can be used to determine whether or not a particular nucleic acid has any sequence homology with known enzymatic polypeptides. Sequence alignment software such as MEGALIGN® (DNASTAR, Madison, Wis., 1997) can be used to compare various sequences. In addition, nucleic acid molecules encoding known enzymatic polypeptides can be mutated using common molecular cloning techniques (e.g., site-directed mutageneses). Possible mutations include, without limitation, deletions, insertions, and base substitutions, as well as combinations of deletions, insertions, and base substitutions. Further, nucleic acid and amino acid databases (e.g., Genank®) can be used to identify a nucleic acid sequence that encodes a polypeptide having enzymatic activity. Briefly, any amino acid sequence having some homology to a polypeptide having enzymatic activity, or any nucleic acid sequence having some homology to a sequence encoding a polypeptide having enzymatic activity can be used as a query to search GenBank®. The identified polypeptides then can be analyzed to determine whether or not they exhibit enzymatic activity.

Nucleic acid molecules that encode a polypeptide having enzymatic activity can be identified and obtained using common molecular cloning or chemical nucleic acid synthesis procedures and techniques, including PCR. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

In addition, nucleic acid hybridization techniques can be used to identify and obtain a nucleic acid molecule that encodes a polypeptide having enzymatic activity. Briefly, any nucleic acid molecule that encodes a known enzymatic polypeptide, or fragment thereof, can be used as a probe to identify a similar nucleic acid molecules by hybridization under conditions of moderate to high stringency. Such similar nucleic acid molecules then can be isolated, sequenced, and analyzed to determine whether the encoded polypeptide has enzymatic activity.

Hybridization can be done by Southern or Northern analysis to identify a DNA or RNA sequence, respectively, that hybridizes to a probe. The probe can be labeled with a radioisotope such as $^{32}P$, an enzyme, digoxygenin, or by biotinylation. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39-7.52 of Sambrook et al., (1989) Molecular Cloning, second edition, Cold Spring harbor Laboratory, Plainview, N.Y. Typically, a probe is at least about 20 nucleotides in length. For example, a probe corresponding to a 20 nucleotide sequence that encodes a mammalian myo-inositol oxygenase can be used to identify a nucleic acid molecule that encodes a fungal polypeptide having myo-inositol oxygenase activity. In addition, probes longer or shorter than 20 nucleotides can be used.

Expression cloning techniques also can be used to identify and obtain a nucleic acid molecule that encodes a polypeptide having enzymatic activity. For example, a substrate known to interact with a particular enzymatic polypeptide can be used to screen a phage display library containing that enzymatic polypeptide. Phage display libraries can be generated as described elsewhere (Burritt et al., *Anal. Biochem.* 238:1-13 (1990)), or can be obtained from commercial suppliers such as Novagen (Madison, Wis.).

Further, polypeptide sequencing techniques can be used to identify and obtain a nucleic acid molecule that encodes a polypeptide having enzymatic activity. For example, a purified polypeptide can be separated by gel electrophoresis, and its amino acid sequence determined by, for example, amino acid microsequencing techniques. Once determined, the amino acid sequence can be used to design degenerate oligonucleotide primers. Degenerate oligonucleotide primers can be used to obtain the nucleic acid encoding the polypeptide by PCR Once obtained, the nucleic acid can be sequenced, cloned into an appropriate expression vector, and introduced into a microorganism.

Any method can be used to introduce an exogenous nucleic acid molecule into a cell. In fact, many methods for introducing nucleic acid into microorganisms such as bacteria and yeast are well known to those skilled in the art. For example, heat shock, lipofection, electroporation, conjugation, fusion of protoplasts, and biolistic delivery are common methods for introducing nucleic acid into bacteria and yeast cells. See, e.g., Ito et al., *J. Bacterol.* 153:163-168 (1983); Durrens et al., *Curr. Genet.* 18:7-12 (1990); and Becker and Guarente, *Methods in Enzymology* 194:182-187 (1991).

An exogenous nucleic acid molecule contained within a particular cell of the invention can be maintained within that cell in any form. For example, exogenous nucleic acid molecules can be integrated into the genome of the cell or maintained in an episomal state. In other words, a cell of the invention can be a stable or transient transformant. In addition, a microorganism described herein can contain a single copy, or multiple copies (e.g., about 5, 10, 20, 35, 50, 75, 100 or 150 copies), of a particular exogenous nucleic acid molecule as described above.

Methods for expressing an amino acid sequence from an exogenous nucleic acid molecule are well known to those skilled in the art. Such methods include, without limitation, constructing a nucleic acid such that a regulatory element promotes the expression of a nucleic acid sequence that encodes a polypeptide. Typically, regulatory elements are DNA sequences that regulate the expression of other DNA sequences at the level of transcription. Thus, regulatory elements include, without limitation, promoters, enhancers, and the like. Any type of promoter can be used to express an amino acid sequence from an exogenous nucleic acid molecule. Examples of promoters include, without limitation, constitutive promoters, tissue-specific promoters, and promoters responsive or unresponsive to a particular stimulus (e.g., light, oxygen, chemical concentration, and the like). For example, a promoter that is unresponsive to lactose can be used to express a polypeptide having myo-inositol oxygenase activity. Moreover, methods for expressing a polypeptide from an exogenous nucleic acid molecule in cells such as bacterial cells and yeast cells are well known to those skilled in the art. For example, nucleic acid constructs that are capable of expressing exogenous polypeptides within *E. coli* are well known. See, e.g., Sambrook et al., Molecular cloning: a laboratory manual, Cold Spring Harbour Laboratory Press, New York, USA, second edition (1989).

As described herein, a cell within the scope of the invention can contain an exogenous nucleic acid molecule that encodes a polypeptide having enzymatic activity that leads to the formation of ascorbic acid. Methods of identifying cells that contain exogenous nucleic acid are well known to those skilled in the art. Such methods include, without limitation, PCR and nucleic acid hybridization techniques such as Northern and Southern analysis. In some cases, immunohistochemistry and biochemical techniques can be used to determine if a cell contains a particular nucleic acid by detecting the expression of the encoded enzymatic polypeptide encoded by that particular nucleic acid molecule. For example, an antibody having specificity for an encoded enzyme can be used to determine whether or not a particular cell contains that encoded enzyme. Further, biochemical techniques can be used to determine if a cell contains a particular nucleic acid molecule encoding an enzymatic polypeptide by detecting an organic product produced as a result of the expression of the enzymatic polypeptide. For example, detection of ascorbic acid after introduction of exogenous nucleic acid that encodes a polypeptide having L-gulono-γ-lactone oxidase activity into a cell that does not normally express such a polypeptide can indicate that that cell not only contains the introduced exogenous nucleic acid molecule but also expresses the encoded enzymatic polypeptide from that introduced exogenous nucleic acid molecule. Methods for detecting specific enzymatic activities or the presence of particular organic products are well known to those skilled in the art. For example, the presence of ascorbic acid can be determined as described elsewhere. See, Sullivan and Clarke, *J. Assoc. Offic. Agr. Chemists*, 38:514-518 (1955).

The invention also provides genetically modified cells having reduced polypeptide activity. The term "reduced" as used herein with respect to a cell and a particular polypeptide's activity refers to a lower level of activity than that measured in a comparable cell of the same species. For example, a particular microorganism lacking enzymatic activity X is considered to have reduced enzymatic activity X if a comparable microorganism has at least some enzymatic activity X. It is noted that a cell can have the activity of any type of polypeptide reduced including, without limitation, enzymes, transcription factors, transporters, receptors, signal molecules, and the like. For example, a cell can contain an exogenous nucleic acid molecule that disrupts a regulatory and/or coding sequence of a polypeptide having myo-inositol oxygenase activity. Disrupting myo-inositol oxygenase expression can lead to the accumulation of D-myo-inositol or derivatives. It is also noted that reduced polypeptide activities can be the result of lower polypeptide concentration, lower specific activity of a polypeptide, or combinations thereof. Many different methods can be used to make a cell having reduced polypeptide activity. For example, a cell can be engineered to have a disrupted regulatory sequence or polypeptide-encoding sequence using common mutagenesis or knock-out technology. See, e.g., Methods in Yeast Genetics (1997 edition), Adams, Gottschling, Kaiser, and Sterns, Cold Spring Harbor Press (1998). Alternatively, antisense technology can be used to reduce the activity of a particular polypeptide. For example, a cell can be engineered to contain a cDNA that encodes an antisense molecule that prevents a polypeptide from being translated. The term "antisense molecule" as used herein encompasses any nucleic acid molecule or nucleic acid analog (e.g., peptide nucleic acids) that contains a sequence that corresponds to the coding strand of an endogenous polypeptide. An antisense molecule also can have flanking sequences (e.g., regulatory sequences). Thus, antisense molecules can be ribozymes or antisense oligonucleotides. A ribozyme can have any general structure including, without limitation, hairpin, hammerhead, or axhead structures, provided the molecule cleaves RNA.

A cell having reduced activity of a polypeptide can be identified using any method. For example, biological assays such as the assay described in Example 3 for measuring myo-inositol oxygenase activity can be used to identify cells having reduced myo-inositol oxygenase activity.

In one embodiment, the invention provides microorganisms that contain reduced myo-inositol transporter activity. Microorganisms containing reduced myo-inositol transporter activity can produce inositol and inositol-related products (e.g., myo-inositol, meso-inositol, hexahydroxycyclohexane, and Vitamin $B_8$) in the presence of inositol. In other words, inositol-1-phosphate synthase activity (EC 5.5.1.4) is not regulated by inositol in microorganisms lacking myo-inositol transporter activity. In general, such microorganisms can be produced by reducing the activity of itr1, itr2, opi1, or similar polypeptides. Again, microorganisms containing reduced myo-inositol transporter activity can be produced by any method including, without limitation, mutagenesis, knock-out, and anti-sense technology. It is noted that nucleic acid that encodes itr1 from *S. cerevisiae* is set forth in GenBank® Accession Number D90352, and nucleic acid that encodes itr2 from *S. cerevisiae* is set forth in GenBank® Accession Number D90353.

In another embodiment, the invention provides cells that can have the ability, or the enhanced ability, to transport or produce substrates. These cells can have nucleic acid sequences that encode polypetides with transporter activity (e.g., itr1 from *S. cerevisiae*) and/or inositol-1-phophate synthase activity as described herein.

In another embodiment, the invention provides cells having reduced L-gulonate 3-dehydrogenase activity (E.C. 1.1.1.45). Such cells also can contain a polypeptide having phytase activity, a polypeptide having phosphatase activity (or a mixture of polypeptides having different phosphatase activities), and/or a mixture of polypeptides having phytase activity and polypeptides having phosphatase activity (or polypeptides having different phosphatase activities). In addition, such cells can contain exogenous nucleic acid molecules that encode a polypeptide having phytase activity, a polypeptide having phosphatase activity (or a mixture of polypeptides having different phosphatase activities), and/or a mixture of polypeptides having phytase activity and polypeptides having phosphatase activity (or polypeptides having different phosphatase activities). For example, a cell can contain polypeptides having multiple inositol polyphosphate phosphatase activities or exogenous nucleic acid molecules that encode polypeptides having multiple inositol polyphosphate phosphatase activities. Cells having phytase activity, phosphatase activity, and/or mixtures thereof as well as reduced L-gulonate 3-dehydrogenase activity can be used to produce increased levels of myo-inositol from phytic acid.

8. Organic Compound Production and Culturing Methods

The invention provides methods for producing an organic compound. For example, the methods and materials described herein can be used to produce D-glucose, D-glucose-1-phosphate, D-glucose-6-phosphate, UDP-D-glucose, D-myo-inositol, D-myo-inositol-1-phosphate, D-glucuronate, D-glucuronate-1-phosphate, UDP-D-glucuronate, D-glucurono-3,6-lactone, L-gulonate, L-gulono-γ-lactone, glucaric acid, and L-ascorbate. Other examples of compounds that can be produced include, without limitation, L-dehydroascorbate, L-threonate, and 3-dehydro-L-threonate. It is noted that a produced compound can be in the D or L configuration. In addition, a polypeptide having a particular enzymatic activity can be used such that the desired organic compound is optically pure (e.g., about 75, 80, 85, 90, 95, 99, or 99.9 percent pure).

A cell described herein can be used to produce a particular organic compound such as myo-inositol, ascorbic acid, or glucaric acid. For example, a microorganism containing all the polypeptides necessary to produce ascorbic acid from glucose as depicted in FIG. 1 can be used to produce ascorbic acid. Alternatively, different microorganisms can be used to produce a particular, organic compound. For example, three different microorganisms each containing a different set of polypeptides necessary to produce ascorbic acid from glucose can be used to produce ascorbic acid. In other words, one or more than one group of cells can be used to produce a particular organic compound.

In addition, purified polypeptides having enzymatic activity can be used alone or in combination with cells to produce organic compounds. For example, with reference to FIG. 1, a microorganism containing polypeptides necessary to catalyze steps one through six can be used to produce L-gulono-γ-lactone from glucose, while a purified polypeptide having gulono-γ-lactone oxidase activity (EC 1.1.3.8) can be used to convert L-gulono-γ-lactone into L-ascorbate. Any method can be used to purify a particular polypeptide. For example, size fractionation, ion exchange, HPLC, and affinity chromatography can be used to purify a polypeptide having enzymatic activity. In addition, purified polypeptides can be used on a solid support (e.g., glass beads, polymer structures, and other plastics), or in solution.

Further, cell free extracts containing a polypeptide having enzymatic activity can be used alone or in combination with purified polypeptides and/or cells to produce organic compounds. For example, with reference to FIG. 1, a microorganism containing polypeptides necessary to catalyze steps one through five can be used to produce L-gulonate from glucose, while a cell-free extract containing a polypeptide having 1,4-lactone hydroxyacylhydrolase activity (EC 3.1.1.25) is used to convert L-gulonate into L-gulono-γ-lactone, and a purified polypeptide having gulono-γ-lactone oxidase activity (EC 1.1.3.8) is used to convert L-gulono-γ-lactone into L-ascorbate. Any method can be used to produce a cell-free extract For example, French pressure cell disruption, enzymatic lysis, mechanical shearing (with, for example, glass beads), osmotic shock, sonication, and/or a repeated freeze-thaw cycle followed by filtration and/or centrifugation can be used to produce a cell-free extract from intact cells.

It is noted that a cell, purified polypeptide, and/or cell-free extract can be used to produce a particular organic compound that is, in turn, treated chemically to produce another organic compound. For example, a microorganism can be used to produce L-gulono-γ-lactone, while a chemical process is used to convert L-gulono-γ-lactone into L-ascorbate. Such chemical processes include, without limitation, treatment with benzaldehyde-hydrogen chloride, oxidation with manganese dioxide, and hydrolysis with 70 percent acetic acid-water (Crawford and Crawford, *Adv. in Carbohydrate Chem. Biochem.*, 37:79-155 (1980)). Likewise, a chemical process can be used to produce a particular organic compound that is, in turn, converted into another organic compound using a microorganism, purified polypeptide, and/or cell-free extract described herein. For example, a chemical process can be used to produce L-gulono-γ-lactone, while a microorganism is used to convert L-gulono-γ-lactone into L-ascorbate.

Typically, a particular organic compound is produced by providing cells and culturing the provided cells with culture medium such that that organic compound is produced. In general, the culture media and/or culture conditions can be such that the cells grow to an adequate density and produce the desired compound efficiently.

For large-scale production processes, the following methods can be used. First, a large tank (e.g., a 50-, 100-, 200-, or more gallon tank) containing appropriate culture medium with, for example, hexose and/or pentose carbons is inoculated with a culture of a particular cell. After inoculation, the cells are incubated to allow the production of biomass. Once a sufficient biomass is reached, the broth containing the cells can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank. For example, the first tank can contain medium with xylose and arabinose, while the second tank contains medium with glucose.

Once transferred, the cells are incubated to allow for the production of the desired organic compound. Once produced, any method can be used to isolate the desired compound. For example, common separation techniques can be used to remove the biomass from the broth, and common isolation procedures (e.g., extraction, distillation, and ion-exchange procedures) can be used to obtain the organic compound from the cell-free broth. In addition, the desired organic compound can be isolated while it is being produced, or it can be isolated from the broth after the product production phase has been terminated.

It will be appreciated that the methods and materials described herein can be adapted and used in any type of culturing process including, without limitation, the processes commonly referred to as "continuous fermentation" and "batch fermentation" processes. In addition, the cells used during one production process can be recovered and reused in subsequent production processes. For example, the cells can be reused multiple times to produce a desired organic compound. Further, any carbon source can be used. For example, allose, altrose, glucose, mannose, gulose, iodose, galactose, talose, melibiose, phytic acid, sucrose, fructose, raffinose, stachyose, ribose, arabinose, xylose, lyxose, glycerol, inositol, carbon combinations such as inositol and glucose, starches such as molasses, corn starch, and wheat starch, and hydrolysates such as corn fiber hydrolysates and other cellulosic hydrolysates can be used as a carbon source for producing either biomass or the desired organic compound. Moreover, any medium can be used. For example, standard culture media (e.g., yeast minimal medium and YP medium (yeast extract 10 g/L, peptone broth 20 g/L)) as well as media such as corn steep water and corn steep liquor can be used.

Phytic acid can be converted into myo-inositol, which is then converted into ascorbic acid as described herein. Any method can be used to produce ascorbic acid from phytic acid. For example, chemical methods can be used to convert phytic acid into myo-inositol, while enzymatic methods are used to convert myo-inositol into ascorbic acid. Any material containing phytic acid such as corn steep liquor can be used as a source material. In addition, phytic acid can be used in a pure or unpure form. In one embodiment, phytate is purified from a solution such as corn steep liquor and converted into inositol by chemical hydrolysis. In this case, the resulting inositol can be enzymatically converted into ascorbic acid.

Any method can be used to purify phytate from a solution. For example, calcium phytate can be recovered from materials such as corn steep liquor, heavy steep water, or light steep water by treating the liquid medium with a calcium compound such as calcium hydroxide (e.g., a 15 percent solution of calcium hydroxide). After treatment, the pH can be adjusted to about 6.0. Once formed, the calcium phytate product can be washed with warm water (e.g., 50° C. water) and filtered to remove impurities. This process can yield insoluble calcium phytate that can be further converted to inositol.

Alternatively, a solution containing phytate can be treated with an ion exchange resin such as that described in U.S. Pat. No. 4,668,813. After adsorbtion of the phytate to the resin, the resin can be washed with warm water (e.g., 30° C. to 85° C. water), and the phytate eluted as a salt by treating the bound resin with a solution such as aqueous sodium hydroxide, potassium hydroxide, ammonium hydroxide, or the like. Another method that can be used to isolate phytic acid involves separating phytate from steep water as described in U.S. Pat. No. 3,410,929. Briefly, steep water can be passed over a resin such as Dow Chemical Company Retardation 11 A8 resin. After passage of the steep water, the resin can be washed with water, and the phytate desorbed from the resin by washing with a NaCl solution.

Any method can be used to convert phytic acid into inositol. For example, inositol can be made from phytic acid by treating phytic acid in water at 100° C. as described elsewhere (Cosgrove, D. J. "Inositol Phosphates" Elsevier, Amsterdam, 1980, p. 36). Alternatively, inositol can be derived from phytate by steam treatment as described elsewhere (e.g., U.S. Pat. No. 4,668,813) or by enzymatic treatment as described elsewhere (e.g., U.S. Pat. No. 5,830,732). In addition, a combination of enzymatic activities can be used to convert phytic acid into inositol. For example, phytase enzymes can be used to convert phytic acid into inositol mono-phosphate, and an acid phosphatase can be used to convert the resulting inositol monophosphate into inositol.

Ascorbic acid can be produced from phytate or inositol using the methods and materials described herein. For example, a cell (e.g., *Saccharomyces cerevisiae*) expressing polypeptides having (1) phytase activity capable of converting phytate into inositol or phytase and acid phosphatase activities, (2) myo-inositol oxygenase activity, (3) glucuronate reductase activity, (4) uronolactonase activity, 1,4-lactone hydroxyacylhydrolase activity, or D-glucono-1,5-lactone lactonohydrolase activity, and (5) gulono-γ-lactone oxidase activity, gulono-γ-lactone dehydrogenase activity, or galactono-γ-lactone oxidase activity can be used to convert phytate into ascorbic acid by culturing the microorganism with media containing a high percentage of, for example, corn steep liquor (e.g., a media with 50, 60, 70, 80, 90, 95, or more percent corn steep liquor). Such a media can contain corn steep liquor (10 g/L, dry basis), ammonium sulfate (3 g/L), biotin (0.1 g/L), and glucose (20 g/L). Alternatively, a cell containing polypeptides having myo-inositol oxygenase, glucuronate reductase, uronolactonase, and gulono-γ-lactone oxidase can be used to produce ascorbic acid from inositol. Once produced, any method can be used to purify the resulting ascorbic acid. For example, the methods and materials described in U.S. Pat. No. 6,037,480 or 6,169,187 can be used to purify ascorbic acid from a fermentation broth. Alternatively, the unpurified ascorbic acid can be used directly as a feed supplement.

9. Modifying Plants and Plant Cells

The invention provides methods and materials related to the use of plants and plant cells to produce (1) a polypeptide having myo-inositol oxygenase activity, (2) myo-inositol, and/or (3) ascorbic acid. Expression vectors and methods of transforming plant cells are provided herein. These vectors can be designed such that a transgene encoding a polypeptide having myo-inositol oxygenase activity is overexpressed in a transgenic plant and/or plant cell. In one embodiment, the plant or plant cell can be used to produce a polypeptide having myo-inositol oxygenase activity, which in turn can be purified and used in in vitro applications such as in the production of ascorbic acid.

Plant cells and/or transgenic plants also can be generated as described herein such that the resulting plant cells and/or transgenic plants have increased or decreased responses to environmental stresses. For example, transgenic plant cells or plants can display an increased or decreased salt tolerance (Nelson et al., *Plant Physiology*, 119:165-172 (1999); and Nelson, *The Plant Cell* 10:753-764 (1998)). The modulation of inositol concentrations also can be useful for altering seed development (Yoshida et al. *Plant Physiology* 119:65-72 (1999)). The expression of a polypeptide having myo-inositol oxygenase activity can be increased in a plant cell and/or a transgenic plant by transforming the plant with a construct that contains a nucleic acid sequence that encodes a polypeptide having myo-inositol oxygenase activity operably linked to a promoter. Similarly, myo-inositol oxygenase activity can be reduced by transforming a plant or plant cell with a construct that contains an antisense or sense sequence (Napoli et al., *The Plant Cell* 2:279-289 (1990) and U.S. Pat. No. 5,034,323) which causes the down regulation of endogenous myo-inositol oxygenase expression. Constructs that either up-regulate myo-inositol oxygenase expression or down-regulate myo-inositol oxygenase expression are herein after termed modulating constructs.

Once a nucleic acid sequence encoding a polypeptide having myo-inositol oxygenase activity has been produced, standard techniques can be used to express the sequence in transgenic plants. The basic approach is to clone the nucleic acid sequence into a transformation vector such that it is operably linked to one or more control sequences (e.g., a promoter) that direct expression of the nucleic acid sequence in plant cells. The transformation vector is then introduced into plant cells by one of a number of techniques (e.g., biolistics), whole plants are regenerated from the cells, and progeny plants containing the introduced nucleic acid sequence are selected. All or part of the transformation vector can be stably integrated into the genome of the plant cell. That part of the transformation vector which integrates into the plant cell and which contains the introduced sequence and associated sequences for controlling expression (the introduced ("transgene") may be referred to as the recombinant expression cassette.

Selection of progeny plants containing the introduced transgene can be made based upon the detection of an altered phenotype. Such a phenotype may be enhanced resistance to a chemical agent (such as an antibiotic) as a result of the inclusion of a dominant selectable marker gene incorporated into the transformation vector.

Successful examples of the modification of plant characteristics by transformation with cloned nucleic acid sequences are replete in the technical and scientific literature. Selected examples, which serve to illustrate the klowledge in this field of technology include U.S Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369; and 5,610,042. These examples include descriptions of transformation vector selection, transformation techniques, and the construction of constructs designed to over-express the introduced transgene.

The modulating construct can be introduced into a wide variety of plant species. These plants can be monocots, dicots, or gymnosperms. Thus, for example, a nucleic acid encoding a polypeptide having myo-inositol oxygenase activity can be introduced into plant species including, without limitation, maize, wheat, rice, barley, soybean, cotton, beans in general, rape/canola, alfalfa, flax, sunflower, safflower, brassica, cotton, tobacco, flax, peanut, clover, cowpea, grapes; vegetables such as lettuce, tomato, cucurbits, cassava, potato, carrot, radish, pea, lentils, cabbage, cauliflower, broccoli, Brussels sprouts, peppers; tree fruits such as citrus, apples, pears, peaches, apricots, walnuts; fir trees such as Douglas fir and loblolly pine, and flowers such as carnations and roses.

A number of recombinant vectors suitable for stable transfection of plant cells or for the establishment of transgenic plants have been described including those described in Pouwels et al. (*Cloning Vectors; A Laboratory Manual*, 1985, supp., 1987); Weissbach and Weissbach (*Methods for Plant Molecular Biology*, Academic Press, 5:173-184, 1989); and Gelvin et al. (*Plant Molecular Biology Manual*, Kluwer Academic Publishers, 1990). Typically, plant transformation vectors include one or more cloned sequences under the transcriptional control of 5' and 3' regulatory sequences and a dominant selectable marker. Such plant transformation vectors typically also contain a promoter regulatory region (e.g., a regulatory region controlling inducible or constitutive, environmentally- or developmentally-regulated, or cell- or tissue-specific expression), a transcription initiation start site, a ribosome binding site, and RNA processing signal, a transcription termination site, and/or a polyadenylation signal. Examples of constitutive plant promoters that can be used for expressing a transgene include: the cauliflower mosaic virus (CaMV) 35S promoter, which confers constitutive, high-level expression in most plant tissues (See, e.g., Odel et al., *Nature*, 313:810 (1985); Dekeyser et al., *Plant Cell*, 2:591 (1990); Terada and Shimanoto, *Mol. Gen. Genet.* 220;389 (1990); and Benfey and Chua, *Science*, 250:959-966 (1990)); the nopaline synthase promoter (An et al., *Plant Physiol.* 88:547 (1988)); the octopine synthase promoter (Fromm et al., *Plant Cell*, 1:977 (1989)); and the 2× CaMN/35S promoter with a translation enhance sequence (Kay et al., *Science*, 236:1299-1302 (1987)).

A variety of plant gene promoters that are regulated in response to environmental, hormonal, chemical, and/or developmental signals also can be used for expression of transgene in plant cells, including promoters regulated by: (a) heat (Callis et al., *Plant Physiol.*, 88:965 (1988); Ainley et al., *Plant Mol. Biol.*, 22:13-23 (1993); and Gilmartin et al., The *Plant Cell.*, 4:839-949 (1992)); (b) light (e.g., the pea rbcS-3A promoter, Kuhlemeier et al., *Plant Cell*, 1:471 (1989), and the maize rbcS promoter, Schaffner & Sheen, *Plant Cell*, 3:997 (1991)); (c) hormones, such as abscisic acid (Marcotte et al., *Plant Cell*, 1:471 (1989)); (d) wounding (e.g., the potato PinII promoter (Keil et al., *Nucl. Acids. Res.* 14:5641-5650 (1986)), the *Agrobacterium* mas promoter (Langridge et al., *Bio/Technology* 10:305-308 (1989)), and the grapevine vst1 promoter (Weise et al., *Plant Mol. Biol.*, 26:667-677 (1994)); and (e) chemicals such as methyl jasmonate or salicylic acid (Gatz et al. *Plant Mol. Biol.* 48:89-108 (1997)).

Alternatively, tissue specific (root, leaf, flower, and seed for example) promoters (Carpenter et al., *The Plant Cell* 4:557-571 (1992); Denis at al., *Plant Physiol* 101:1295-1304 (1993); Opperman et al., *Science* 263:221-223 (1993); Stockhause et al., *The Plant Cell* 9:479-489 (1997); Roshal et al., *The EMBO J.* 6:1155 (1987); Schernathaner et al., *EMBO J.* 7:1249 (1988); Yamamoto et al., *Plant Cell* 3:371-382 (1990); and Bustos et al., *Plant Cell* 1:839 (1989)) can be fused to the coding sequence to obtain particular expression in respective organs.

Plant transformation vectors also can include RNA processing signals (e.g., introns) that can be positioned upstream or downstream of the ORE sequence in the transgene. In addition, the expression vectors also can include additional regulatory sequences from the 3'-untranslated region of plant genes, e.g., a 3' terminator region to increase mRNA stability of the mRNA, such as the PI-II terminator region of potato or the octopine of noplaine synthase (NOS) 3' terminator regions.

Plant transformation vectors also can include dominant selectable marker genes to allow for the ready selection of transformants. Such genes include those encoding antibiotic resistance genes (e.g., resistance to hygromycin, kanamycin, bleomycin, G418, streptomycin, or spectinomycin) and herbicide resistance genes (e.g., phosphinothricin acetyltransferase).

Transformation and regeneration of both monocotyledonous and dicotyledonous plant cells is now routine, and the appropriate transformation technique can be determined by the practitioner. The choice of method will vary with the type of plant to be transformed; those skilled in the art will recognize the suitability of particular methods for given plant types. Suitable methods can include, without limitation, electroporation of plant protoplasts, lipsome-mediated transformation, polyethylene glycol (PEG) mediated transformation, transformation using viruses, micro-injection of plant cells, micro-projectile bombardment of plant cells, vacuum infiltration, and *Agrobacteruim tumefaciens* (AT) mediated transformation. Typical procedures for transforming and regenerating plants are described in the patents referenced above.

Following transformation and regeneration of plants with the transformation vector, transformed plants are usually selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

10. Therapeutic Uses

Polypeptides having myo-inositol oxygenase activity can convert myo-inositol into glucuronic acid in many eukaryotic organisms, including plants, mammals (e.g., humans), and yeast. This enzyme activity has been found to be abnormal in kidneys from diabetic animals, and excessive amounts of inositol is secreted in the urine. Abnormal inositol levels are also associated with a number of other clinical abnormalities (Table I).

TABLE I

| Condition | Affected Tissue | Causative Agent(s) |
| --- | --- | --- |
| Cataract | eye lens | Low levels of inositol, which is an antioxidant and scavenges excess glucose (diabetes side effect) |
| Adipocyte malfunction | Adipocyte cells | Incorrect levels of inositol which is important in membranes and signal transduction pathways |
| Increased platelet aggregation/secretion | Platelet cells | Increased uptake/levels of myo-inositol and inositol phosphates (diabetes side effect) |
| Hepatic encephalopathy; Protacaval shunts; Alzheimer's | Brain | Myo-inositol depletion in neurochemical pathways |
| Nerve conduction | Peripheral nerves | Motor nerve conduction velocity impaired by low inositol levels (diabetes side effect) |
| Vascular disease | Endothelial cells, neuroblastoma | Decreased myo-inositol metabolism, decreased inositol uptake (diabetes side effect) |
| Dysmorphogenesis; Growth retardation | Mammals | Reduced myo-inositol levels (diabetes side effect) |

TABLE I-continued

| Condition | Affected Tissue | Causative Agent(s) |
| --- | --- | --- |
| Immune response | B/T lymphocytes | Incorrect inositol levels |
| Ataxia telangiectasia | Fibroblasts | Autosomal recessive disorder, accompanied by alteration in myo-inositol metabolism |
| Renal Failure | Kidney | Infection, trauma, etc. |

The identification of a polypeptide having myo-inositol oxygenase activity allows for the use of the enzyme and, variants thereof, in therapeutic applications in which abnormal levels of inositol are detected (see above). Abnormal inositol levels are characterized as levels of inositol that fall outside of range of inositol levels that would be expected from a control group. Abnormal inositol levels could be either greater than or less than those displayed by a control group. In many cases the control group can be a random sampling from a normal healthy population (i.e. a population that does not display outward manifestations of a disease that is suspected of being associated with abnormal inositol levels).

As described herein, antisense technology and myo-inositol oxygenase binding agents can be used to reduce myo-inositol oxygenase activity, and nucleic acid encoding a polypeptide having myo-inositol oxygenase activity can be delivered as a therapeutic in cases were increased myo-inositol oxygenase activity is desired.

A polypeptide having myo-inositol oxygenase activity, or variant thereof, can be incorporated into a pharmaceutical composition. For administration to animals, purified myo-inositol oxygenase polypeptide or variants thereof are generally combined with a pharmaceutically acceptable carrier. Pharmaceutical preparations can contain only one type of myo-inositol oxygenase polypeptide or they can contain a combination of various myo-inositol oxygenase polypeptides. In general, the nature of the carrier will depend on the particular mode of administration being employed. For instance, parenteral formulations usually contain injectable fluids that include pharmaceutically and physiologically acceptable fluids such as water, physiological saline, balance salt, solutions, aqueous dextrose, glycerol, human albumin, or the like as a vehicle. For solid compositions (e.g., powder, pill, tablet, or capsule forms) conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances such as wetting or emulsifying agents, preservatives, and pH buffering agents and the like, for example, sodium acetate or sorbitan monolaurate.

The therapeutic compositions described herein can be administered by any route. For example, a composition containing a polypeptide having myo-inositol oxygenase activity can be administered subcutaneously or by ingestion. In addition, a composition containing a polypeptide having myo-inositol oxygenase activity can be formulated in a slow-release composition. Slow-release formulations can be produced by combining the polypeptide with a biocompatible matrix such as cholesterol. Another possible method of administering a polypeptide pharmaceutical is through the use of mini osmonic pumps. As stated above a biocompatible carrier also can be used in conjunction with this method of delivery.

A polypeptide having myo-inositol oxygenase activity can be delivered to cells by introducing a nucleic acid that encodes that polypeptide such that the polypeptide is subsequently translated by the host cell. This can be done, for example, through the use of viral vectors or liposomes. Liposomes also can be used for the delivery of the polypeptide itself.

A polypeptide having myo-inositol oxygenase activity or a nucleic acid encoding such a polypeptide can be delivered in conjunction with other therapeutic agents. These additional therapeutic agents can be used to enhance the therapeutic effect. Examples of additional therapeutics include, without limitation, hormones, ant-inflammatory agents, and antibiotics.

A pharmaceutical composition described herein can be administered by any means that achieve its intended purpose. Amounts and regimens for the administration of can be determined readily by those with ordinary skill in the clinical art of treating diseases. For use in treating these conditions, the described polypeptides can be administered in an amount effective to regulate inositiol levels. The described polypeptides can be administered to a host in vivo, such as for example, through systemic administration such as intravenous or intraperitoneal administration. Also, the described polypeptides can be administered intralesionally (i.e., injected directly into the affected area).

Effective doses of a myo-inositol oxygenase-based therapeutic treatment will vary depending on the nature and severity of the condition to be treated, the age and condition of the subject, and other clinical factors. Thus, the final determination of the appropriate treatment regimen can be made by the attending clinician. Typically, the dose range will be from about 0.1 µg/kg body weight to about 100 mg/kg body weight. Other suitable ranges include, without limitation, doses of from about 1 µg/kg to 10 µg/kg body weight. The dosing schedule can vary from once a week to daily depending on a number of clinical factors such as the subject's sensitivity to the treatment. Examples of dosing schedules are 3 µg/kg administered twice a week, three times a week, or daily; a dose of 7 µg/kg twice a week, three times a week, or daily; a dose of 10 µg/kg twice a week, three times a week, or daily; or a dose of 30 µg/kg twice a week, three times a week, or daily. In the case of a more aggressive disease, it may be preferable to administer doses such as those described above by alternate routes including intravenously or intrathecally. Continuous infusion also can be used.

The invention will be further described in the following examples, which do not limit the scope of the invention described in the claims.

EXAMPLES

Example 1

Cloning Nucleic Acid that Encodes a Polypeptide having Myo-inositol Oxygenase Activity 1. Overview A polypeptide having myo-inositol oxygenase (MIO) activity from *Cryptococcus terreus* (ATCC #11799) was partially purified using ion exchange chromatography. This partially pure preparation was further purified by 1-dimensional or 2-dimensional SDS-PAGE. The band and spots corresponding to likely candidates were carefully excised and subjected to in situ digestion for peptide separation (µLC/MS/MS) and sequence analysis. Both analyses revealed sequences that correlated with an expressed sequence tag (EST) of a hypothetical polypeptide from *Pleurotus ostreatus* having unknown function (Accession Number 6934670). Using the entire *P. ostreatus* EST sequence, BLASTN and BLASTX searches of GenBank® revealed that putative homologs exist in a wide range of organisms. One match with the *P. ostreatus* sequence was the *Homo sapiens* ORF designated EMBL: CAB63064.1 or EMBL: AL096767. Alignments with other translated sequences with a high degree of similarity to the *H. sapiens* sequence are presented (FIGS. 7A-C).

BLAST searches using the *P. ostreatus* and *Homo sapiens* translated sequences as well as an amino terminal amino acid sequence of a *Cr. neoformans* polypeptide fragment (C. J. Rosario, MS thesis, California State University, Long Beach) against the *Cr. neoformans* strain H99 EST sequence database at the University of Oklahoma yielded EST sequences containing 5' and 3' regions of a cDNA sequence with some similarities. Primers designed from these regions were used to isolate the following full-length cDNA sequence from *Cr. neoformans* strain B3501 (SEQ ID NO:1):

```
  1  atgcacgctc  ccgaagtcaa  cgactacatc  aagcacaagg  ctgttaagct
 51  cgaccaggtt  tctgacgaaa  tcgacgaggt  caatgtcttg  aagctcaagc
101  agaaggacgc  tgtcgagaag  actcaagctg  agatcgatta  cgacctcgcg
151  agcaagtttg  accaagagaa  ggacaaggct  gctttcaggc  agtacgagga
201  agcttgcgac  cgtgtcaaga  acttctacgc  tgagcaacac  ttgaagcaga
251  cctacgagta  caatgtaaag  atccgacaag  aattccgcaa  cactgtccgt
301  gctcgcatgt  ccatctggga  agcaatggag  ctcctcgaca  atctcgtcga
351  cgagtccgac  cctgacacct  ctgttggaca  gattgagcac  cttcttcaga
401  ccgctgaggc  tattcgacga  gacggcaagc  ctgaatggat  gcaagtcacc
451  ggtttgattc  acgatcttgg  caagcttctc  tgtttcttcg  gtgccgacgg
501  tcagtgggac  gttgtcggtg  acaccttcgt  tgtcggctgc  aagttttccg
551  acaagattat  ctaccccgac  accttcaagt  ctaaccccga  ctataacaac
```

-continued

```
601  cccaagttga  acaccaagta  cggtgtctat  gagcctaact  gcggtttgga 651  caacgtcttg  ctcagctggg  gtcacgatga  gtacatgtac  gagatctgca 701  agaaccaatc  tactcttccc  caagaagctc  ttgctatgat  ccgatatcac 751  tctttctacc  cctggcaccg  agagggtgcc  tacgagcatc  tcatgaacga 801  gaaggactac  tcacagctca  aggctgtcaa  ggctttcaac  ccctacgacc 851  tctattccaa  gtctgacgac  cccccaaga   aggaggagct  caagccttac 901  taccaaagcc  tcatctccaa  attcttccct  gaggaggtgc  agtggtag
```

2. Methods

Polypeptide concentrations were estimated using the Bio-Rad Protein Assay and the manufacturer's microassay protocol. Bovine gamma globulin was used for the standard curve determination. This assay is based on the Bradford dye-binding procedure (Bradford, M., *Anal. Biochem.*, 72, 248 (1976)). Polypeptide content in chromatography fractions was estimated by absorbance measurements at 280 nm.

Electrophoresis was carried out using a Bio-Rad Protean 3 minigel system and pre-cast SDS-PAGE gels (4-15% and 12%) or a Protean 3 xi system and 16 cm×20 cm×1 mm SDS-PAGE gels (12.5%) cast following the manufacturer's protocol. The gels were run according to the manufacturer's instructions with a running buffer of 25 mM Tris-HCl (pH 8.3), 192 mM glycine, and 0.1% SDS (Laemmli buffer system; Laemmli, *Nature*, 22, 680 (1970)).

Affinity chromatography was performed using Sepharose 6B substituted with myo-inositol. Myo-inositol was covalently bound to epoxy-activated Sepharose 6B packing material (Amersham Pharmacia Biotech) following the manufacturer's instructions. Briefly, 2 g of lyophilized epoxy-activated Sepharose 6B was swollen in water for 15 minutes and repeatedly washed with water on a sintered glass filter. The swollen and washed packing material was suspended in 10 mL of 10 mM NaOH containing 0.4 M myo-inositol. The mixture was incubated for 20 hours at 25° C. with gentle shaking. The excess ligand was removed by washing with 1 L water, and any remaining active groups were blocked by incubation with 1 M ethanolamine (pH 8.0) for 4 hours at 40° C. The product was then washed thoroughly with water and three cycles of alternating pH. The low pH wash consisted of 0.1 M acetate buffer (pH 4.0) with 0.5 M NaCl, and the high pH buffer consisted of 0.1 M Tris-HCl (pH 8.0) with 0.5 M NaCl. This procedure ensured that no free ligand remains ionically bound to the immobilized ligand. The final product was suspended in 50 mM TEG buffer (50 mM Tris-HCl (pH 7.0), 0.5 mM EDTA, 100 mg/L glutathione) and stored at 4° C.

About 400-1000 µg of total polypeptide in 50 µL was prepared for 2-dimensional SDS-PAGE analysis. Polypeptide samples were resuspended in SDS boiling buffer and heated at 95° C. for 10 minutes. The SDS boiling buffer contained 5% SDS, 5% BME, 10% glycerol, and 60 mM Tris-HCl (pH 6.8). The two-dimensional electrophoresis was performed according to the method of O'Farrell (*J. Biol. Chem.*, 250: 4007-4021 (1975)). Isoelectric focusing was carried out in glass tubes with an inner diameter of 2.0 mm using 2% pH 4-8 ampholines (Gallard-Schlessinger, Garden City, N.Y.) for 9600 volt-hours. The SDS in the polypeptide sample was stripped from the polypeptides during this electrophoretic step. Fifty ng of an IEF internal standard (tropomyosin) was added to each sample prior to loading. A pH gradient plot was generated using a surface pH electrode and used to calculate approximate pI values of the various polypeptides.

After equilibration in SDS sample buffer (10% glycerol, 50 mM dithiothreitol, 2.3% SDS, and 0.0625 M tris (pH 6.8)), each tube gel was sealed to the top of a stacking gel that overlays a 10% acrylamide slab gel (0.75 mm thick). SDS slab gel electrophoresis was carried out for about 4 hours at 12.5 mA/gel. The following polypeptides were obtained from Sigma Chemical Co. (St. Louis, Mo.) and added as molecular weight standards to the agarose sealing the tube gel to the slab gel: myosin (220,000), phosphorylase A (94,000), catalase (60,000), actin (43,000), carbonic anhydrase (29,000), and lysozyme (14,000). The gels were dried between transparent sheets with the acid end to the left.

After running duplicate gels for each sample, each gel was scanned with a laser densitometer (Model PDSI, Molecular Dynamics Inc, Sunnyvale, Calif.). The scanner was checked prior to scanning for linearity with a calibrated Neutral Density Filter Set (Melles Griot, Irvine, Calif.). The images were analyzed using Phoretix 2D Full software (version 5.01) such that major spots and all changing spots were outlined, quantified, and matched on all gels. In cases where polypeptide spots were missing from some gels and present in others, a small area of background was outlined appropriately to facilitate matching. The general method of computerized analysis for these pairs included automatic spot finding and quantification, automatic background subtraction lowest on boundary) and automatic spot matching in conjunction with detailed manual checking of the spot finding and matching functions. Averaged gels were generated for each sample using Phoretix software.

Spot percentages (equal to spot integrated density (volume)) were expressed as a percentage of total density of all spots measured. Differences between matched spots in different samples were calculated from averaged spot percentages using Phoretix software according to the following formula:

Difference=(1−average spot % sample x/average spot % sample ref)(−100)

The molecular weight and approximate pI values for each spot were determined from algorithms applied to the reference image.

For polypeptide isolation and sequencing, fresh buffers and stain solutions were prepared daily for the SDS-PAGE gels. A gel thickness of 1 mm was used for 1-dimensional and 0.75 mm for 2-dimensional SDS-PAGE. The gels were stained briefly with Coomassie blue (Bio-Rad catalog # 161-0436) and then destained to a clear background. The polypeptide band was excised with no excess unstained gel present. An equal area gel without polypeptide was excised as a negative control. The gel slices were placed in uncolored microcentrifige tubes, prewashed with 50% acetonitrile in HPLC-grade water, washed twice with 50% acetonitrile, and placed on dry ice until analyzed.

After in-situ enzymatic digestion of the polypeptide sample with trypsin, the resulting polypeptide fragments were separated by micro-capillary reverse-phase HPLC. The HPLC was directly coupled to the nano-electrospray ionization source of a Finnigan LCQ quadrupole ion trap mass spectrometer (μLC/MS/MS). Individual sequence spectra (MS/MS) were acquired on-line at high sensitivity for the multiple polypeptide fragments separated during the chromatographic run. The MS/MS spectra of the polypeptide fragments were correlated with known sequences using the algorithm Sequest developed at the University of Washington (Eng et al., *J. Am. Soc. Mass Spectrom.*, 5, 976 (1994)) and programs described elsewhere (Chittum et al., *Biochemistry*, 37, 10866 (1998)). The results were reviewed for consensus with known polypeptides and for manual confirmation of fidelity.

3. Growth of *Cryptococcus terreus* and Cell Extract Analysis

*Cr. terreus* (ATCC 11799) was grown at 30° C. with shaking on a medium consisting of yeast nitrogen base (YNB) (6.7 g/L), yeast extract (0.3%), 0.1 M sodium phosphate, and either myo-inositol (1%), glucose (1%), or no additional carbon source. Similar growth experiments were also done with YM medium (0.3% yeast extract, 0.3% malt extract, 0.5% peptone) with either myo-inositol (1%), glucose (1%), or no additional carbon source. The pellets from 50 mL of overnight cultures were washed and resuspended in 50 mM TEGGP buffer (50 mM Tris-HCl (pH, 7.0), 0.5 mM EDTA, 100 mg/L glutathione, 5% glycerol, and protease inhibitor cocktail ("Complete" cocktail at 1 tablet per 10 mL buffer; Roche Molecular Biochemicals)). The cell extracts were prepared by subjecting the washed cell pellets to 3 passes through a Spectronic French pressure cell (mini-cell) at 19,000 psi followed by centrifugation at 20,000×g for 45 minutes. To remove any low molecular weight components of the cell extracts that might interfere with the analyses, the clear supernatants (after centrifugation) were applied to Pharmacia PD-10 columns (9.1 mL) previously equilibrated with 50 mM TEGGP buffer. The same buffer was used to elute the polypeptides from these disposable gel filtration columns. The eluents were assayed for MIO activity.

MIO activity was determined using a modification of the method described by Reddy et al. (*J. Biol. Chem.*, 256, 8510 (1981)). Briefly, this assay is based on the reaction of orcinol (5-methyl-1,3-benzenediol) with the MIO enzyme reaction product, D-glucuronic acid. The standard assay mixture contained 50 mM Tris-HCl (pH 8.0), 2.0 mM cysteine, 1.0 mM ferrous ammonium sulfate, 60 mM myo-inositol, and appropriate quantities of enzyme in a total volume of 0.50 mL. The stock L-cysteine solution (0.10 M) was prepared every two weeks, and the stock ferrous ammonium sulfate solution (0.50 M) was prepared fresh daily. The enzyme solutions consisted of cell extracts prepared as described or chromatography fractions generated during the partial purification of the enzyme. Prior to initiating the reaction by addition of the substrate myo-inositol (stock solution of 0.50 M, dissolved in 50 mM TEGG), all other reagents were mixed together by vortexing and incubated for 5 minutes at 30° C. The substrate was then added to initiate the assay. After vortex-mixing the components, the reaction was carried out in an air atmosphere at 30° C. with shaking at 200 rpm for 10 minutes. The reaction was terminated by the addition of 75 μL of 20% trichloroacetic acid. After vortexing, the assay mixture was transferred to a 1.5 mL polypropylene microcentrifuge tube, and the precipitated polypeptide was separated by centrifugation at 21,000×g for 3 minutes at 25° C. The supernatant was transferred to a new 1.5 mL polypropylene microcentrifige tube, and the D-glucuronic acid concentration was determined by the orcinol colorimetric assay.

The orcinol calorimetric determination assay was performed as follows. Freshly prepared orcinol reagent (0.6 mL; 0.4% (w/v) orcinol, 0.09% (w/v) ferric trichloride hexahydrate in concentrated HCl) was added to 0.3 mL of the clear supernatant. The mixture was vortex-mixed and then incubated in a boiling water bath for 30 minutes. After cooling to 25° C., the mixture was cleared by centrifugation at 21,000×g for 3 minutes. The supernatant was transferred to a disposable cuvette, and the absorbance was measured at 660 nm. A standard curve was generated by replacing the enzyme fraction with D-glucuronic acid (0 to 40 μg/mL) and carrying out the assay as described above. In a typical experiment the specific activity (μg glucuronate formed/mg protein/10 minute incubation) of MIO in *Cr. terreus* grown with inositol as the carbon source was 3.9 versus 1.1 when grown on glucose.

All reactions were run in duplicate, and all polypeptide fractions were assayed with and without added myo-inositol substrate (an equal volume of TEGG buffer with or without substrate was added to initiate the assay). The average of the absorbance readings of the assay mixtures carried out without substrate was subtracted from the average of readings of the assay mixtures containing substrate. The difference in the values was used to calculate the specific activity as μg D-glucuronic acid formed per mg polypeptide in 10 minutes.

Cell extracts from *Cr. terreus* were assayed for enriched myo-inositol oxygenase (MIO) activity when the cells were grown on myo-inositol vs. glucose. These cell extracts were analyzed by subtractive computer analysis of 2-dimensional polyacrylamide electrophoresis gels as described above.

The results of the 2-dimensional SDS-PAGE computer analysis of *Cr. terreus* 11799 cell extracts revealed that a group of about four polypeptides are induced when *Cr. terreus* cells are grown in the presence of inositol. These polypeptides were numbered 124, 125, 126 and 117. Two or more of these spots could be isozymes of the same polypeptide since their sizes and pI values were similar. The molecular weights of the four polypeptides ranged from 34 to 36 kDa, and their pIs range from 5.67 to 5.95.

4. Partial Purification of a Polypeptide from *Cr. terreus* Having MIO Activity

*Cr. terreus* (ATCC 11799) was grown overnight on YNB medium with inositol as the carbon source (26° C. with shaking, final absorbance at 650 nm of approximately 1). All operations subsequent to the growth of the cells were carried out at 1-4° C. unless stated otherwise. The cells from 1.5 L of culture were harvested by centrifugation at 12,000×g for 10 minutes and washed with 2×200 mL of 10 mM TEGG buffer (10 mM Tris-HCl (pH 7.0), 0.5 mM EDTA, 100 mg/L glutathione, and 5% glycerol), centrifuging between washes to pellet the cells. The washed cells (24.2 g wet cell weight) were resuspended in 20 mL 10 mM TEGGP buffer containing protease inhibitor cocktail ("Complete" protease inhibitor cocktail tablets at 1 tablet per 10 mL buffer; Roche Molecular Biochemicals) and disrupted by three passes through a Spectronic Prench pressure cell (40K) at 25,000 psi. The cell debris was removed by centrifugation at 20,000×g for 45 minutes, and the pellet was discarded. The supernatant was desalted by separation on Pharmacia disposable PD-10 columns (2.5 mL extract loaded per column) that had each been previously equilibrated with 20 mL 10 mM TEGG buffer followed by 5 mL 10 mM TEGGP buffer. The polypeptide fraction was eluted with 3.5 mL of 10 mM TEGGP buffer per column (total volume=42 mL).

The resulting cell extract was applied over three runs to a Bio-Rad UnoQ (6 mL) column previously equilibrated with 10 mM TEGG buffer. The anion exchange column was washed with 30 mL 10 mM TEGG and eluted with a linear gradient of 0 to 400 mM NaCl in 10 mM TEGG buffer (50 mL) followed by a step gradient to 2.0 M NaCl (12 mL). The flow rate for the elution was 1 mL/minute, and 5 mL fractions were collected. The fractions were assayed using the MIO-orcinol assay procedure described above. To achieve accurate activity results, each fraction from the UnoQ chromatography was desalted before assaying as described above. The fractions determined to have MIO activity were pooled.

The active desalted polypeptide fractions were further purified by separation on an Inositol Sepharose column (1×10 cm) previously equilibrated with 10 mM TEGG buffer. The affinity column was washed with 25 mL of the same buffer and eluted with a linear gradient of 0 to 200 mM NaCl in 10 mM TEGG buffer (24 mL) followed by a step gradient to 500 mM NaCl (7 mL). The polypeptide fractions determined to have activity using the MIO-orcinol assay procedure were pooled and stored at 4° C. The results of a typical preparation, starting with 1.5 L of cell culture are shown in Table II. Specific activity was calculated by dividing the amount of glucuronate produced by the total polypeptide of the sample. The relative purity of the MIO polypeptide during purification was estimated by the relative intensity of the band on one-dimensional gel electrophoresis.

TABLE II

Purification of a polypeptide from Cr. terreus 11799 having MIO activity

| Fraction | Volume mL | [polypeptide] mg/mL | Activity per mL | Specific Activity activity/mg polypeptide | Purification -fold |
|---|---|---|---|---|---|
| Cell free extract | 17.5 | 13.95 | 54.1 | 3.9 | 1 |
| Uno Q | 14.0 | 0.48 | 134.0 | 278.2 | 71 |
| Inositol-Sepharose | 4.0 | 0.19 | 134.8 | 709.5 | 182 |

(activity is defined as µg glucuronate formed during assay)

5. Polypeptide Sequencing

A polypeptide sample from Cr. terreus (ATCC # 11799) having MIO activity that was partially purified using ion exchange chromatography on a Bio-Rad UnoQ column (6 mL) was further purified by 1-dimensional SDS-PAGE using a 16 cm×20 cm×1 mm 12.5% slab gel. The gel was stained briefly with Coomassie blue, and a band corresponding to a molecular weight of about 35 kDa was excised and sequences added as described above.

Three consensus sequences were identified from three of the MS/MS spectra and manually confirmed to be as follows: DGKPEWMQVTGLVHDLGK (SEQ ID NO:2); DGKPEWM*QVTGLVHDLGK (SEQ ID NO:3); and YHSFYPWHR (SEQ ID NO:4). These three sequences correlated with a hypothetical polypeptide of unknown function from Pleurotus ostreatus, also known as oyster mushroom.

A polypeptide sample from Cr. terreus (ATCC # 11799) having MIO activity that was partially purified by anion exchange chromatography on a Bio-Rad UnoQ column and affinity chromatography using Inositol-Sepharose was further separated using 2-dimensional electrophoresis. Spots from these gels were correlated with spots from the 2-dimensional gels of Cr. terreus cell extracts subjected to limited subtractive computer analysis as described above. One of these spots (#117 of the cell extract gels; MW=35,700 Da; pI=5.95) predominated in the gels of the partially purified MIO sample and was chosen for sequence analysis. This spot was excised from the gel and treated as described above for in situ digestion, peptide separation (µLC/MS/MS), and sequence analysis. The following two distinct consensus sequences were identified: DGKPEWMQVT-GLVHDLGK (SEQ ID NO:2) and YHSFYPWHR (SEQ ID NO:4). These sequences are identical to those obtained from the partially purified sample separated by 1-dimensional gel electrophoresis.

The data generated from these polypeptide samples revealed sequence similarity to partial sequences of an EST clone (gi:6934670) from Pleurotus ostreatus. Using the entire P. ostreatus EST as a template, a search of the public gene sequence databases was performed to search for putative mio homologs in a wide range of organisms. BLASTN and BLASTX searches revealed several full-length homologs. The sequence with the highest similarity to the P. ostreatus EST was a 217 amino acid putative polypeptide from Pinus radiata (Monterey pine; gi:293552; E score of 7 $e^{-57}$). The searches also revealed three ORFs from Arabidopsis thaliana (thale cress; gb:AAF43953.1; gb:AAC62136.1; gb: pir: T06010), two ORFs from Homo sapiens (human; gb:AAF25204.1; emb: CAB63064.1), and one ORF from Rattus norvegicus (rat; gb: AAF25203.1). Other sequences were identified in Mus musculus (mouse) as well as in rice and tomato EST databases. The sequence of one of the A. thaliana sequences (gb: AAC62136.1) contained an intron, and the sequence was corrected to delete this region. FIGS. 7A-C shows an alignment of several sequences sharing sequence similarity with the Pinus radiata sequence.

6. Nucleic Acid Cloning

BLAST searches using the P. ostreatus and Homo sapiens translated sequences as well as an amino terminal amino acid sequence of a Cr. neoformans polypeptide fragment (C. J. Rosario, MS thesis, California State University, Long Beach) against the Cr. neoformans (strain H99) EST sequence database at the University of Oklahoma were performed. One EST exhibited sequence similarity with all three sequences including the amino terminal region. By alignment analysis with the 5' and 3' regions of this clone (designated a7e05cn.r1 and a7e05cn.f1), putative start and stop codons were identified. Primers were designed from these sequences and were used to isolate the entire cDNA sequence from Cr. neoformans. Specifically, the following PCR primers were designed for cloning into pET30a (Novagen) and pYES2 (Invitrogen): 5'-GGCC<u>GGTACC</u>ATGGACGCTCCCGAAGTCAA-3' (SEQ ID NO:5; 5' primer for both vectors), 5'-CGC<u>CTCGAG</u>CTACCACTGCACCTCCTCAG-3' (SEQ ID NO:6; 3' primer for pET30), and 5'-GCGC<u>TCTAGA</u>CTACCACTGCACCTCCTCAG-3' (SEQ ID NO:7; 3' primer for pYES2). The restriction sites are underlined, and the start and stop codons in bold.

Both the mio insert for pET30a cloning and the vector were digested with NcoI and XhoI before ligation using the Roche Rapid DNA Ligation Kit. The mio insert and pYES2 were digested with KpnI and XbaI and ligated using the Roche Rapid DNA Ligation Kit. The enzyme KpnI leaves an intact Kozak sequence (yeast ribosome binding site). Part of the Kozak sequence was engineered to contain a change (from C to G) in the fourth bp of the coding sequence. The *Cr. neoformans* mio nucleic acid was amplified from a *Cr. neoformans* cDNA library (strain B3501; Stratagene catalog # 937052) using the following protocol: (1) 94° C. for 5 minutes, (2) 94° C. for 30 seconds, (3) 55° C. for 60 seconds, (4) 72° C. for 1.5 minutes, (5) repeat steps 2-4 9 times, (6) 94° C. for 30 seconds, (7) 55° C. for 60 seconds, (8) 72° C. for 1.5 minutes (+5 sec/cycle), (9) repeat steps 6-8 14 times, (10) 94° C. for 30 seconds, (11) 55° C. for 60 seconds, (12) 72° C. for 2.75 minutes, (13) repeat steps 10-12 9 times, and (14) 72° C. for 7 minutes. Sequencing was performed with primers complementary to regions of the vectors adjacent to the multiple cloning sites, and then primer walking was performed to generate the full double-stranded sequence.

7. MTO Expression in *E. coli*

Chemically competent *E. coli* BLR(DE3) cells were transformed with the pET30a vector containing the *Cr. neoformans* mio sequence following the manufacturer's instructions. Once transformed, the BLR(DE3) cells were grown in 50 mL 2×YT medium (16 g tryptone, 10 g yeast extract, 5 g sodium chloride) containing 50 µg/mL kanamycin to an $OD_{650}$ of 0.5 at 37° C. After adding 1 mM IPTG (final concentration) to induce polypeptide expression, the cells were grown for an additional four hours at 30° C. All operations subsequent to the growth of the cells were carried out at 1-4° C. unless stated otherwise. The cells were harvested by centrifugation at 12,000×g for 10 minutes and washed twice with 50 mM TEGG buffer (50 mM Tris-HCl (pH 7.0), 0.5 mM EDTA, 100 mg/L glutathione, and 5% glycerol) centrifuging between washes (12,000×g; 10 minutes) to pellet the cells. The washed cells were lysed using Novagen Bug Buster reagent (5 mL reagent per g wet cell weight) containing Novagen benzonase nuclease (1 µg benzonase nuclease per mL Bug Buster reagent) and Calbiochem Protease inhibitor Cocktail III (diluted 1:500) according to the manufacturer's instructions. The cell debris was removed by centrifugation at 21,000×g for 20 minutes, and the pellet was discarded. The supernatant (cell extract) was immediately assayed for myo-inositol oxygenase activity as described above. In a typical experiment, the cell extract from cells expressing the *Cr. neoformans* sequence exhibited a specific activity of 138 µg glucuronic acid formed per mg total protein in 10 minutes. A cell extract from induced cells containing PET30a with no insert exhibited a specific activity of 10.7 µg glucuronic acid formed per mg total protein in 10 minutes.

The *Cr. neoformans* polypeptide also was purified and tested for myo-inositol oxygenase activity. Briefly, a cell extract from a 250 mL liquid culture of BLR(DE3) cells containing the *Cr. neoformans* mio sequence in pET30, grown in 2×YT medium with 50 µg/mL kanamycin and induced with 1 mM IPTG, was prepared as described above. The *Cr. neoformans* polypeptide was purified using a Novagen His-Bind Quick 900 cartridge as described in the manufacturer's instructions. The eluent (2.5 mL of the total 4.0 mL in Novagen Elute Buffer) was desalted by separation on a Pharmacia disposable PD-10 column that had been previously equilibrated with 20 mL of 50 mM TEGG buffer followed by 5 mL of 50 mM TEGG buffer containing protease inhibitor cocktail (50 mM TEGGP). The protein fraction was eluted with 3.5 mL of 50 mM TEGGP buffer and was immediately assayed for myo-inositol oxygenase activity as described above. The total protein in the samples was determined using the Bio-Rad Total Protein Reagent following the manufacturer's directions. In a typical assay, the desalted eluent exhibited a specific activity of 203 µg glucuronic acid formed per mg protein in 10 minutes.

8. AHO Expression in *S. cerevisiae*

Competent *S. cerevisiae* INVSc1 cells were transformed with the pYES2 vector containing the *Cr. neoformans* mio sequence. Once transformed, the cells were grown in 20 mL SC-uracil medium containing 2% raffinose overnight at 30° C. with shaking at 200 rpm following the InVitrogen protocol. Pelleted cells from the overnight culture were used to inoculate a 250 mL liquid culture in SC-uracil medium containing 2% galactose and 1% raffinose to an $OD_{650}$ of 0.4. The resulting culture was incubated at 30° C. with shaking. Aliquots were withdrawn at 0, 5, and 10 hours after induction with galactose, and the cells were harvested by centrifugation at 12,000×g for 10 minutes. After centrifugation, the cells were washed with 50 mM TEGG buffer (50 mM Tris-HCl (pH 7.0), 1 mM EDTA, 100 mg/L glutathione, and 5% glycerol), pelleted again, and frozen at −80° C. All of the following operations for cell extract preparation were carried out at 1-4° C. unless stated otherwise. The washed cells were resuspended in 50 mM TEGG buffer containing proteases inhibitor cocktail (Roche "Complete" Protease Inhibitor Cocktail Tablets at 1 tablet per 10 mL buffer; 50 mM TEGGP) and disrupted by three passes through a Spectronic French pressure mini-cell at 19,000 psi. The cell debris was removed by centrifugation at 21,000×g for 30 minutes, and the pellet was discarded. The resulting cell extract was immediately assayed for myo-inositol oxygenase activity. The total protein in the samples was determined using the Bio-Rad Total Protein Reagent following the manufacturer's directions.

In a typical experiment, the cell extract from *S. cerevisiae* cells harvested 5 hours after induction of polypeptide expression exhibited a specific activity of 21.1 µg glucuronic acid formed per mg protein in 10 minutes, while the specific activity of the cell extract from cells harvested 10 hours after induction was 12.8 µg. The specific activity of the cell extract from cells harvested just prior to induction was 6.7 µg.

Example 2

Cloning Nucleic Acid that Encodes a Human Polypeptide Having Myo-inositol Oxygenase Activity

*E. coli* DH10B ElectroMAX cells were purchased from Life Technologies, Inc. (catalog #18290-015), and the plasmid pTRC99A was purchased from Amersham Pharnacia Biotech (catalog #27-5007). The human kidney cDNA library was purchased from Stratagene (catalog # 937250). Bacterial growth media components were purchased from Difco or Fisher Scientific, and other reagents were of analytical grade or the highest grade commercially available. For polypeptides, electrophoresis was carried out using a Bio-Rad Protean II xi cell gel system. For nucleic acid, electrophoresis was carried out using a Bio-Rad Mini-Sub Cell GT system. An Eppendorf Mastercycler Gradient thermal cycler was used for PCR experiments. UV-visible spectrometry was done using a Bio-Rad SmartSpec 3000 or a Molecular Devices SpectraMAX Plus spectrophotometer. Electroporations were performed using a Bio-Rad Gene Pulser II system. Primers were purchased from Integrated DNA Technologies, Inc. Automated DNA sequencing was carried out using an ABI prism 377 DNA sequencer.

PCR primers specific for the *Homo sapiens* ORF (designated EMBL: CAB63064.1) were designed, and the desired cDNA was amplified from a human kidney cDNA library (Stratagene). The primers were as follows: 5'-ATAT CCATGGAGGTGACGGTGGGCCCAGAC-3' (SEQ ID NO:8; 5' primer with NcoI site) and 5'-CTAT TCTAGATCACCAGCTCAGGATGCC-3' (SEQ ID NO:9; 3' primer with XbaI site). The restriction sites are underlined, and the start and stop codons are in bold. The PCR reactions contained 1 µM final concentration of each primer; 0.2 mM of dATP, dCTP, dGTP, and dTTP; 2.5 units of Expand High Fidelity PCR Polymerase (Roche Molecular Biochemicals); 1 mM MgCl$_2$; 5 µL of the human kidney cDNA library; and 1×HF buffer without MgCl$_2$ in a 50 µL reaction. The thermocycler program utilized a hot start of 94° C. for 5 minutes; followed by 10 cycles of a denaturing step at 94° C. (30 seconds), an annealing step at 50° C. (1 minute), and an extension step at 72° C. (1.5 minutes); 15 cycles of a denaturing step at 94° C. (30 seconds), an annealing step at 50° C. (1 minute), and an extension step at 72° C. (1.5 minutes) that increased 5 seconds per cycle; 10 cycles of a denaturing step at 94° C. (30 seconds), an annealing step at 50° C. (1 minute), and an extension step at 72° C. (2.75 minutes); and finally a finishing step at 72° C. (7 minutes). The amplified DNA with an approximate size of 850 bp was purified from a 1% agarose gel using a Qiagen QIAquick Gel Extraction Kit and then digested with XbaI and NcoI. The digested DNA was ligated into the pTRC99A plasmid (also digested with XbaI and NcoI) at a 5:1 molar ratio of insert to plasmid using the Rapid DNA Ligation Kit (Roche Molecular Biochemicals). Transformations into electrocompetent DH10B were performed under standard conditions described in the Bio-Rad electroporation manual. Clones containing the human nucleic acid were identified by restriction analysis and confirmed by DNA sequencing.

*E. coli* cells containing the human nucleic acid encoding an enzyme having MIO activity were grown in 100 mL LB medium containing 100 µg/ml ampicillin to an OD$_{650}$ of 0.5 and were induced with 1 mM IPTG (final concentration). The induced cells were grown an additional four hours at 30° C. All operations subsequent to the growth of the cells were carried out at 1-4° C. unless stated otherwise. The cells were harvested by centrifugation at 12,000×g for 10 minutes and washed twice with 50 mM TEGG buffer (50 mM Tris-HCl (pH 7.0), 0.5 mM EDTA, 100 mg/L glutathione, and 5% glycerol), centrifuging between washes (12,000×g; 10 minutes) to pellet the cells. The washed cells were re-suspended in 2.0 mL of 50 mM TEGGP buffer containing protease inhibitor cocktail (Roche "Complete" Protease Inhibitor Cocktail Tablets at 1 tablet per 10 mL buffer) and were lysed with lysozyme (300 µg/mL) for 30 minutes. The cell debris was removed by centrifugation at 38,000×g for 45 minutes, and the pellet was discarded. The supernatant was desalted by separation on a Pharmacia disposable PD-10 column (2.5 mL extract loaded per column) that had been previously equilibrated with 20 mL of 50 mM TEGG buffer followed by 5 mL of 50 mM TEGG buffer containing protease inhibitor cocktail (50 mM TEGGP). The polypeptide fraction was eluted with 3.5 mL of 50 mM TEGGP buffer and was immediately assayed for myo-inositol oxygenase activity as described in Example 1.

The cell extract from cells containing the nucleic acid encoding the human MIO polypeptide exhibited a specific activity of 8.8 µg glucuronic acid formed per mg polypeptide in 10 minutes. A cell extract from induced cells containing pTRC99A with no insert exhibited a specific activity of 5.5 µg glucuronic acid formed per mg polypeptide in 10 minutes.

Example 3

Activity of Human MIO Polypeptide in *Bacillus megaterium* Cells

The following PCR primers specific for the *Homo sapiens* ORF (designated EMBL: CAB63064.1) are designed, and the desired cDNA is amplified from a human kidney cDNA library (Stratagene): 5' primer with BsrG1 site: 5'-ATTA TGTACAATGAAGGTGACGGTGGGCCCAGAC-3' (SEQ ID NO:45) and 3' primer with Kpn1 site: 5'-CTAT GGTACCTCACCAGCTCAGGATGCC-3' (SEQ ID NO:46). The start and stop codons are in bold, and the restriction sites are underlined. The PCR conditions are as follows. The reactions contain 1 mM final concentration of each primer, 0.2 mM of dATP, dCTP, dGTP, and dTTP; 2.5 units of Expand High Fidelity PCR Polymerase (Roche Molecular Biochemicals); 1 mM MgCl$_2$; 5 mL of the human kidney cDNA library; and 1×HF buffer in a 50 mL reaction. The thermocycler program utilizes a hot start of 94° C. for 5 minutes followed by 10 cycles of a denaturing step at 94° C. (30 seconds), an annealing step at 50° C. (1 minute), and an extension step at 72° C. (1.5 minutes); 15 cycles of a denaturing step at 94° C. (30 seconds), an annealing step at 50° C. (1 minute), and an extension step at 72° C. (1.5 minutes) that increases 5 seconds per cycle; 10 cycles of a denaturing step at 94° C. (30 seconds), an annealing step at 50° C. (1 minute), and an extension step at 72° C. (2.75 minutes); and finally a finishing step at 72° C. (7 minutes). The amplified DNA with a size of about 850 bp is purified from a 1% agarose gel using a Qiagen QIAquick Gel Extraction Kit and then is digested with BsrG1 and KpnI.

A BsrG1 restriction site is inserted into the vector pWH1520 from MoBiTec LLC by inserting a thymidine (T) nucleotide between bases 4 and 5 and by deleting the base at position 8 (A) using the QuickChange Site-Directed Mutagenesis Kit (Stratagene) following the manufacturer's protocol. The resulting plasmid is pWH1520A. The digested PCR product is ligated into the pWH1520A plasmid (also digested with BsrG1 and Kpn1) using the Rapid DNA Ligation Kit (Roche Molecular Biochemicals) generating plasmid hsmiopWH1520A. Transformations into electrocompetent DH10B are performed under standard conditions described in the Bio-Rad electroporation manual for this type of cell. Clones containing the human mio sequence are identified by restriction analysis and confirmed by DNA sequencing. The hsmiopWH1520A plasmid purified from DH10B transformants is transformed into commercially available *B. megaterium* protoplasts following the manufacturer's protocol (MoBiTec LLC; Marco Island, Fla.). Clones containing the hsmiopWH1520A plasmid are identified by restriction analysis and confirmed by DNA sequencing.

*B. megaterium* cells containing the hsmiopWH1520A are grown in 100 mL LB medium containing 10 mg/mL tetracycline to an OD$_{650}$ of 0.3 and are induced with 0.5% xylose (final concentration). Cells are grown to an OD$_{600}$ of 1.5 and harvested according to the manufacturer's protocol for protein expression in *B. megaterium*. All operations subsequent to the growth of the cells are carried out at 1-4° C. unless stated otherwise. The cell pellet is resuspended in 50 mM TEGGP buffer (50 mM Tris-HCl (pH 7.0), 0.5 mM EDTA, 100 mg/mL glutathione, 5% glycerol, and Roche Protease Inhibitor Cocktail (1 tablet per 10 mL buffer)) and then disrupted by sonication. After centrifugation at 12,000 rpm for 45 minutes to remove the cell debris, the supernatant is desalted by separation on a Pharmacia disposable PD-10 column (2.5 mL extract loaded per column) that is previously equilibrated with 20 mL of 50 mM TEGG buffer (50 mM Tris-HCl, 0.5 mM EDTA, 100 mg/mL glutathione, and 5% glycerol) followed by 5 mL of 50 mM TEGGP. The protein fraction is eluted with 3.5 mL of 50 mM TEGGP buffer and is immediately assayed for myo-inositol oxygenase activity.

Example 4

Activity of Human MIO Polypeptide in Yeast Cells

*Escherichia coli* DH10B ElectroMAX cells were purchased from Life Technologies, Inc (catalog #18290-015). *Saccharomyces cerevisiae* cells (INVSc1; catalog #C810-00) and the pYES2 vector (catalog #V825-20) were purchased from Invitrogen. The Invitrogen S.c. EasyComp™ Transformation Kit (catalog #K5050-01) was used to prepare and transform INVSc1 chemically competent cells. Bacterial growth media components were from Difco or Fisher Scientific, and other reagents were of analytical grade or the highest grade commercially available. Plasmids were purified from *E. coli* cells using Qiagen Mini and Midi Plasmid Prep Kits, while plasmids were purified from *S. cerevisiae* cells using a Zymoprep™ Kit (Zymo Research; catalog #D2001).

PCR primers specific for the human mio/pTRC99A construct described in Example 2 were designed as follows: 5'-AATTGGTACCATGGAGGTGACGGTGGGCCCAGAC-3' (SEQ ID NO:10; 5' primer with KpnI site) and 5'-CTAT TCTAGATCACCAGCTCAGG-ATGCC-3' (SEQ ID NO: 11; 3' primer with XbaI site). The restriction sites are underlined, and the start and stop codons are in bold. The PCR reactions contained 1 µM final concentration of each primer; 0.2 mM of dATP, dCTP, dGTP, and dTTP; 1.75 units of Expand High Fidelity PCR Polymerase (Roche); 1.5 mM MgCl$_2$, and 0.025 µL of the human mio/pTRC99A plasmid (55 ng/µL) in a 50 µL reaction. The thermocycler program utilized a hot start of 94° C. for 5 minutes; followed by 10 cycles of a denaturing step at 94° C. (30 seconds), an annealing step at 50° C. (1 minute), and an extension step at 72° C. (1.5 minutes); 15 cycles of a denaturing step at 94° C. (30 seconds), an annealing step at 50° C. (1 minute), and an extension step at 72° C. (1.5 minutes) that increased 5 seconds per cycle; 10 cycles of a denaturing step at 94° C. (30 seconds), an annealing step at 50° C. (1 minute), and an extension step at 72° C. (2.75 minutes); and finally a finishing step at 72° C. (7 minutes). The amplified DNA with an approximate size of 850 bp was purified from a 1% agarose gel using a Qiagen QIAquick Gel Extraction Kit and then digested with KpnI and NcoI. The digested DNA was ligated into the pYES2 plasmid (also digested with KpnI and NcoI) at 4:1 and 6:1 molar ratios of insert to plasmid using the Rapid DNA Ligation Kit (Roche Molecular Biochemicals). Transformations into electrocompetent DH10B cells were performed under standard conditions described in the Bio-Rad electroporation manual. Clones containing the human nucleic acid were identified by restriction analysis and confirmed by DNA sequencing.

Transformations of competent *S. cerevisiae* INVSc1 cells with pYES2 plasmid containing the human insert (purified from DH10B cells) were carried out according to the manufacturer's instructions of the Invitrogen S.C. EasyComp™ Transfomation Kit. The transformation reactions were plated on SC minimal plates deficient in uracil (SC-uracil). Clones containing the human nucleic acid were identified by PCR analysis using primers complementary to sequence on both sides of the multiple cloning region of pYES2.

Expression of the human MIO polypeptide was induced in *S. cerevisiae* INVSc1 cells according to the Invitrogen protocol for recombinant proteins in pYES2 under the control of the GAL1 promoter. Cells were grown in 50 mL SC-uracil medium containing 2% raffinose overnight at 30° C. with shaking at 200 rpm. Pelleted cells from the overnight culture were used to inoculate a 350 mL liquid culture in SC-uracil medium containing 2% galactose and 1% raffinose to an OD$_{650}$ of 0.4; the resulting culture was incubated at 30° C. with shaking. Aliquots were withdrawn at 0 and 12 hours after induction with galactose, and the cells were harvested by centrifugation at 12,000×g for 10 minutes. The pellets were washed with 50 mM TEGG buffer (50 mM Tris-HCl (pH 7.0), 0.5 mM EDTA, 100 mg/L glutathione, and 5% glycerol), pelleted again, and frozen at −80° C.

All of the following operations for cell extract preparation were carried out at 1-4° C. unless stated otherwise. The cells were disrupted with glass beads (Sigma, 150-212 microns) in 50 mM TEGGPP buffer (50 mM Tris-HCl (pH 7.0), 0.5 mM EDTA, 100 mg/L glutathione, 5% glycerol, Roche "Complete" Protease Inhibitor Cocktail at 1 tablet per 10 mL buffer, and 1 mM Pefabloc (Roche Moleuclar Biochemicals)) following the procedure described by Dunn and Wobbe in *Current Protocols in Molecular Biology* for small scale preparations (B. Dunn and C. R. Wobbe, volume 2, section 13.13.4, F. M. Ausubel, R. Brent, R. E. Kingston, D. D. Moore, J. F. Seidman, J. A. Smith, K. Struhl eds, John Wiley & Sons, Inc., (1999)). The cell debris and glass beads were removed by centrifugation at 21,000×g for 15 minutes. The supernatant was desalted by separation on a Pharmacia disposable PD-10 column (2.5 mL extract loaded per column) that had each been previously equilibrated with 20 mL of the 50 mM TEGG buffer followed by 5 mL of the 50 mM TEGGPP buffer. The polypeptide fractions were eluted with 3.5 mL of the 50 mM TEGGPP buffer and were immediately assayed for myo-inositol oxygenase activity as described in Example 1.

In a typical experiment, the cell extract from *S. cerevisiae* cells harvested 12 hours after induction of the human MIO polypeptide exhibited a specific activity of 13.4 µg glucuronic acid formed per mg polypeptide in 10 minutes. A cell extract from similarly induced cells containing pYES2 with no insert showed a specific activity of 5.7 µg glucuronic acid formed per mg total protein in 10 minutes.

Example 5

Activity of Human MIO Polypeptide in Insect Cells

The human nucleic acid encoding an MIO enzyme within the pTRC99A plasmid described in Example 2 was subcloned into Baculovirus. Specifically, the pTRC99A-mio clone was digested with Nco I and Sal I, and the 872 bp human mio fragment was isolated by gel purification. The vector pFastBacHTa was also digested with Nco I/Sal I, and treated with calf intestinal phosphatase. The human MIO coding sequence was ligated into the vector in frame with an N-terminal His tag.

DNA sequencing was performed to verify that a polypeptide with the following amino acid sequence was encoded by the construct: MSYYHHHHHHDYDIPTTEN-LYFQGAM EVTVGPDPSLVYRPDVDPEVAKDKASFRNYTSGPLL DRVFTTYKLMHTHQTVDFVRSKHAQFGGFSYKKM TVMEAVDLLDGLVDESDPDVDFPNSFHAFQTAEGIR KAHPDKDWFHLVGLLHDLGKVLALFGEPQWAVVGD TFPVGCRPQASVVFCDSTFQDNPDLQDPRYSTELGM YQPHCGLDRVLMSWGHDEYMYQVMKFNKFSLPPE AFYMIRFHSFYPWHTGRDYQQLCSQQDLAMLPWVR EFNKFDLYTKCPDLPDVDKLRPYYQGLIDKYCPGILS W (SEQ ID NO:12; non-human sequence is underlined, His-Tag is in bold).

The baculovirus transfer vector was used to create bacmid DNA, which was then transfected into Sf-9 and Hi5 cells. The virus from the transfection underwent a single amplification and titering. The resultant titered primary amplified virus (40 mL volume) was used for the initial expression screening.

The majority of the 40-mL singularly amplified viral stock was used to infect 50 mL cultures of Sf-9 and hi5 cells at multiplicities of infection (MOI) of 0.1, 1, and 5, each for post infection harvest times (HPI) of 48 hours and 72 hours. In parallel, expressions using the same cells, MOI, and HPI conditions were done with vector alone to serve as negative controls. Cells and media were harvested for expression analysis, and cell extracts were resuspended in TEG buffer (50 mM Tris-HCl (pH 7.5), 0.5 mM EDTA, 100 mg/L glutathione) plus 10% glycerol.

Figure 8:
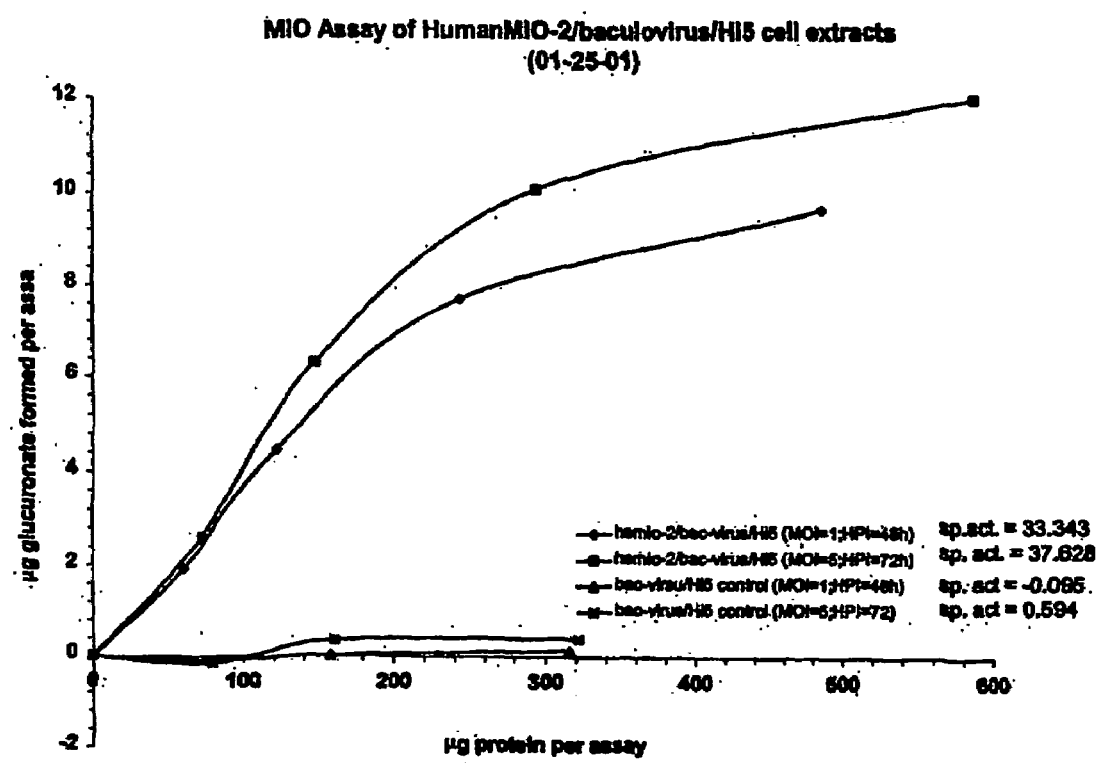
FIG. 8 is a graph plotting μg glucuronate formed per assay versus μg protein per assay for the indicated cell extracts.

Expression analysis investigated the production of soluble polypeptide using SDS-PAGE and Western blot analysis with His-tag antibodies. Optimal expression was determined to occur in the HiS cell line with MOI of 1 or 5, and 48 or 72 hours of post-infection harvest times. Samples were flash-frozen with liquid nitrogen and placed on dry ice until assayed. MIO activity assays were performed as described in Example 1. Hi5 cells expressing the human polypeptide exhibited MIO activity, while Hi5 cells lacking the human polypeptide did not (FIG. 8). Specific activity in FIG. 8 is defined as µg glucuronate formed/mg protein/10 minute incubation.

Further expression experiments were done at a MOI of 1 and a 48-hour HPI. Cell paste was suspended (about 6 g of each clone from 0.5 L insect culture) in 50 mL lysis buffer (1×PBS (pH 7.4), 10% glycerol, 1 µg/mL pepstatin, 5 µg/mL leupeptin, 1 µM E64, 100 mg/L glutathione). Protease inhibitors and glutathione were added just before use. The cell suspension (total volume about 60 mL) was kept on ice and sonicated with a macrotip 2 times (30 seconds each; output=7; duty=70%) with a Branson Sonifier 450. The whole cell lysate was centrifuged at 4° C. for 30 minutes at 11,000 rpm in a Beckman JA-14 rotor (18,600 g). The supernatant was removed (about 60 mL) and loaded onto a 2 mL Qiagen Nickel-NTA column (previously pre-washed and pre-equilibrated in lysis buffer) at 4° C. The column was washed with 20 mL wash buffer (lysis buffer plus 0.17 M NaCl plus 10 mM imidazole) at 4° C. Polypeptides were eluted with 2.5 mL of elution buffer (wash buffer plus 0.2 M imidazole). The molecular mass and purity of the recombinant polypeptide was verified by SDS-PAGE for each step in the purification. The eluate polypeptides were passed through a PD-10 column (Amersham Pharmacia Biotech, Piscataway, N.J.) and eluted in final storage buffer (50 mM Tris-HCl (pH 7.5), 0.5 mM EDTA, 100 mg/L glutathione, 10% glycerol). Total polypeptide concentrations were measured using the Bradford assay. Samples were aliquoted into 1 mL volumes, flash-frozen with liquid nitrogen, and placed at −70° C. until analyzed.

The eluate was purified to homogeneity as judged by SDS-PAGE analysis. MIO activity assays were performed on all of the fractions from the purification process using the methods described in Example 1. Results indicated that the purified polypeptide has a specific activity of 225 µg glucuronic acid formed per mg polypeptide during a 10 minute assay.

Example 6

Human Cells Containing Exogenous Nucleic Acid that Encodes a Human Polypeptide Having Myo-inositol Oxygenase Activity Human kidney embryonic cells (293 cells; ATCC catalog number CRL 1573) are maintained in DMEM supplemented with 10% fetal calf serum (GIBCO), 2 mM glutamine, 100 unit/mL penicillin, and 100 mg/mL streptomycin. A nucleic acid insert containing the human mio gene is introduced into the 293 cells using the general procedure described by Caruso et al. (*Proc. Natl. Acad. Sci USA*, 93:11302-11306 (1996)). Briefly, a vector is constructed to contain the human nucleic acid encoding the MIO enzyme described in Example 2 using a replication-defective adenoviral vector (ADV) under the transcriptional control of the Rous sarcoma virus long terminal repeat promoter (Accession Number gi:61690). The internal ribosome binding site (nucleotides 40-35) is obtained from the pCITE-1 vector (Novagen, Madison, Wis.) and is inserted into the E1 deleted adenovirus backbone pAd.1Rous sarcoma virus as described elsewhere (Fang et al., *Gene Ther.*, 1,:247-254 (1994)). Recombinant adenovirus is generated by cotransfection with pBHG10 in 293 cells as described by Bett et al. (*Proc. Natl. Acad. Sci USA*, 91:8802-8806 (1994)). Titers are calculated using a plaque assay (pfus).

Cells are seeded on a six-well plate (30,000-50,000/cm$^2$) using 0.25% trypsin. About one million cells are infected with the ADV/mio virus at various multiplicities of infection (e.g., about 200-1000) in a total volume of 0.5 mL. Infection is stopped after a two hour incubation at 37° C. by decanting the viral supernatant and adding 2.5 mL fresh cell medium. Cells are harvested after incubation at 37° C. for 48-72 hours and resuspended in lysis buffer (1×PBS (pH 7.4), 10% glycerol, 1 µg/mL pepstatin, 5 µg/mL leupeptin, 1 µM E64). The cell suspension is sonicated on ice and centrifuged (18,600 g) at 4° C. to remove cellular debris. The whole cell lysate is assayed for MIO activity as described in Example 1.

Example 7

Cloning Nucleic Acid that Encodes a *Cryptococcus neoformans* Polypeptide Having Myo-inositol Oxygenase Activity into *Cryptococcus neoformans*

A nucleic acid insert containing the *Cr. neoformans* mio gene is introduced into *Cr. neoformans* using the general procedure described by delpoeta et al. (*Infect. Immun.*, 67(4):1812-1820 (1999)). The nucleic acid encoding a *Cr. neoformans* polypeptide having MIO activity is amplified from a *Cr. neoformans* cDNA library (strain B3501; Stratagene catalog # 937052) using the Expand High Fidelity PCR system (Roche Molecular Biochemicals) and the following PCR primers: 5'-CACATCTAGAATGCA-CGCTC CCGAAGTCAA-3' (SEQ ID NO:13) and 5'-TTAA GGTACCCTACCACTG-CACCTCCTCAG-3' (SEQ ID NO:14). Restriction sites are underlined. The PCR conditions are as follows: (1) 94° C. for 5 minutes, (2) 94° C. for 30 seconds, (3) 55° C. for 60 seconds, (4) 72° C. for 1.5 minutes, (5) repeat steps 2-4 9 times, (6) 94° C. for 30 seconds, (7) 55° C. for 60 seconds, (8) 72° C. for 1.5 minutes (+5 seconds/cycle), (9) repeat steps 6-8 14 times, (10) 94° C. for 30 seconds, (11) 55° C. for 60 seconds, (12) 72° C. for 2.75 minutes, (13) repeat steps 10-12 9 times, and (14) 72° C. for 7 minutes. This PCR is used to produce a fragment (about 1 Kbp) that is digested with XbaI and KpnI and inserted into the XbaI/KpnI site of pUC19 to yield pMIO1.

The GAL7 promoter is amplified from genomic DNA (gDNA) of Cr. neoformans strain JEC21 (ATCC 96910) using the following PCR primers: 5'-GACCAAGCTTG TGGA-AAGAAGCAGGTCTTGTCGA-3' (SEQ ID NO: 15) and 5'-GGCTAAGCTTTCTCAAGAG-GGGATTGAG CGCTGA-3' (SEQ ID NO:16). Restriction sites are underlined. The PCR conditions are as follows: (1) 95° C. for 5 minutes, (2) 93° C. for 50 seconds, (3) 50° C. for 50 seconds, (4) 72° C. for 80 seconds, and (5) 72° C. for 2 minutes; with steps 2 through 4 being repeated 25 times. This PCR is used to produce a fragment (about 585 bp) that is digested with HindIII and inserted into the HindIII site of pMIO1 to yield pGAL7::MIO.

The Cr. neoformans phosphoribosylaminoimidazole carboxylase (ade2) gene amplified from a Cr. neoformans cDNA library (strain B3501; Stratagene catalog # 937052) is then inserted downstream from the MIO nucleic acid into the EcoRI site to yield pGAL7::MIO/ADE2. The ade2 gene is isolated using the following PCR primers: 5'-AATT GAATTCCCGGTGGACCA-AGTGGAAGC-3' (SEQ ID NO:17) and 5'-AATTGAATTCGCACAGACACCGCCG TACT-3' (SEQ ID NO:18). Restriction sites are underlined. The PCR conditions are as follows: (1) 95° C. for 5 minutes, (2) 93° C. for 50 seconds, (3) 50° C. for 50 seconds, (4) 72° C. for 3 minutes, and (5) 72° C. for 2 minutes; with steps 2 through 4 being repeated 30 times. This PCR is used to produce a fragment (about 2.5 Kbp) that is digested with EcoRI and inserted into the EcoRI site of pGAL7::MIO to yield pGAL7::MIO/ADE2.

The pGAL7::MIO/ADE2 construct is transformed into Cr. neoformans M001 (ATCC MYA-428; an ade2 auxotrophic mutant of strain H99) by biolistic delivery of DNA as described elsewhere (Toffaletti et al., J. Bacteriol., 175: 1405-1411 (1993)).

Adenine prototrophs are selected on synthetic medium (without adenine) supplemented with 1 M sorbitol at 30° C. Synthetic medium consists of (per liter) 6.7 g of yeast nitrogen base without amino acids (YNB w/o), 1.3 g of amino acid mix lacking adenine, 180 g of sorbitol, 20 g of galactose, and 20 g of agar. Adenine transformants are subcultured onto selective medium (YNB-galactose) and then are passaged twice on yeast extract-peptone-dextrose (YEPD) agar to select for stable transformants.

Example 8

Enzymatic Activities in Saccharomyces cerevisiae and Escherichia coli Cells

Nucleic acid molecules encoding the following polypeptides were cloned into Saccharomyces cerevisiae and Escherichia coli cells: (1) Sus scroffa glr (glucuronate reductase; gi:1703236), (2) Zymomonas mobilis ula (Gluconolactonase; gi:48654), (3) Fusarium oxysporum lha (lactonohydrolase, broad specificity; gi:3810872; AB010465.1), and (4) Rat glo (Gulono-γ-Lactone Oxidase, cDNA; NM_022220).

1. Sources of Template DNA

Fusarium oxysporum ATCC 48112 was grown on a potato sucrose medium and a glycerol corn steep liquor medium to early log, mid-log, and stationary phases at 26° C. with shaking at 270 rpm. The mycelia were harvested by centrifugation at 3500 rpm for 10 minutes, washed with 50 mM Tris-HCl, pH 7.0 buffer (cold), and spun again. The resulting washed pellets were quick frozen at −80° C. Using ten grams of mycelia, a custom cDNA library (Stratagene, Inc.; Uni-ZAP XR vector) was synthesized. The estimated amplified titer of the resulting custom cDNA library was $9.6 \times 10^9$ pfu/mL, the average insert size was 1.5 kB, and the insert size range was 0.80 to 2.2 kB.

Zymomonas mobilis ATCC 29191 was grown in the recommended ATCC culture, and the gDNA was isolated using the Promega gDNA isolation kit for Gram(−) organisms.

A commercial rat liver cDNA library (Clonetech, Inc.) was purchased for glo and glr cloning.

2. Cloning

All constructs were cloned into S. cerevisiae using the shuttle vector pYES2 (Invitrogen Life Technologies, Carlsbad, Calif.). The construct sequences all included a Kozak sequence (ATCATGG) where the bold letters denote the start codon. PCR primers were designed based on the GenBank sequences and included restriction sites for cloning into the multiple cloning site of pYES2. PCR primers for the lha gene from F. oxysporum were designed based on the sequence of the lactonohydrolase for the proposed mature form in which the first 20 amnino acids (leader sequence) have been cleaved (Kobayahi et al, Proc. Natl. Acad. Sci. USA, 95(22):12787-12793 (1998)). An ATG start codon was designed into the N-terminal primer preceding the codon GCT, encoding the 21$^{st}$ amino acid (Ala) of the immature polypeptide. The sequence of these primers is as follows:
N-terminal: 5'-CGCGGATCCATGGCTAAGCTTCCTTC-TACG-3' (SEQ ID NO:47)
 The BamH1 site is shown in italics, and the start codon is in bold type
C-terminal: 5'-CGACTCGAGCTAATCATAGAGCTTGG-GACC-3' (SEQ ID NO:48)
 The Xho1 site is shown in italics, and the stop codon is in bold type Amplification of the rat glo sequence by PCR was performed as described below for the pYES2 cloning using the following reaction mixture:
 2 μL rat liver cDNA library (Clontech Catalog # RL5004T)
 1 μL of 500 mM PCR primer (each)
 4 μL of 10 mM (each) dNTPs
 10 μL of 10× Deep Vent polymerase buffer
 4 μL of 100 MM MgSO$_4$
 0.5 μL of Deep vent polymerase (2 U/μl)
 78.5 μL H$_2$O The template, primers, buffer, and MgSO$_4$ were mixed and heated to 96° C. for 15 minutes. Tubes were then cooled on ice, and the dNTPs and DNA polymerase were added before placing reaction tubes in the thermocycler. The thermocycler protocol was as follows: (1) 96° C. for 3:30, (2) 96° C. for 0:45, (3) 55° C. for 1:15, (4) 72° C. for 4:00, (5) Repeat Steps 2-4 34 times, and (6) 72° C. for 10:00.

For all other clones, standard recombinant DNA techniques for PCR, purification of DNA, ligations, and transformations were carried out according to established procedures (Sambrook, Fritsch, Maniatis, 1989) or the vendors' protocols. Ligations were typically carried out using Roche T4 DNA ligase. Initial transformations were typically in *E. coli* DH10B ElectroMAX cells using the BioRad recommended procedure including recovery in SOC medium and plating on LB plates containing ampicillin at 100 µg/mL. The purified plasmids (Qiagen miniprep) were screened by restriction digestion and verified by dideoxynucleotide chain-termination DNA sequencing.

Differences were found in the sequences when compared to the sequences within GenBank®. For the *F. oxysporum* lha sequence, the following differences were identified: V33V (GTA→GTC); K108K (AAG→AAA); V142V (GTT→GTC); P145P (CCA→CCC); T149T (ACT→ACG); N154N (AAC→AAT); E160E (GAG→GAA); G163G (GGT→GGC); 181T (ACC insert); L184L (CTT→CTC); F189F (TTC→TTT); R191R (CGC→CCT); Q230Q (CAG→CAA); T238T (ACT→ACC); V241V (GTC→GTT); Y304Y (TAT→TAC); and R358R (AGG→AGA). For the *Z. mobilis* ula sequence, the following differences were identified: T2A (ACC→GCC; intentional from introduction of Kozak sequence); V16A (GTT→GCC); M17I (ATG→ATA); I20I (ATC→ATT); A25A (GCA→GCC); E34Q (GAG→CAG); I96I (ATT→ATC); I63V (CGT insertion); S237S (TCC→TCT); P238P (CCG→CCT); and D261D (GAT→GAC). For the Rat glo sequence, the following differences were identified: I85V (ATA→GTA); R168R (AGA→CGA); and Q189H (CAG→CAC). For the Rat glr sequence, the following differences were identified: T→A(ACG→GCG; intentional from introduction of Kozak sequence).

*S. cerevisiae* INVSc1 competent cells were prepared using an S.c. EasyComp™ Transformation Kit (Invitrogen Life Technologies, Carlsbad, Calif.), and pYES2 constructs were transformed into the INVSC1 competent cells using the same kit. Transformation reactions were plated on selective media (SC-ura), incubated for 2 days at 30° C., and analyzed by colony PCR.

All of the sequences were subcloned into pET30a. Primers were designed with restriction sites compatible for the multiple cloning site of pET30a, and the sequences were amplified by PCR using the pYES2 clones as template and Expand DNA polymerase (Roche).

The ligations and transformations into *E. coli* DH10B ElectroMAX cells were carried out as described above for the pYES2 constructs. After verification of the sequences by sequence analysis, the pET30a constructs were transformed into the expression host BLR(DE3) (Novagen) following the manufacturer's protocol. These constructs were verified by restriction digestion of the purified plasmids. The glo-pET30a construct was also transformed into Rosetta(DE3) cells (Novagen). This strain supplies tRNAs under the control of their native promoters for the rare codons AUA, AGG, AGA, CUA, CCC, and GGA on a compatible chloramphenicol-resistant plasmid.

Induction experiments with the pET30a/BLR(DE3) clones were carried out in LB medium containing 50 mg/L kanamycin. Induction experiments with the glo-pET30a/Rosetta(DE3) clone were carried out in LB medium containing 50 mg/L kanamycin and 34 mg/L chloramphenicol. The cultures were first grown at 37° C. with shaking at 225 rpm to an $OD_{650}$ between 0.5 and 0.8, and protein expression was induced by addition of IPTG. The lha-pET30a-BLR (DE3) culture was induced with 0.1 mM IPTG and incubated for 8 hours at 21° C. (to minimize inclusion body formation) followed by centrifugation at 12,000×g for 10 minutes to harvest the cells. The ula-pET30a-BLR(DE3) and glo-pET30a-Rosetta(DE3) cultures were induced with 0.025 mM IPTG and incubated at 30° C. for 4 hours before harvesting. The glr-pET30a-BLR(DE3) cultures were induced with 0.1 mM IPTG and incubated at 30° C. for 4 hours before harvesting.

Cell extracts were prepared using Novagen BugBuster reagent (5 mL reagent per 1 g WCW) containing 1 µL of benzonase protease per mL reagent and 5 µL of Calbiochem protease inhibitor set III per mL reagent. The cell suspension was incubated at room temperature for 15 minutes with gentle shaking followed by removal of the cell debris by centrifugation at 21,000×g for 20 minutes. Alternatively, cell extracts were also prepared by 2 passages through a mini-French pressure cell at 19,000 psi (Aminco) followed by centrifugation to remove the cell debris. After centrifugation, the supernatant (cell extract) was carefully removed, and the enzymes were purified by affinity chromatography using His-Bind 900 cartridges (Novagen). After elution from the His-Bind cartridge, each purified protein was desalted by passage through a Pharmacia disposable PD-10 column previously equilibrated with a buffer compatible with the assay buffer. For example, the fusion product of lha (His-LHA) was eluted with 100 mM PIPES, pH 7.0. The desalted cell extracts were used for SDS-PAGE analysis of soluble proteins and for enzyme assays.

GLR was assayed by following the loss of absorbance at 340 nm (loss of NADPH) using 0.3 mM NADPH, 10 mM glucuronic acid, and variable amount of enzyme in 100 mM sodium phosphate, pH 6.6 (Hayashi et al., *J. Biochem.*, 95:2223-2232 (1984)). 1-2 micromoles of NADPH were typically consumed per minute per mg protein.

GLO activity was assayed according to the procedure described by Nishikimi (*Methods in Enzymology*, 62:24-30 (1979)). The assay mixture contained, in 1 mL, 50 mM potassium phosphate buffer, pH 7.5, 2.5 mM L-gulono-γ-lactone, 1 mM EDTA, and enzyme. The reaction was initiated by the addition of either substrate or enzyme, and the mixture was incubated with shaking in air for 15 minutes at 37° C. The reaction was stopped by the addition of 0.1 mL 50% trichloroacetic acid, and the precipitated protein was removed by centrifugation. The product ascorbic acid was detected by the method described in Example 9. Briefly, 0.956 mL 2,2'-dipyridyl reagent was added to 0.15 mL of the supernatant solution, and the reaction mixture was incubated at 25° C. for 15 minutes. After 15 minutes, the sample was centrifuged to remove any precipitate, and the absorbance was read at 525 nm. The 2,2'-dipyridyl reagent contained 0.056 mL ortho-phosporic acid (85%), 0.75 mL 0.5% 2,2'-dipyridyl (prepared in hot $H_2O$), and 0.15 mL 1% $FeCl_3$ (in $H_2O$). Standards of ascorbic acid (1.0 µg to 10 µg) were run in parallel with the biological samples for a standard curve. One unit is defined as the quantity that catalyzes the formation of 1 nmol of L-ascorbic acid in 1 minute under the conditions described above. Specific activity is expressed as units per mg of protein (µmol/min/mg).

LHA activity was assayed according to the procedure described by Shimizu et al. (*Eur. J. Biochem.*, 209:383-390 (1992)). The standard assay mixture contained 100 mM PIPES-NaOH (pH 7.0), 150 mM pantoyl-γ-lactone, and enzyme in a final volume of 250 µL. After incubation at 30° C. for 30 minutes, the reaction was stopped by the addition of 250 µL methanol containing 2 mM EDTA (disodium salt). The supernatant obtained upon centrifugation at 21,000×g for 5 minutes was analyzed by HPLC. One unit (U) of enzyme is defined as the amount catalyzing the hydrolysis of 1 µmole pantoyl-γ-lactone per minute under standard assay conditions. Specific activity is defined as the units of enzyme activity of a protein fraction divided by the protein concentration of the fraction (mmole/min/mg).

All assay samples were filtered through a 0.45 µm filter and diluted into the calibration range of 10 µg/mL to 150 µg/mL for analysis by HPLC. Separation was accomplished using a Symmetry® C18 3.5 µm (4.6×75 mm) HPLC column from Waters Corporation, Ireland. The HPLC conditions were as follows: (1) Flow rate: 0.8 mL/min; (2) Column temp: Ambient; (3) Mobile Phase: 13% methanol pH 2.5 with triflouroacetic acid; and (4) Detection: UV @ 220 nm. Under these conditions, pantoic acid elutes at about 3.5 minutes while pantoyl-γ-lactone elutes at about 2.5 minutes.

Protein concentration was estimated using the BioRad Protein Assay and the manufacturer's microassay protocol. Bovine gamma globulin was used for the standard curve determination. This assay is based on the Bradford dye-binding procedure.

3. Results

The glo-pET30a, lha-pET30a, and glr-pET30a constructs expressed soluble polypeptides of the predicted molecular weight as judged by SDS-PAGE. In fact, about 5-10% of total protein in each cell extract was the expressed polypeptide. The ula-pET30a construct did not express a significant amount of polypeptide with the predicted molecular weight of the ULA fusion protein in a soluble form. The enzyme activity results were as follows:

| gene | enzyme | Specific Activity (purified protein) |
|---|---|---|
| GLR | glucuronate reductase | 1-3 µmol/min/mg |
| GLO | gulono-γ-lactone oxidase | 0.926 nmol/min/mg |
| LHA | uronolactonase | 250 nmol/min/mg |
| ULA | D-glucono-1,5-lactone lactonohydrolase | ND |

LHA was also assayed for the ability to catalyze the formation of gulonic acid from gulono-γ-lactone using the same protocol, substituting 150 mM gulono-γ-lactone for 150 mM pantoyl-γ-lactone. Analysis by HPLC showed that gulonic acid was formed. The complex shape of the gulonic acid peak did not allow accurate quantification of the product formation.

In addition, ULA was assayed for the ability to catalyze the hydrolysis of pantoyl-γ-lactone or gulono-γ-lactone. No product formation was detectable by HPLC. The lack of measurable activity may be due to the very low amount of soluble ULA formed after IPTG induction.

The amount of ascorbic acid secreted into the medium when induced cultures of glo-pET30a-Rosetta (DE3) were incubated with 1 mM gulono-γ-lactone in a mannitol minimal medium was measured as described in Example 9. After incubation for 7 hours at 30° C. and induction with 0.05 mM IPTG, the glo-pET30a-Rosetta (DE3) culture secreted 110.7 nmol of ascorbic acid per mL of fermentation broth versus 14.3 nmol secreted by the control culture of pET30a-Rosetta (DE3).

Example 9

Detection of Ascorbic Acid in Biological Samples

Ascorbic acid was measured in biological samples including fermentation broth and cell extracts using two methods. For ascorbic acid concentrations determined immediately after sampling, a colorimetric assay that follows the reduction of ferric (Fe(III)) to ferrous (Fe(II)) ions by ascorbic acid was used as described elsewhere (Zannoni et al., *Biochemical Medicine*, 11:41-48 (1974)). In this assay, the production of ferrous iron is measured by the formation of a 2,2'-dipyridyl-Fe(II) complex that absorbs at 525 nm. Briefly, 0.15 mL of biological sample was mixed with 0.956 mL 2,2'-dipyridyl reagent and incubated at 25° C. for 15 minutes. After 15 minutes, the sample was centrifuged to remove any precipitate, and the absorbance was read at 525 nm. 0.956 mL of 2,2'-dipyridyl reagent contained 0.056 mL ortho-phosporic acid (85%), 0.75 mL 0.5% 2,2'-dipyridyl (prepared in hot $H_2O$), and 0.15 mL 1% $FeCl_3$ (in $H_2O$). Standards of ascorbic acid (1.0 µg to 10 µg in 0.15 mL) were run in parallel with the biological samples for a standard curve.

Duplicate samples were stabilized for several hours or days after sampling using a method described elsewhere (Lykkesfeldt, *Analytical Biochemistry*, 282:89-93 (2000)). This method involves acidifying with 10% meta-phosphoric acid and freezing at –80° C. followed by gentle thawing and reducing with tris(2-carboxyethyl)phosphine hydrochloride at pH 6.2 just before analysis by HPLC. The pH was reduced following the treatment with tris(2-carboxyethyl)phosphine hydrochloride to minimize the oxidation of ascorbic acid during analysis. Briefly, the biological sample was mixed with an equal volume of 10% meta-phosphoric acid containing 2 mM EDTA and immediately frozen at –80° C. On the day of HPLC analysis, the sample was gently thawed. 0.1 mL of 2.5 mM tris(2-carboxyethyl)phosphine hydrochloride in 0.8 M Tris-HCl (pH 9.0) was added to 0.2 mL of thawed sample. After mixing, the solution was incubated at 25° C. for 5 minutes, and then the pH was adjusted to 4.7 by the addition of 0.7 mL of 0.46 M disodium hydrogen phosphate plus 0.27 M citric acid (pH 4.5). Before injection on the HPLC, all samples were filtered through 0.2 µm filters. The HPLC parameters were as follows: (1) Column: Shodex Asahipak NH2P-50 4E; (2) Eluent: A: 20 mM $NaH_2PO_4$+30 mM $H_3PO_4$ (pH 2.2) B:$CH_3CN$ 20A/80B isocratic gradient; (3) FlowRate: 1.0 mL/min; (4) Detector: UV @ 254 nm; (5) Temperature: Ambient; and (6) Retention Times: Erythorbic Acid=6.3 minutes, Ascorbic Acid=7.7 minutes.

Example 10

*E. coli* Construct and Vitamin C Production

*E. coli* DH10B ElectroMAX cells were purchased from Invitrogen Life Technologies, Inc (Carlsbad, Calif.). *E. coli* Rosetta(DE3) was purchased from Novagen (Madison, Wis.). *E. coli* strain GM48 (ATCC #39099) was purchased from American Type Culture Collection (Rockville, Md.). Electrocompetent GM48 cells were prepared by growing cultures to mid-log phase ($OD_{600}$=0.5-0.8) in LB medium and washing 3 times with equal volumes of ice-cold 10% glycerol followed by resuspension in ice-cold 10% glycerol at a ratio of 40 µL per 1 mL of original culture and rapid freezing of 40 µL aliquots at –80° C. *E. coli* expression vectors pETBlue-2 and pET 11a were purchased from Novagen (Madison, Wis.). Expand DNA polymerase and the Rapid DNA Ligation Kit was purchased from Roche Diagnostics Corp (Indianapolis, Ind.). Microbial growth media components were from Becton Dickinson Microbiology Systems (Sparks, Md.) or VWR Scientific Products (So. Plainfield, N.J.), and other reagents were of analytical grade or the highest grade commercially available. Primers were purchased from Integrated DNA Technologies, Inc. Restriction enzymes were from New England Biolabs, Inc (Beverly, Mass.). An Eppendorf Mastercycler Gradient thermal cycler was used for PCR experiments. UV-visible spectrometry was done using a Bio-Rad SmartSpec 3000 or a Molecular Devices SpectraMAX Plus spectrophotometer (Sunnyvale, Calif.). Electroporations were performed using a Bio-Rad Gene Pulser II system. Automated DNA sequencing was carried by SeqWright (Houston, Tex.).

Recombinant DNA techniques for PCR, purification of DNA, ligations, and transformations were carried out according to established procedures (e.g., Sambrook et al., Molecular Cloning (A Laboratory Manual) Second Edition, Cold Spring Harbor Laboratory Press (1989) and Manufacturers' Technical Bulletins).

A synthetic 3 gene operon composed of: 5'-rat glo, *Cryptococcus neoformans* mio, and rat glr -3' (glo_mio_glr) was constructed by the technique of overlap PCR as described by Ho et al. (*Gene*, 77(1):51-59 (1989)). Briefly, this technique allowed for the fusion of 3 independent DNA sequences (glo, mio, and glr) through the use of complimentary oligonucleotide primers and PCR to generate DNA fragments with overlapping ends. Primers for the synthesis of the rat glo, *Cr. neofeomans* mio, and rat glr sequences with appropriate overlapping sequences, Ribosomal Binding Sites (RBS), and restriction sites for the pETBlue-2 vector were designed. After PCR amplification and purification of the PCR product from 1% agarose gels, these products were combined in a second "fusion" PCR reaction in which the overlapping ends anneal. This overlap allows each strand to serve as a primer for the extension of the complimentary strand. The addition of oligonucleotide primers for the ends of the fused product (the forward primer for glo and the reverse primer for glr) allowed for simultaneous amplification of the fused product. Initial PCR amplification was accomplished using the corresponding pYES2 clones as templates. After purification of the PCR product from 1% agarose gels and restriction digestion with NheI/PacI of both the PCR products and the pETBlue-2 vector, the ligation was carried out using the Rapid DNA Ligation Kit (Roche). The ligation mix was desalted and then transformed into *E. coli* DH10B ElectroMAX cells using the BioRad recommended procedure for transformation of *E. coli* cells using 0.2 cm micro-electroporation cuvettes. After recovery in SOC medium, the transformation mixtures were plated on LB plates containing ampicillin (100 µg/mL), 5-bromo4-chloro-3-indolyl-beta-D-galactopyranoside (X-gal; 70 µg/mL), and isopropyl-beta-D-thiogalactopyranoside (IPTG; 80 µM). Plasmid DNA of white colonies picked from the LB+ampicillin+IPTG+X-gal plates was isolated from liquid cultures (5 mL 2×YT medium+ampicillin (100 µg/mL) grown overnight at 37° C.) and purified using a Qiagen mini-prep kit. The purified plasmids were screened by restriction digestion and verified by dideoxynucleotide chain-termination DNA sequencing. This construct was designated pETBlue-3.

The sequence for the forward primer for glo with NheI site and synthetic RBS was as follows: 5'-GGCGGCTAGC GAAGGAGATATACCATGGTCCAT-GGGTACAAAG-3' (SEQ ID NO:49). The sequence for the reverse primer for glo with SphI, XhoI sites and synthetic RBS was as follows: 5'-CTTCGGGAGCGTGCAT-GGTATAT*CTCCTTC*TGCA TGCTCGAGTTAGTAG-3' (SEQ ID NO:50). The sequence for the forward primer for mio with SphI, XhoI sites and synthetic RBS was as follows: 5'-CTACTAACTCGAGCAT-GCA*GAAGGAG*ATATACCATGCACGC-TCCCGAAGT C-3' (SEQ ID NO:51). The sequence for the reverse primer for mio with MluI and AscI sites and synthetic RBS was as follows: 5'-GAGGCCGCCATGGTA-TAT*CTCCTTC*ACG CGTGGCGCGCCTACCACTGCACCTCCTCAG-3' (SEQ ID NO:52). The sequence for the forward primer for glr with AscI and MluI sites and synthetic RBS was as follows: 5'-GGTAGGCGCGCCACGCGT*GAAGGAG*ATATAC-CA TGGCGGCCTCCAGTGTCCT-3' (SEQ ID NO:53). The sequence for the reverse primer for glr with PacI and XbaI sites was as follows: 5'-CGGCTTAATTAAT-GCGGC-CCTCTAGATCAGTAT-3' (SEQ ID NO:54). The italics indicate restriction sites, the bold lettering indicates the start and stop codons, and the underlined sequences indicate RBS sequences.

The *S. cerevisiae* genes ino1 and itr1 were amplified from *S. cerevisiae* genomic DNA by PCR and inserted into pETBlue-3 as MluI/AscI fragments between the mio and glr sequences. These constructs (pETBlue-3+ino1 and pET-Blue-3+itr1, respectively) were screened for correct orientation of the MluI/AscI fragment by MluI/AscI digestion. pETBlue-3, pETBlue-3+ino1, and pETBlue-3+itr1 were each transformed into electrocompetant *E. coli* strain GM48 (dam methylation (-)) using the BioRad recommended procedure for transformation of *E. coli* cells using 0.2 cm micro-electroporation cuvettes. After recovery in SOC medium, the transformation mixtures were plated on LB plates containing ampicillin (100 µg/mL). Plasmid DNA of colonies picked from the LB+ampicillin plates was isolated from liquid cultures, purified using a Qiagen mini-prep kit, and digested with XbaI. The glo_mio_glr, glo_mio_ino1_glr, and the glo_mio_itr1_glr operons were each purified from 1% agarose gel and ligated into XbaI/ Shrimp Alkaline Phosphatase digested pET11a. The ligation was carried out using the Rapid DNA Ligation Kit (Roche). The ligation mix was desalted and then transformed into *E. coli* DH10B ElectroMAX cells using the BioRad recommended procedure for transformation of *E. coli* cells using 0.2 cm micro-electroporation cuvettes. After recovery in SOC medium, the transformation mixtures were plated on LB plates containing ampicillin (100 µg/mL). Plasmid DNA of colonies picked from the LB+ampicillin plates was isolated from liquid cultures and purified using a Qiagen mini-prep kit. The purified plasmids were screened by restriction digestion and verified by dideoxynucleotide chain-termination DNA sequencing. The resulting constructs were designated pET11a-3, pET11a-3+ino1, and pET11a+itr1, respectively. Orientation of the operons in the pET11a vector was confirmed by restriction digest with BamHI.

The sequence for the forward primer for ino1 with AscI and SacII sites and synthetic RBS was as follows: 5'-CG-CAGGCGCGCCCCGCG*GAAGGAG*ATATAC-CATGTTA GTATCCTTGATTTA-3' (SEQ ID NO:55). The sequence for the reverse primer for ino1 with MluI and ApaI sites was as follows: 5'-GCAT-ACGCGTGGGCCCGTTACAACAATC TCTCTTCGAATCT-3' (SEQ ID NO:56). The sequence for the forward primer for itr1 with AscI and ApaI sites and synthetic RBS was as follows: 5'-CGCAGGCGCGC-CGGGCCC*GAAGGAG*ATATACCATGGGAATA-CACA TACCATA-3' (SEQ ID NO:57). The sequence for the reverse primer for itr1 with MluI and SacII sites was as follows: 5'-GCATACGCGTCCGCGGC-CTATATATCCTC-TATAATC-3' (SEQ ID NO:58). The italics indicate restriction sites, the bold lettering indicates the start and stop codons, and the underlined sequences indicate RBS sequences.

Transformation of the pET11a vector constructs into *E. coli* Rosetta(DE3) expression host was carried out according to procedures specified by Novagen and plated on LB+100 µg/mL ampicillin+34 µg/mL chloramphenicol. Colonies from each plate were picked and analyzed by plasmid isolation and gel visualization. One isolate from each construct was chosen for expression studies.

E. coli Rosetta(DE3) cells carrying one of the described vector constructs (PET11a-3, pET11a-3+ino1, or pET11a-3+itr1) and the pET11a parent vector were grown in glycerol defined media containing 100 µg/mL ampicillin+34 µg/mL chloramphenicol for 8 hours at 37° C. with shaking and placed at 4° C. overnight. The cells were pelleted by centrifugation at 3500×g for 10 minutes at 4° C., and the pellets were each suspended in 5 mL glycerol defined medium containing 100 µg/mL ampicillin+34 µg/mL chloramphenicol. The $OD_{600}$ of each resuspended culture was determined, and the amount of culture necessary to obtain an $OD_{600}$ of 0.08 to 0.16 in 30 mL of glycerol defined media containing 100 µg/mL ampicillin+34 µg/mL chloramphenicol was calculated. The calculated volume of cells was inoculated, and each construct was grown at 37° C. with shaking at 225 rpm for ~2.5 hours until the $OD_{600}$ of each culture reached ~0.6. Three mL aliquots of fermentation broth were removed and centrifuged to remove the cells. The supernatants were diluted with an equal volume of 10% meta-phosphoric acid containing 2 mM EDTA as described in herein to stabilize the ascorbic acid in the samples. Myo-inositol (pET11a, pET11a-3, and pET11a-3+itr1) or glucose (pET11a-3+ino1) was added to a final concentration of 1%. 10 µM ferrous ammonium sulfate and 100 µM IPTG were added to all cultures. After 3 and 6 hours, 3 mL aliquots of fermentation broth were removed and centrifuged to remove the cells. The supernatants were diluted with an equal volume of 10% meta-phosphoric acid to stabilize the ascorbic acid in the samples. Upon completion of the time course, all samples were reduced with tris(2-carboxyethyl) phosphine hydrochloride and assayed using the 2,2'-dipyridyl reagent.

Figure 19:
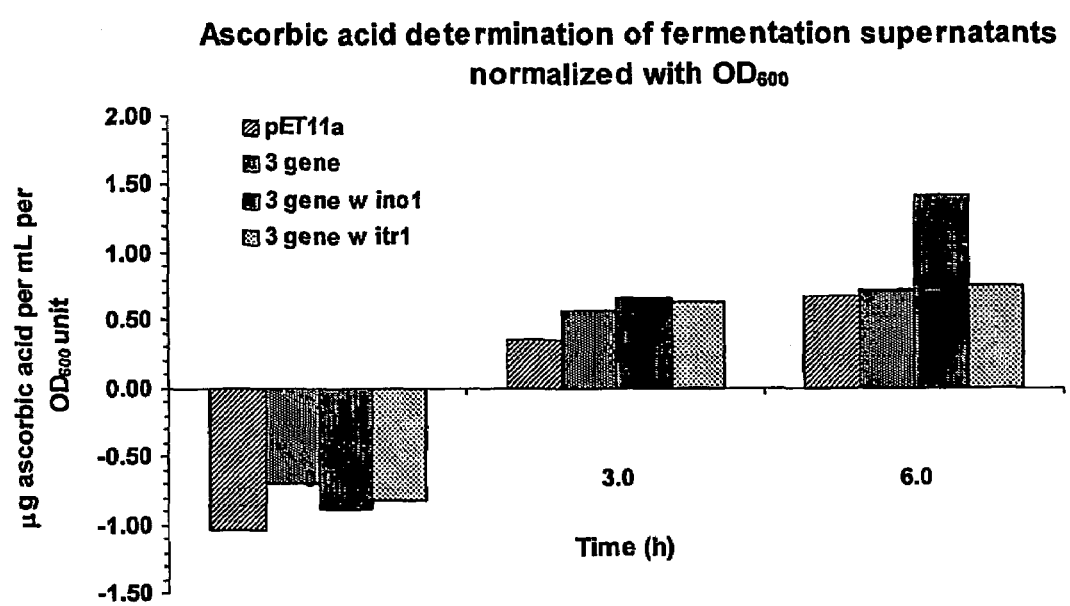
FIG. 19 is a graph plotting μg ascorbic acid per mL per OD600 unit for the indicated samples after a zero, three, or six hour incubation.

The concentration of ascorbic acid in the fermentation broth for each construct at each time point was divided by the $OD_{600}$ of the construct at that time point. As shown in FIG. 19, ascorbic acid was produced with all constructs. These results indicate that glo, glr, and mio can be used to produce ascorbic acid.

Example 11

Yeast Construct and Vitamin C Production

E. coli DH10B ElectroMAX cells were purchased from Invitrogen Life Technologies, Inc (Carlsbad, Calif.). S. cerevisiae strain YPH500 and the pESCleu and pESCtrp vectors were obtained from Stratagene, Inc (La Jolla, Calif.). Two genes can be cloned into each of these vectors. Each vector contains separate multiple cloning sites behind either a Gal1 or Gal10 promoter. Expand DNA polymerase and the Rapid DNA Ligation Kit was obtained from Roche Diagnostics Corp (Indianapolis, Ind.). Microbial growth media components were obtained from Becton Dickinson Microbiology Systems (Sparks, Md.) or VWR Scientific Products (So. Plainfield, N.J.). Other reagents were of analytical grade or the highest grade commercially available. Primers were purchased from Integrated DNA Technologies, Inc. Restriction enzymes were obtained from New England Biolabs, Inc (Beverly, Mass.). Electrophoresis was carried out using a Bio-Rad Protean II minigel system (protein) and a Bio-Rad Mini-Sub Cell GT system (DNA) (Bio-Rad Laboratories, Hercules, Calif.). An Eppendorf Mastercycler Gradient thermal cycler was used for PCR experiments. UV-visible spectrometry was done using a Bio-Rad SmartSpec 3000 or a Molecular Devices SpectraMAX Plus spectrophotometer (Sunnyvale, Calif.). Electroporations were performed using a Bio-Rad Gene Pulser II system. Automated DNA sequencing was carried by SeqWright (Houston, Tex.).

Recombinant DNA techniques for PCR, purification of DNA, ligations, and transformations were carried out according to established procedures. The sequences for GLO and/or (ULA or LHA) were cloned into a pESC-leu vector, while the sequences for GLR and MIO were cloned into a pESC-trp vector for dual transformation into the S. cerevisiae strain YPH500. Primers for the synthesis of the rat glo, rat glr, Cr. neoformans mio, Zymomonas mobilis ula, and Fusarium oxysporum lha sequences with appropriate restriction sequences for the pESC vectors 5' of each sequence's ATG start codon and 3' of each sequence's stop codon were designed for PCR amplification using the corresponding pYES2 clones as template.

The sequence for the forward primer for glo with SalI site was as follows: 5'-GGCCGTCGACCATAATGGTC-CATGGGTACA-3' (SEQ ID NO:59). The sequence for the reverse primer for glo with XhoI site was as follows: 5'-AATTCTCGAGTTAGTAGAAGACTTTCTCCAGGT-3' (SEQ ID NO:60). The sequence for the forward primer for glr with ApaI site was as follows: 5'-GGAA-GGGCCCAT-AATGGCGGCCTCCAGTGTCCTCCTGC-3' (SEQ ID NO:61). The sequence for the reverse primer for glr with HindIII site was as follows: 5'-GGCC-AAGCTTTAGAT-CAGTATGGGTCATTA-3' (SEQ ID NO:62). The sequence for the forward primer for ula with SpeI site was as follows: 5'-CCGGACTAGTA-TAATGGCCACTGGTCGTAT-3' (SEQ ID NO:63). The sequence for the reverse primer for ula with PacI site was as follows: 5'-GGCGTTAAAT-TAACC-CTCTAGATTACCAGAAAATAAG-3' (SEQ ID NO:64). The sequence for the forward primer for lha with SpeI site was as follows: 5'-CGGCACTAGTATAATG-GCTAAG-CTTCCTTCTACGGCTCAG-3' (SEQ ID NO:65). The sequence for the reverse primer for lha with PacI site was as follows: 5'-GGCCTTAAYTAAACTAAT-CATA-GAGCTTGGGACCCGAAGC-3' (SEQ ID NO:66). The sequence for the forward primer for mio with SpeI site was as follows: 5'-GGCCACTAGTATAATG-GACGCTC-CCGAAGTCA-3' (SEQ ID NO:67). The sequence for the reverse primer for mio with PacI site was as follows: 5'-GGCCTTAATTAATAGACTACCACTG-CACCTCCT-CAG-3' (SEQ ID NO:68). The italics indicate the restriction sites, while the bold lettering indicates the start and stop codons.

After purification of the PCR products from 1% agarose gels and restriction digestion of both the PCR products and the pESC vectors, the ligations were carried out using the Rapid DNA Ligation Kit (Roche). The ligation mixes were desalted and then transformed into E. coli DH10B Electro-MAX cells using the BioRad recommended procedure for transformation of E. coli cells using 0.2 cm micro-electroporation cuvettes. After recovery in SOC medium, the transformation mixtures were plated on LB plates containing ampicillin at 100 µg/mL. Plasmid DNA was isolated from liquid cultures (5 mL 2×YT medium+ampicillin (100 µg/ml) grown overnight at 37° C.) of colonies picked from the LB+ampicillin plates and purified using a Qiagen mini-prep kit. The purified plasmids were screened by restriction digestion and verified by dideoxynucleotide chain-termination DNA sequencing.

S. cerevisiae str. YPH500 competent cells were prepared using an S.c. EasyComp™ Transformation Kit (Invitrogen Corp, Carlsbad, Calif.). Aliquots (50 μL) were frozen at −80° C. and thawed just prior to use.

Transformation of the pESC vector constructs into *S. cerevisiae* str. YPH500 competent cells was carried out using the S.c. EasyComp™ Transformation Kit. The vector construct glo-pESCtrp, (glo+ula)-pESCleu, or (glo+lha) pESCleu was co-transformed with the (glr+mio)-pESCtrp vector construct. A 100 μL aliquot from each transformation reaction was spread on SC-leu-trp plates. The plates were incubated for 2 days at 30° C. Colonies from each plate were picked and analyzed by PCR. One isolate from each construct that generated the expected PCR products (evaluated by agarose gel electrophoresis) was chosen for expression studies.

*S. cerevisiae* str. YPH500 cells carrying one of the described vector constructs or the vectors without inserts were grown in 5 mL SC-trp-leu medium containing 2% raffinose and 0.2% glucose overnight at 30° C. with shaking. The cells were pelleted by centrifugation at 1500×g for 10 minutes, and the pellets were each suspended in 40 mL SC-leu-trp medium containing 2% raffinose. The resulting cell suspensions were incubated at 30° C. overnight with shaking. The $OD_{650}$ of each overnight culture was determined, and the amount of overnight culture necessary to obtain an $OD_{650}$ of 0.2 to 0.4 in 100 mL of SC-leu-trp containing 0.2% galactose (induction medium) was calculated. The calculated volume of cells was centrifuged at 1500×g for 10 minutes at 4° C., and the pellet was resuspended in 2 mL of induction medium and added to 150 mL induction medium containing 1% myo-inositol and 0.5% raffinose. Each construct was grown at 30° C. with shaking at 225 rpm from 0 to 19 hours. At 0, 4, 8, and 19 hours, aliquots of fermentation broth were removed and centrifuged to remove the cells. The supernatants were assayed for ascorbic acid using the 2,2'-dipyridyl reagent.

Figure 20:
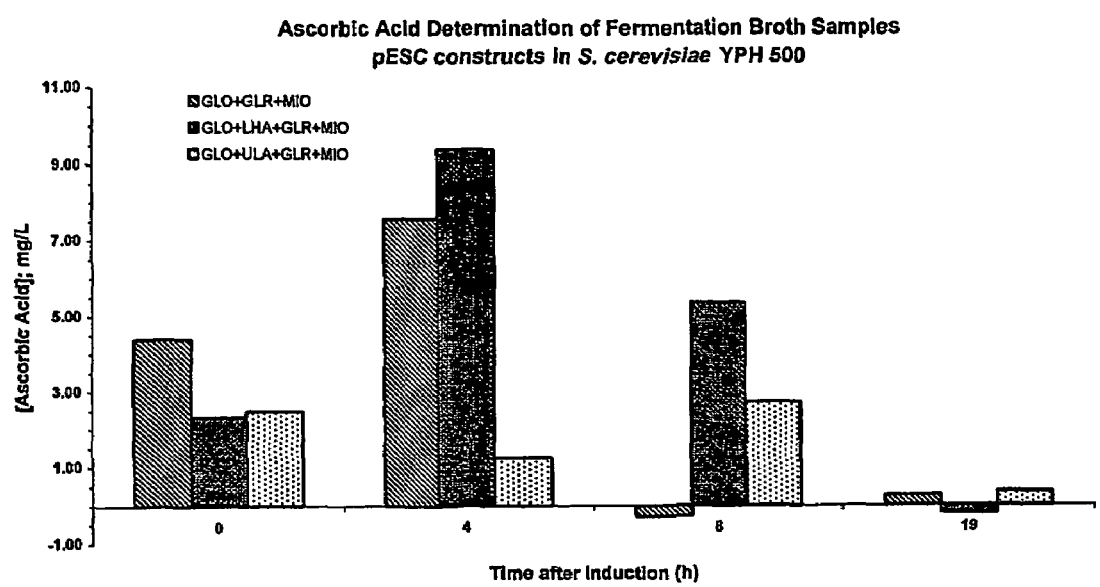
FIG. 20 is a graph plotting the concentration of ascorbic acid for the indicated samples after a zero, four, eight, or nineteen hour incubation.

The concentration of ascorbic acid in the vector control samples for each time point was subtracted from the values determined for the other samples. At 4 hours, the maximum amount of ascorbic acid was produced in the 3 sequence construct composed of glo, glr, and mio on the pESC vectors (7.9 mg/L supernatant) and the 4 sequence construct with the additional lha sequence (9.4 mg/L supernatant; FIG. 20). These results indicate that glo, glr, and mio can be used to produce ascorbic acid and that lha can enhance this production.

Example 12

Increasing Myo-inositol Oxygenase Activity in Vivo

An increase in the expression of mio in mammalian organs (e.g., human kidneys) is designed to lead to an increase in the production of glucuronic acid. The increased level of glucuronic acid produced resulting from mio expression is designed to lead to the increased production of glucaric acid through the use of an aldehyde dehydrogenase. This increased level of glucaric acid is designed to inhibit the activity of beta-glucuronidase, thus detoxifying toxic metabolites in the body.

Oligonucleotide primers homologous to the 5' and 3' ends of the human myo-inositol oxygenase (mio) sequence (GenBank Accession No. XM_010057; gi|18594511) are designed and used to amplify human mio from a human cDNA library by PCR. The sequence of the forward primer for mio with XbaI site is as follows: 5'-AATCTCTAGA-ATGAAGGTGACGGTGGGCCCAGAC-3' (SEQ ID NO:69). The sequence of the reverse primer for mio with KpnI site is as follows: 5'-CTATGGTACCTCACCAGCTC-AGGATGCC-3' (SEQ ID NO:70). The italics indicates restriction sites, and the bold lettering indicates the start and stop codons.

After purification of the PCR product from 1% agarose gels and restriction digestion with XbaI/KpnI of both the PCR products and the pSHUTTLE (Clontech) vector, the ligation is carried out using the Rapid DNA Ligation Kit (Roche). The ligation mix is desalted and then transformed into *E. coli* DH10B ElectroMAX cells using the BioRad recommended procedure for transformation of *E. coli* cells using 0.2 cm micro-electroporation cuvettes. After recovery in SOC medium, the transformation mixtures are plated on LB plates containing karamycin (50 μg/mL). Plasmid DNA of colonies picked from the LB+kanamycin is isolated from liquid cultures (5 mL 2×YT medium+kanamycin (50 μg/mL) grown overnight at 37° C.) and purified using a Qiagen mini-prep kit. The purified plasmids are screened by restriction digestion and verified by dideoxynucleotide chain-termination DNA sequencing. This construct is designated pSHUTTLE-mio.

pSHUTTLE-mio is digested with PI-SceI and I-CeuI and purified from 1% agarose gel. The resulting fragment containing the mio sequence is isolated and ligated into predigested Adeno-X viral DNA (Clontech). The ligation is carried out using the Rapid DNA Ligation Kit (Roche). The ligation mix is desalted, digested with SwaI, desalted, and then transformed into *E. coli* DH10B ElectroMAX cells using the BioRad recommended procedure for transformation of *E. coli* cells using 0.2 cm micro-electroporation cuvettes. After recovery in SOC medium, the transformation mixtures are plated on LB plates containing kanamycin (50 μg/mL). Plasmid DNA of colonies picked from the LB+kanamycin plates are isolated from liquid cultures (5 mL 2×YT medium+kanamycin (50 μg/mL) grown overnight at 37° C.) and purified using a Qiagen mini-prep kit. The purified plasmids are screened by restriction digestion and verified by dideoxynucleotide chain-termination DNA sequencing. The resulting construct is designated Adeno-X-mio.

Adeno-X-mio is transfected into low passage HEK 293 cells (Clontech), and adenoviral DNA is harvested in 4-7 days. 200 μL of Adeno-X-mio (>$10^{10}$ pfu/mL) is injected into the kidneys of 3 month old Fisher rats (experimental group) and 200 μL of Adeno-X (>$10^{10}$ pfu/mL) is injected into the kidneys of 3 month old Fisher rats (control group). Three days later, the rats of both the experimental and control groups are sacrificed, and the kidney tissue is assayed for mio activity as well as levels of glucuronic acid and glucaric acid. Levels of mio activity, glucaric acid, and glucuronic acid are compared between the experimental and control groups.

Example 13

Cloning and Expression of *B. subtilis* ycbD and ycbE Sequences into *E. coli*

*Bacillus subtilis* ATCC strain 6051 was purchased from ATCC. PfuTurbo DNA polymerase was from Stratagene (La Jolla, Calif.). Microbial growth media components were from Becton Dickinson Microbiology Systems (Sparks, Md.) or VWR Scientific Products (So. Plainfield, N.J.).

The ycbD (accession number 16077068; region gi|16077068:268838-270304) and ycbE (accession number 16077068; region gi|16077068:270388-271755) sequences from *B. subtilis* were cloned into the pET30a (Novagen) and pPRONde vectors. The pPRONde vector is a derivative of the pPROLAR.A122 vector (Clontech Laboratories, Inc) in which an NdeI site has been introduced at bp 132 by site-directed mutagenesis. The ycbD gene has been identified as encoding an aldehyde dehydrogenase, while the ycbE gene has been identified as encoding a glucaric acid transporter.

Primers with compatible restriction sequences with the pET30a and pPRONde multiple cloning sites 5' of the ycbD ATG start codon and 3' of the ycbE stop codon were designed, and the sequences were amplified by PCR using *B. subtilis* genomic DNA as template. A mixture of 4 parts Expand DNA polymerase and 1 part PfuTurbo DNA polymerase was used in the amplification reactions. The sequence of the forward primer with NdeI site was as follows: 5'-GCG ATT CCA TAT GTC TGT GAT CAC GGA ACA AAA CAC GTA C-3' (SEQ ID NO:71). The sequence of the reverse primer with BamHI site was as follows: 5'-GCG CGG ATC CAG GCT TAA TTA AGC TTA GAC AGG CAA CGA T-3' (SEQ ID NO:72). The italics indicate the restriction sequences, while the bold lettering indicates the start and stop codons.

Genomic DNA was purified from a culture of *Bacillus subtilis* ATCC strain 6051 grown at 30° C. in Nutrient Broth. The Qiagen genomic tip 100/G system was used to isolate the genomic DNA with the following changes from the manufacturer's protocol—the concentrations of proteinase K and lysozyme were doubled, and the incubation time with the enzymes was 2-3 times longer.

The intervening sequence between the ycbD and ycbE sequences contains an NdeI site. The individual ycbD and ycbE sequences were purified from a restriction digest (NdeI/BamHI) of the PCR product. The ycbD sequence was cloned into vectors pET30a and pPRONde previously digested with NdeI, while the ycbE sequence was cloned into pET30a and pPRONde previously digested with NdeI and BamHI. Both sequences were also cloned into pET30a sequentially. The ycbEpET30a construct was digested with NdeI followed by ligation with the NdeI digested ycbD gene. All restriction digests of the PCR products and plasmids were purified from 1% agarose gels. All ligations were carried out using the Rapid DNA Ligation Kit (Roche). The ligation mixes were desalted and transformed into *E. coli* DH10B ElectroMAX cells using the BioRad recommended procedure for transformation of *E. coli* cells using 0.2 cm micro-electroporation cuvettes. After recovery in SOC medium, the transformation mixtures were plated on LB plates containing 50 μg/mL kanamycin. Plasmid DNA was isolated from liquid cultures (5 mL 2×YT+kanamycin (50 μg/mL)) inoculated with colonies picked from the LB+kanamycin plates and grown overnight at 37° C. The plasmid DNA was purified using a Qiagen mini-prep kit. The purified plasmids were screened by restriction digestion and verified by dideoxynucleotide chain-termination DNA sequencing. One silent base change was found in the ycbD sequence compared to the GenBank sequence: C938A. One base change was detected in the ycbE sequence compared to the GenBank sequence: C499T, corresponding to a change in the amino acid sequence of P167S.

The pET30a constructs, verified by sequence analysis, were subcloned into the expression host BLR(DE3) (Novagen) following the manufacturer's protocol. These constructs were verified by restriction digestion of the purified plasmids.

Induction experiments with pET30a/BLR(DE3) clones were carried out in LB medium containing 50 mg/L kanamycin. The cultures were first grown at 37° C. with shaking at 225 rpm to an $OD_{650}$ between 0.5 and 0.8, and protein expression was induced by addition of 0.1 M IPTG. The cultures were incubated for 4 hours at 30° C. with shaking at 225 rpm and harvested by centrifugation at 21,000×g for 10 minutes. The proteins were analyzed by SDS-PAGE on 4-15% gradient gels to check for total and soluble protein levels at the predicted MW of the recombinant protein. Total protein samples were prepared by incubation of a cell pellet from 1 mL of culture with protein loading buffer (50 mM Tris-HCl, pH 8.8, 10% glycerol, 2.0% SDS, 100 mM dithiothreitol, 0.1% bromophenol blue) for 10 minutes at 95° C.

Cell extracts were prepared using Novagen BugBuster reagent (5 mL reagent per 1 g WCW) containing 1 μL of benzonase protease per mL reagent and 5 μL of Calbiochem protease inhibitor set III per mL reagent. The cell suspension was incubated at room temperature for 15 minutes with gentle shaking followed by removal of the cell debris by centrifugation at 21,000×g for 20 minutes. The supernatant (cell extract) was carefully removed and desalted by passage through a Pharmacia disposable PD-10 column previously equilibrated with 25 mL of 50 mM Tris-HCl, pH 8.0 containing 10 mM dithiothreitol. The proteins were eluted using the same buffer. The desalted cell extracts were used for SDS-PAGE analysis of soluble proteins and for enzyme assays.

The dehydrogenase activity of the cell extracts was followed using acetaldehyde, glucuronic acid, and glucurono-3,6-lactone as substrates in 96-well plates. Each assay mixture contained 100 mM potassium phosphate, pH 7.8, 1 mM NADP or NAD, 200 mM substrate, and between 0.02 and 0.1 mL cell extract (0.1 to 0.5 mg protein). The reactions were started by adding the enzyme and were incubated at 30° C. in the spectrophotometer. The dehydrogenase activity was followed by monitoring the linear change in absorbance at 340 nm over a 10 minute time period (referenced to a reaction mixture without substrate).

The products of ycbD and ycbE were expressed in significant amounts (~10% of total protein) in the pET30a constructs and were easily detected in the soluble protein fractions by SDS-PAGE. NADP was the preferred coenzyme for the dehydrogenase activity of the ycbD product for all substrates tested. Table III summarizes the enzyme activity for the cell extract from the [ycbd+ycde]-pET30a-BLR(DE3) construct measured with 0.05 mL cell extract (0.25 mg protein). Acetaldehyde was the best substrate of those tested followed by glucurono-3,6-lactone, and finally glucuronic acid. Potassium was not required for enzyme activity. When 200 mM Tris-HCl, pH 7.8, was used as the buffer, the rate of oxidation of the glucurono-3,6-lactone was slightly higher than when 100 mM potassium phosphate was used (other substrates not assayed).

TABLE III

Enzymatic activities in cell extracts containing the [ycbd + ycde]-pET30a-BLR(DE3) construct.

| Substrate | Relative Activity* | |
| --- | --- | --- |
| | NADP | NAD |
| acetaldehyde | 100.0 | 56.9 |
| D-glucuronate | 2.1 | 2.4 |
| D-glucurono-3,6-lactone | 50.6 | 2.1 |

*activity defined as percentage of maximum activity with acetaldehyde as the substrate and NADP as the coenzyme.

Example 14

Detecting Glucaric Acid in Biological Samples

The formation of glucaric acid in biological samples (both fermentation broth and cell extracts) is followed by HPLC. Two lactones, glucarate-1,4-lactone and glucarate-3,6-lactone, are in equilibrium with glucaric acid at neutral pH, and their formation is monitored as described elsewhere (Horton and Walaszek, *Carbohydrate Research*, 105:95-109 (1982)). Aliquots of the samples are sterile filtered through 0.2 μm filters before injection on the chromatography column. The HPLC parameters are as follows: (1) Column: Aminex APX-87H 300×7.0 mm BioRad; (2) Eluent: 0.005N $H_2SO_4$; (3) Flow Rate: 0.6 mL/min; (4) Detector: Refractive Index; (5) Temperature: 45° C.; (6) Retention Times: Glucaric-1,4-lactone=9.0 minutes, Glucaric-3,6-lactone=9.1 minutes, Glucaric acid=8.0 minutes, Glucurono-3,6-lactone=10.8 minutes, and Glucuronic acid=8.1 minutes.

Example 15

Enzymatic Formation of Glucaric Acid from Glucuronic Acid

Glucaric acid is synthesized from glucuronic acid in a reaction catalyzed by an enzyme with non-specific hexose oxidase activity (EC 1.1.3.5). The enzyme isolated from the red alga *Chondrus crispus* (AAB49376.1 GI:1877522) catalyzes this reaction at 2% the rate of the oxidation of glucose. Homologs of this enzyme with fasta probability scores (P-scores) greater than 4e-60 were identified in *Yersinia pestis* (NP_403959.1; gi:16120646), *Yersinia pseudotuberculosis* (Sangre Centre, gene sequence on Contig1834 (length 8,117), from 5,184 to 3,130), *Ralstonia solanacearum* (NP_518171.1; gi:17544769), and *Burkholderia pseudomallei* (Sangre Centre, gene sequence on Contig01233 (length 58,761), from 23,445 to 25,103) by BLAST analysis of the amino acid sequences.

The amount of glucaric acid formed by reaction of glucuronic acid with hexose oxidase is measured as described elsewhere (Sullivan and Ikawa, Biochimica et *Biophysica Acta*, 309:11-22 (1973) and U.S. Pat. No. 6,251,626). In this assay, the hydrogen peroxide formed during the oxidation of glucuronic acid in the presence of peroxidase reacts with a chromogenic substance, ortho-dianisidine to form a dye that absorbs at 402 nm.

The assay mixture consists of enzyme sample and 0.85 mL of an assay solution containing 0.370 mL of 0.1M sodium phosphate buffer, pH 7.0; 0.462 mL of D-glucuronic acid (varying concentrations) in 0.1M sodium phosphate buffer, pH 7.0; 0.009 mL of horseradish peroxidase (Sigma Chemicals, cat. no. P6782 or Boehringer Mannheim, cat. no. 814 393), 0.1 mg/mL in water; and 0.009 mL of ortho-dianisidine 2HCl (3,3'-dimethoxybenzidine, Sigma Chemicals), 3.0 mg/mL in water. After incubation at room temperature for 15 to 30 minutes, the assay is stopped by addition of one drop of 37% HCl. Samples of 0.100 mL are transferred from the assay tubes to the wells of a microtiter plate, and the absorbance at 410 nm is read using a Molecular Devices SpectraMAX Plus spectrophotometer (Sunnyvale, Calif.). One enzyme unit is defined as the amount of enzyme that catalyzes the production of 1 nmole hydrogen peroxide per min at 25° C., pH 6.3, at a substrate concentration of 0.05 M.

Example 16

Chemical Conversion of Glucuronic Acid to Glucaric Acid

The following method was used to convert glucuronic acid into glucaric acid. 5% Pd on carbon catalyst (10 g; 5% Pd/C catalyst; Johnson Matthey Inc., Ward Hill, Mass.) was placed in a 3-neck flask with 50 mL of distilled water. Oxygen was bubbled through the mixture for about 15 minutes. Meanwhile, 5 g of glucuronic acid was dissolved in 25 mL of distilled water, and the pH was adjusted to 8 by the addition of 10% sodium hydroxide. The glucuronate solution was then added to the flask containing the catalyst. The flask was placed in an oil bath at 50° C. and equipped with a dropping funnel containing 10% sodium hydroxide, a pH electrode, and an oxygen line with a metal frit. The reaction mixture was stirred at 50° C., while continuously bubbling oxygen through the mixture and monitoring the pH. The 10% sodium hydroxide was added periodically to maintain the pH above 8. After 10 hours, the catalyst was filtered off, and the reaction mixture analyzed by HPLC.

FIG. 21A depicts the LC-MS chromatogrms of the starting material, glucuronic acid, the product, glucaric acid, and the reaction mixture at 10 hours. FIG. 21B depicts the corresponding mass spectra. The reaction yield was determined to be greater than 90% by comparison of the ionization fragments at 146.1 (major daughter fragment of glucaric acid) and 140.4 (major daughter fragment of glucuronic acid) in the mass spectrum of the reaction mixture. These results demonstrate that chemically- or enzymatically-derived glucuronic acid can be converted in high yield to glucaric acid, by catalytic oxidation.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of oxidizing myo-inositol to glucuronic acid, said method comprising:
    transforming an isolated cell with a nucleic acid molecule encoding a polypeptide having a sequence at least 95 percent identical to SEQ ID NO 19, wherein the polypeptide has myo-inositol oxygenase activity, and wherein said isolated cell expresses said polypeptide;
    extracting said polypeptide from the isolated cells; and
    contacting said polypeptide with myo-inositol such that the myo-inositol is oxidized to glucuronic acid.

2. The method of claim 1, wherein said isolated cell is a prokaryotic cell.

3. The method of claim 2, wherein said prokaryotic cell is selected from the group consisting of *Eseherichia, Pseudomonas, Bacillus, Lactobacillus, Lactococcus,* and *Corynebacterium* cells.

4. The method of claim 1, wherein said isolated cell is a eukaryotic cell.

5. The method of claim 4, wherein said eukaryotic cell is selected from the group consisting of yeast, fungi, insect, and mammalian cells.

6. The method of claim 1, wherein said isolated cell is selected from the group consisting of *Saccharomyces, Pichia, Aspergillus, Cryptococcus, Schwanniomyces, Schizosaccharomyces, Spodoptera, Cricetulus,* and *Homo sapiens* cells.

7. The method of claim 1, wherein said nucleic acid molecule is integrated into the genome of said isolated cell.

8. The method of claim 1, wherein said polypeptide comprises an amino acid sequence at least 99 percent identical to the amino acid sequence of SEQ ID NO: 19.

9. The method of claim 1, wherein said polypeptide comprises an amino acid sequence at least 98 percent identical to the amino acid sequence of SEQ ID NO: 19.

10. The method of claim 1, wherein said isolated cell produces L-ascorbic acid or glucaric acid.

11. The method of claim 1, wherein said isolated cell comprises glucuronate reductase activity.

12. The method of claim 1, wherein said isolated cell comprises 1,4-lactone hydroxyacyihydrolase activity, D-glucono-1,5-lactone lactonohydrolase activity, or uronolactonase activity.

13. The method of claim 1, wherein said isolated cell comprises gulono-γ-lactone oxidase activity, galactono-γ-lactone oxidase activity, hexose oxidase activity, or gulono-γ-lactone dehydrogenase activity.

14. The method of claim 1, wherein said isolated cell comprises phosphatase activity.

15. The method of claim 1, wherein said isolated cell comprises phytase activity.

16. The method of claim 1, wherein said isolated cell lacks L-gulonate 3-dehydrogenase activity.

17. The method of claim 1, wherein said isolated cell comprises myo-inositol oxygenase activity with a specific activity greater than 40 mg glucuronic acid per gram dry cell weight per hour.

18. The method of claim 1, wherein isolated said cell comprises myo-inositol oxygenase activity such that an extract from $1 \times 10^6$ cells comprises a specific activity greater than 150 µg glucuronic acid formed per 10 mg total protein per 10 minutes, wherein each of said $1 \times 10^6$ cells is said cell or a progeny of said cell.

19. The method of claim 1, wherein said polypeptide lacks an N-terminal polyhistidine tag.

20. The method of claim 1, wherein said polypeptide lacks glutathione-S-transferase sequence.

21. The method of claim 1, wherein said polypeptide comprises the amino acid sequence of SEQ ID NO:19.

22. The method of claim 1, wherein said polypeptide consists of the amino acid sequence of SEQ ID NO:19.

23. A method of oxidizing myo-inositol to glucuronic acid, comprising:
    transforming an isolated cell which produces myo-inositol with a nucleic acid molecule encoding a polypeptide having a sequence at least 95 percent identical to SEQ ID NO 19, wherein the polypeptide has myo-inositol oxygenase activity, wherein said isolated cell expresses said polypeptide, and wherein culturing said transformed cell to express said polypeptide and oxidize said myo-inositol into glucuronic acid.

24. A method of oxidizing myo-inositol to glucuronic acid, said method comprising:
    transforming an isolated cell with at least one nucleic acid molecule, wherein said at least one nucleic acid molecule encodes at least two polypeptides,
    a first polypeptide having myo-inositol monophosphatase activity (E.C. 3.1.3.25) or having myo-inositol-1 phosphate synthase activity (E.C. 5.5.1.4),
    and a second polypeptide comprising at least 95% sequence identity to SEQ ID NO: 19, wherein the second polypeptide comprises myo-inositol oxygenase activity (E.C. 1.13.99.1),
    and wherein said isolated cell comprises myo-inositol-1-phosphtase, myo-inositol, and glucuronic acid, thereby permitting oxidation of myo-inositol to glucuronic acid.

25. The method of claim 24, wherein the polypeptide having myo-inositol monophosphatase activity is encoded by SEQ ID NO: 73.

26. The method of claim 24, wherein the polypeptide having myo-inositol-1 phosphate synthase activity is encoded by SEQ ID NO: 74.

* * * * *

SEQUENCE LISTING

<160> NUMBER OF SEQ ID NOS: 72

<210> SEQ ID NO 1
<211> LENGTH: 948
<212> TYPE: DNA
<213> ORGANISM: Cryptococcus neoformans -continued

```
<400> SEQUENCE: 1
atgcacgctc ccgaagtcaa cgactacatc aagcacaagg ctgttaagct cgaccaggtt    60
tctgacgaaa tcgacgaggt caatgtcttg aagctcaagc agaaggacgc tgtcgagaag   120
actcaagctg agatcgatta cgacctcgcg agcaagtttg accaagagaa ggacaaggct   180
gctttcaggc agtacgagga agcttgcgac cgtgtcaaga acttctacgc tgagcaacac   240
ttgaagcaga cctacgagta caatgtaaag atccgacaag aattccgcaa cactgtccgt   300
gctcgcatgt ccatctggga agcaatggag ctcctcgaca atctcgtcga cgagtccgac   360
cctgacacct ctgttggaca gattgagcac cttcttcaga ccgctgaggc tattcgacga   420
gacggcaagc tgaatggat gcaagtcacc ggtttgattc acgatcttgg caagcttctc   480
tgtttcttcg gtgccgacgg tcagtgggac gttgtcggtg acaccttcgt tgtcggctgc   540 aagtttccg acaagattat ctaccccgac accttcaagt ctaaccccga ctataacaac   600
cccaagttga acaccaagta cggtgtctat gagcctaact gcggtttgga caacgtcttg   660
ctcagctggg gtcacgatga gtacatgtac gagatctgca agaaccaatc tactcttccc   720
caagaagctc ttgctatgat ccgatatcac tctttctacc cctggcaccg agagggtgcc   780
tacgagcatc tcatgaacga aaggactac tcacagctca aggctgtcaa ggctttcaac   840
ccctacgacc tctattccaa gtctgacgac ccccccaaga aggaggagct caagccttac   900
taccaaagcc tcatctccaa attcttccct gaggaggtgc agtggtag              948
```

```
<210> SEQ ID NO 2
<211> LENGTH: 18
<212> TYPE: PRT
<213> ORGANISM: Artificial Sequence
<220> FEATURE:
<223> OTHER INFORMATION: Consensus Sequence

<400> SEQUENCE: 2

Asp Gly Lys Pro Glu Trp Met Gln Val Thr Gly Leu Val His Asp Leu
 1               5                  10                  15

Gly Lys
```

```
<210> SEQ ID NO 3
<211> LENGTH: 18
<212> TYPE: PRT
<213> ORGANISM: Artificial Sequence
<220> FEATURE:
<223> OTHER INFORMATION: Consensus Sequence

<400> SEQUENCE: 3

Asp Gly Lys Pro Glu Trp Met Gln Val Thr Gly Leu Val His Asp Leu
 1               5                  10                  15

Gly Lys
```

```
<210> SEQ ID NO 4
<211> LENGTH: 9
<212> TYPE: PRT
<213> ORGANISM: Artificial Sequence
<220> FEATURE:
<223> OTHER INFORMATION: Consensus Sequence

<400> SEQUENCE: 4

Tyr His Ser Phe Tyr Pro Trp His Arg
 1               5
```

```
<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
ggccggtacc atggacgctc ccgaagtcaa                              30

<210> SEQ ID NO 6
<211> LENGTH: 29
<212> TYPE: DNA
<213> ORGANISM: Artificial Sequence
<220> FEATURE:
<223> OTHER INFORMATION: primer

<400> SEQUENCE: 6
cgcctcgagc taccactgca cctcctcag                               29

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
gcgctctaga ctaccactgc acctcctcag                              30

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
atatccatgg aggtgacggt gggcccagac                              30

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9
ctattctaga tcaccagctc aggatgcc                                28

<210> SEQ ID NO 10
<211> LENGTH: 34
<212> TYPE: DNA
<213> ORGANISM: Artificial Sequence
<220> FEATURE:
<223> OTHER INFORMATION: primer

<400> SEQUENCE: 10
aattggtacc atggaggtga cggtgggccc agac                         34

<210> SEQ ID NO 11
<211> LENGTH: 28
<212> TYPE: DNA
<213> ORGANISM: Artificial Sequence
<220> FEATURE:
<223> OTHER INFORMATION: primer
```

-continued

```
<210> SEQ ID NO 12
<211> LENGTH: 310
<212> TYPE: PRT
<213> ORGANISM: Artificial Sequence
<220> FEATURE:
<223> OTHER INFORMATION: human polypeptide with non-human sequences

<400> SEQUENCE: 12

Met Ser Tyr Tyr His His His His His His Asp Tyr Asp Ile Pro Thr
1               5                   10                  15

Thr Glu Asn Leu Tyr Phe Gln Gly Ala Met Glu Val Thr Val Gly Pro
            20                  25                  30

Asp Pro Ser Leu Val Tyr Arg Pro Asp Val Asp Pro Glu Val Ala Lys
        35                  40                  45

Asp Lys Ala Ser Phe Arg Asn Tyr Thr Ser Gly Pro Leu Leu Asp Arg
    50                  55                  60

Val Phe Thr Thr Tyr Lys Leu Met His Thr His Gln Thr Val Asp Phe
65                  70                  75                  80

Val Arg Ser Lys His Ala Gln Phe Gly Gly Phe Ser Tyr Lys Lys Met
                85                  90                  95

Thr Val Met Glu Ala Val Asp Leu Leu Asp Gly Leu Val Asp Glu Ser
            100                 105                 110

Asp Pro Asp Val Asp Phe Pro Asn Ser Phe His Ala Phe Gln Thr Ala
        115                 120                 125

Glu Gly Ile Arg Lys Ala His Pro Asp Lys Asp Trp Phe His Leu Val
    130                 135                 140

Gly Leu Leu His Asp Leu Gly Lys Val Leu Ala Leu Phe Gly Glu Pro
145                 150                 155                 160

Gln Trp Ala Val Val Gly Asp Thr Phe Pro Val Gly Cys Arg Pro Gln
                165                 170                 175

Ala Ser Val Val Phe Cys Asp Ser Thr Phe Gln Asp Asn Pro Asp Leu
            180                 185                 190

Gln Asp Pro Arg Tyr Ser Thr Glu Leu Gly Met Tyr Gln Pro His Cys
        195                 200                 205

Gly Leu Asp Arg Val Leu Met Ser Trp Gly His Asp Glu Tyr Met Tyr
    210                 215                 220

Gln Val Met Lys Phe Asn Lys Phe Ser Leu Pro Pro Glu Ala Phe Tyr
225                 230                 235                 240

Met Ile Arg Phe His Ser Phe Tyr Pro Trp His Thr Gly Arg Asp Tyr
                245                 250                 255

Gln Gln Leu Cys Ser Gln Gln Asp Leu Ala Met Leu Pro Trp Val Arg
            260                 265                 270

Glu Phe Asn Lys Phe Asp Leu Tyr Thr Lys Cys Pro Asp Leu Pro Asp
        275                 280                 285

Val Asp Lys Leu Arg Pro Tyr Tyr Gln Gly Leu Ile Asp Lys Tyr Cys
    290                 295                 300

Pro Gly Ile Leu Ser Trp
305                 310

<210> SEQ ID NO 13
<211> LENGTH: 30
<212> TYPE: DNA
<213> ORGANISM: Artificial Sequence
```

```
<220> FEATURE:
<223> OTHER INFORMATION: primer

<400> SEQUENCE: 13
cacatctaga atgcacgctc ccgaagtcaa                                    30

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
ttaaggtacc ctaccactgc acctcctcag                                    30

<210> SEQ ID NO 15
<211> LENGTH: 34
<212> TYPE: DNA
<213> ORGANISM: Artificial Sequence
<220> FEATURE:
<223> OTHER INFORMATION: primer

<400> SEQUENCE: 15
gaccaagctt gtggaaagaa gcaggtcttg tcga                               34

<210> SEQ ID NO 16
<211> LENGTH: 34
<212> TYPE: DNA
<213> ORGANISM: Artificial Sequence
<220> FEATURE:
<223> OTHER INFORMATION: primer

<400> SEQUENCE: 16
ggctaagctt tctcaagagg ggattgagcg ctga                               34

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17
aattgaattc ccggtggacc aagtggaagc                                    30

<210> SEQ ID NO 18
<211> LENGTH: 30
<212> TYPE: DNA
<213> ORGANISM: Artificial Sequence
<220> FEATURE:
<223> OTHER INFORMATION: primer

<400> SEQUENCE: 18
aattgaattc gcacagacac cgcccgtact                                    30

<210> SEQ ID NO 19
<211> LENGTH: 263
<212> TYPE: PRT
<213> ORGANISM: Cryptococcus neoformans

<400> SEQUENCE: 19

Met His Ala Pro Glu Val Asn Asp Tyr Ile Lys His Lys Ala Val Lys
 1               5                  10                  15

Leu Asp Gln Val Ser Asp Glu Ile Asp Glu Val Asn Val Leu Lys Leu
```

```
            20                  25                  30
Lys Gln Lys Asp Ala Val Glu Lys Thr Gln Ala Glu Ile Asp Tyr Asp
            35                  40                  45

Leu Ala Ser Lys Phe Asp Gln Glu Lys Asp Lys Ala Ala Phe Arg Gln
 50                  55                  60

Tyr Glu Glu Ala Cys Asp Arg Val Lys Asn Phe Tyr Ala Glu Gln His
 65                  70                  75                  80

Leu Lys Gln Thr Tyr Glu Tyr Asn Val Lys Ile Arg Gln Glu Phe Arg
                 85                  90                  95

Asn Thr Val Arg Ala Arg Met Ser Ile Trp Glu Ala Met Glu Leu Leu
             100                 105                 110

Asp Asn Leu Val Asp Glu Ser Asp Pro Asp Thr Ser Val Gly Gln Ile
             115                 120                 125

Glu His Leu Leu Gln Thr Ala Glu Ala Ile Arg Arg Asp Gly Lys Pro
             130                 135                 140

Glu Trp Met Gln Val Thr Gly Leu Ile His Asp Leu Gly Lys Leu Leu
145                 150                 155                 160

Cys Phe Phe Gly Ala Asp Gly Gln Trp Asp Val Val Gly Asp Thr Phe
                 165                 170                 175

Val Val Gly Cys Lys Phe Ser Asp Lys Ile Ile Tyr Pro Asp Thr Phe
             180                 185                 190

Lys Ser Asn Pro Asp Tyr Asn Asn Pro Lys Leu Asn Thr Lys Tyr Gly
             195                 200                 205

Val Tyr Glu Pro Asn Cys Gly Leu Asp Asn Val Leu Leu Ser Trp Gly
         210                 215                 220

His Asp Glu Tyr Met Tyr Glu Ile Cys Lys Asn Gln Ser Thr Leu Pro
225                 230                 235                 240

Gln Glu Ala Leu Ala Met Ile Arg Tyr His Ser Phe Tyr Pro Trp His
                 245                 250                 255

Arg Glu Gly Ala Tyr Glu His
             260

<210> SEQ ID NO 20
<211> LENGTH: 262
<212> TYPE: PRT
<213> ORGANISM: Arabidopsis thaliana

<400> SEQUENCE: 20

Met Asn Ile Ser Val Glu Asn Pro Val Phe Val His Glu Asp Ser Thr
 1               5                  10                  15

Thr Gln Lys Thr Gly Glu Leu Arg Leu Asp Ser Asp Ile Pro Met Ser
                 20                  25                  30

Lys Ile Ser Ser Asp Asp Glu Val Phe Leu Ala Pro Glu Met Asn Ala
             35                  40                  45

Phe Gly Arg Gln Phe Arg Asp Tyr Thr Asp Thr Asn Ser Glu Arg Gln
         50                  55                  60

Lys Ser Val Glu His Phe Tyr Ala Thr Gln His Thr Asn Gln Thr Leu
 65                  70                  75                  80

Asp Phe Val Gln Lys Met Arg Ser Glu Tyr Gly Lys Leu Asp Lys Met
                 85                  90                  95

Val Met Asn Ile Trp Glu Cys Cys Glu Leu Leu Lys Glu Val Val Asp
             100                 105                 110

Glu Ser Asp Pro Asp Leu Asp Glu Pro Gln Ile Gln His Leu Leu Gln
             115                 120                 125
```

```
Ser Ala Glu Ala Ile Arg Lys Asp Tyr Pro Asn Glu Asp Trp Leu His
    130                 135                 140

Leu Thr Ala Leu Ile His Asp Leu Gly Lys Val Leu Thr Leu Pro Gln
145                 150                 155                 160

Phe Gly Gly Leu Pro Gln Trp Ala Val Val Gly Asp Thr Phe Pro Val
                165                 170                 175

Gly Cys Ala Phe Asp Glu Ser Asn Val His His Lys Tyr Phe Met Glu
                180                 185                 190

Asn Pro Asp Phe Asn Asn Pro Lys Tyr Asn Thr Lys Ala Gly Ile Tyr
            195                 200                 205

Ser Glu Gly Cys Gly Leu Glu Asn Val Leu Met Ser Trp Gly His Asp
    210                 215                 220

Asp Tyr Met Tyr Leu Val Ala Lys Glu Asn Gly Ser Thr Leu Pro Ser
225                 230                 235                 240

Pro Gly Leu Phe Ile Ile Arg Tyr His Ser Phe Tyr Pro Leu His Lys
                245                 250                 255

Ala Gly Ala Tyr Thr His
            260

<210> SEQ ID NO 21
<211> LENGTH: 161
<212> TYPE: PRT
<213> ORGANISM: Colletotrichum gloeosporioides

<400> SEQUENCE: 21

Met Thr Ile Trp Glu Ala Met Glu Lys Leu Asn Thr Leu Ile Asp Asn
1               5                   10                  15

Ser Asp Pro Asp Thr Glu Leu Ser Gln Ile Gln His Leu Leu Gln Thr
            20                  25                  30

Ala Glu Ala Met Arg Arg Asp Gly Lys Pro Arg Trp Met Gln Leu Thr
        35                  40                  45

Gly Leu Ile His Asp Leu Gly Lys Leu Leu Phe Phe Tyr Gly Ala Glu
    50                  55                  60

Gly Gln Trp Asp Val Val Gly Asp Thr Phe Pro Val Gly Cys Ala Phe
65                  70                  75                  80

Asp Asn Arg Ile Val Leu Pro Thr Thr Phe Glu Gly Asn Pro Asp Ile
                85                  90                  95

His His Pro Val Tyr Ser Thr Lys His Gly Ile Tyr Lys Pro Gly Cys
            100                 105                 110

Gly Ile Glu Asn Leu Met Ile Ser Trp Gly His Asp Glu Tyr Met Tyr
        115                 120                 125

Thr Val Cys Lys Glu Gln Ser Lys Leu Pro Arg Glu Ala Leu Ala Met
    130                 135                 140

Ile Arg Tyr His Ser Phe Tyr Pro Trp His Arg Glu Gly Ala Tyr Arg
145                 150                 155                 160

Glu

<210> SEQ ID NO 22
<211> LENGTH: 246
<212> TYPE: PRT
<213> ORGANISM: Nostoc punctiforme

<400> SEQUENCE: 22

Met Ser Gln Ile Leu Gln Asn Phe Ile Lys Gln Ala Gln Tyr Asn Pro
1               5                   10                  15

Leu His Ser Leu Glu Glu Trp Glu Glu Asp Leu Leu Asn Arg Tyr Pro
```

```
                20                  25                  30
Asp Pro His Ser Ile Val Lys Glu Gly Lys Thr Thr Gln Glu Tyr Arg
         35                  40                  45

Asn Tyr Glu Thr Pro Thr Arg Glu Thr Val Lys Glu Phe Tyr Arg Leu
 50                  55                  60

Asn His Ile Asn Gln Thr Tyr Asn Phe Val Leu Glu Lys Glu Lys Asn
 65                  70                  75                  80

Phe Leu Lys Phe Asp Lys Lys Glu Met Ser Val Trp Asp Ala Val Glu
                 85                  90                  95

Phe Leu Asn Gln Leu Val Asp Asp Ser Asp Pro Asp Thr Glu Met Asp
             100                 105                 110

Gln Leu Gln His Leu Leu Gln Thr Ser Glu Ala Ile Arg Ala Asp Gly
         115                 120                 125

His Pro Asp Trp Met Val Leu Thr Gly Phe Phe His Asp Met Gly Lys
     130                 135                 140

Val Leu Cys Leu Phe Gly Glu Pro Gln Trp Ala Thr Val Gly Asp Thr
145                 150                 155                 160

Tyr Pro Val Gly Cys Ala Phe Ser Asp Lys Ile Val Phe Ser Glu Phe
                165                 170                 175

Phe Gln Glu Asn Pro Asp Tyr Asn Asn Pro Asn Tyr Asn Thr Lys Tyr
            180                 185                 190

Gly Ile Tyr Glu Pro Asn Cys Gly Leu Ile Asn Val His Ile Ser Trp
        195                 200                 205

Gly His Asp Glu Tyr Phe Tyr Gln Met Met Lys Asn Tyr Leu Pro Glu
    210                 215                 220

Pro Ala Leu Tyr Met Leu Arg Tyr His Ser Phe Tyr Pro Gln His Arg
225                 230                 235                 240

Glu Asn Ala Tyr Lys His
                245

<210> SEQ ID NO 23
<211> LENGTH: 266
<212> TYPE: PRT
<213> ORGANISM: Arabidopsis thaliana

<400> SEQUENCE: 23

Met Thr Ile Ser Val Glu Lys Pro Ile Phe Glu Glu Val Ser Ala
 1               5                  10                  15

Phe Glu Lys Ser Gly Asp Asn Ile Gly Glu Leu Lys Leu Asp Gly Gly
             20                  25                  30

Phe Ser Met Pro Lys Met Asp Thr Asn Asp Glu Ala Phe Leu Ala
         35                  40                  45

Pro Glu Met Asn Ala Phe Gly Arg Gln Phe Arg Asp Tyr Asp Val Glu
 50                  55                  60

Ser Glu Arg Gln Lys Gly Val Glu Glu Phe Tyr Arg Leu Gln His Ile
 65                  70                  75                  80

Asn Gln Thr Val Asp Phe Val Lys Lys Met Arg Ala Glu Tyr Gly Lys
                 85                  90                  95

Leu Asp Lys Met Val Met Ser Ile Trp Glu Cys Cys Glu Leu Leu Asn
             100                 105                 110

Glu Val Val Asp Glu Ser Asp Pro Asp Leu Asp Glu Pro Gln Ile Gln
         115                 120                 125

His Leu Leu Gln Ser Ala Glu Ala Ile Arg Lys Asp Tyr Pro Asn Glu
     130                 135                 140
```

-continued

```
Asp Trp Leu His Leu Thr Ala Leu Ile His Asp Leu Gly Lys Val Ile
145                 150                 155                 160

Thr Leu Pro Gln Phe Gly Leu Pro Gln Trp Ala Val Val Gly Asp
            165                 170                 175

Thr Phe Pro Val Gly Cys Ala Phe Asp Glu Ser Asn Val His His Lys
            180                 185                 190

Tyr Phe Val Glu Asn Pro Asp Phe His Asn Glu Thr Tyr Asn Thr Lys
            195                 200                 205

Asn Gly Ile Tyr Ser Glu Gly Cys Gly Leu Asn Asn Val Met Met Ser
            210                 215                 220

Trp Gly His Asp Asp Tyr Met Tyr Leu Val Ala Lys Glu Asn Gly Ser
225                 230                 235                 240

Thr Leu Pro Ser Ala Gly Gln Phe Ile Ile Arg Tyr His Ser Phe Tyr
            245                 250                 255

Pro Leu His Thr Ala Gly Glu Tyr Thr His
            260                 265
```

<210> SEQ ID NO 24
<211> LENGTH: 190
<212> TYPE: PRT
<213> ORGANISM: Arabidopsis thaliana

<400> SEQUENCE: 24

```
Met Gln His Ile His Gln Thr Tyr Asp Phe Val Lys Lys Met Arg Lys
1               5                   10                  15

Glu Tyr Gly Lys Leu Asn Lys Met Glu Met Ser Ile Trp Glu Cys Cys
            20                  25                  30

Glu Leu Leu Asn Asn Val Val Asp Glu Ser Asp Pro Asp Leu Asp Glu
        35                  40                  45

Pro Gln Ile Gln His Leu Leu Gln Thr Ala Glu Ala Ile Arg Arg Asp
    50                  55                  60

Tyr Pro Asp Glu Asp Trp Leu His Leu Thr Ala Leu Ile His Asp Leu
65                  70                  75                  80

Gly Lys Val Leu Leu Leu Pro Glu Phe Gly Gly Leu Pro Gln Trp Ala
                85                  90                  95

Val Val Gly Asp Thr Phe Pro Val Gly Cys Thr Phe Asp Ser Ala Asn
            100                 105                 110

Ile His His Lys Tyr Phe Lys Gly Asn His Asp Ile Asn Asn Pro Lys
        115                 120                 125

Tyr Asn Thr Lys Asn Gly Val Tyr Thr Glu Gly Cys Gly Leu Asp Asn
    130                 135                 140

Val Leu Met Ser Trp Gly His Asp Asp Tyr Met Tyr Leu Val Ala Lys
145                 150                 155                 160

Lys Asn Gly Thr Thr Leu Pro His Ala Gly Leu Phe Ile Ile Arg Tyr
                165                 170                 175

His Ser Phe Tyr Pro Leu His Lys Ala Gly Ala Tyr Thr His
            180                 185                 190
```

<210> SEQ ID NO 25
<211> LENGTH: 165
<212> TYPE: PRT
<213> ORGANISM: Pinus radiata

<400> SEQUENCE: 25

```
Met Ser Ile Trp Glu Ser Cys Glu Leu Leu Asn Glu Phe Val Asp Glu
1               5                   10                  15
```

```
Ser Asp Pro Asp Leu Asp Glu Pro Gln Ile Glu His Leu Ile Gln Thr
            20                  25                  30

Ala Glu Ala Ile Arg Lys Asp Tyr Pro Asn Glu Glu Trp Leu His Leu
        35                  40                  45

Thr Gly Leu Ile His Asp Leu Gly Lys Val Leu Leu His Pro Asp Phe
    50                  55                  60

Gly Ser Glu Pro Gln Trp Ala Val Val Gly Asp Thr Phe Pro Leu Gly
65                  70                  75                  80

Cys Ala Phe Ser Glu Thr Ile Val His His Glu Phe Phe Lys Asp Asn
                85                  90                  95

Pro Asp Phe His Asn Pro Lys Tyr Asn Thr Lys Tyr Gly Val Tyr Ser
            100                 105                 110

Glu Lys Cys Gly Leu Asp Asn Val Leu Met Ser Trp Gly His Asp Glu
        115                 120                 125

Tyr Met Tyr Leu Val Ala Lys Met Asn Asn Thr Thr Leu Pro Pro Ala
    130                 135                 140

Ala Leu Phe Ile Ile Arg Phe His Ser Phe Tyr Pro Leu His Arg Glu
145                 150                 155                 160

Gly Ala Tyr Met His
                165

<210> SEQ ID NO 26
<211> LENGTH: 233
<212> TYPE: PRT
<213> ORGANISM: Homo sapiens

<400> SEQUENCE: 26

Met Lys Val Thr Val Gly Pro Asp Pro Ser Leu Val Tyr Arg Pro Asp
1               5                   10                  15

Val Asp Pro Glu Val Ala Lys Asp Lys Ala Ser Phe Arg Asn Tyr Thr
            20                  25                  30

Ser Gly Pro Leu Leu Asp Arg Val Phe Thr Thr Tyr Lys Leu Met His
        35                  40                  45

Thr His Gln Thr Val Asp Phe Val Arg Ser Lys His Ala Gln Phe Gly
    50                  55                  60

Gly Phe Ser Tyr Lys Lys Met Thr Val Met Glu Ala Val Asp Leu Leu
65                  70                  75                  80

Asp Gly Leu Val Asp Glu Ser Asp Pro Asp Val Asp Phe Pro Asn Ser
                85                  90                  95

Phe His Ala Phe Gln Thr Ala Glu Gly Ile Arg Lys Ala His Pro Asp
            100                 105                 110

Lys Asp Trp Phe His Leu Val Gly Leu Leu His Asp Leu Gly Lys Val
        115                 120                 125

Leu Ala Leu Phe Gly Glu Pro Gln Trp Ala Val Val Gly Asp Thr Phe
    130                 135                 140

Pro Val Gly Cys Arg Pro Gln Ala Ser Val Val Phe Cys Asp Ser Thr
145                 150                 155                 160

Phe Gln Asp Asn Pro Asp Leu Gln Asp Pro Arg Tyr Ser Thr Glu Leu
                165                 170                 175

Gly Met Tyr Gln Pro His Cys Gly Leu Asp Arg Val Leu Met Ser Trp
            180                 185                 190

Gly His Asp Glu Tyr Met Tyr Gln Val Met Lys Phe Asn Lys Phe Ser
        195                 200                 205

Leu Pro Pro Glu Ala Phe Tyr Met Ile Arg Phe His Ser Phe Tyr Pro
    210                 215                 220
```

```
Trp His Thr Gly Arg Asp Tyr Gln Gln
225                 230

<210> SEQ ID NO 27
<211> LENGTH: 236
<212> TYPE: PRT
<213> ORGANISM: Homo sapiens

<400> SEQUENCE: 27

Met Lys Val Asp Val Gly Pro Asp Pro Ser Leu Val Tyr Arg Pro Asp
 1               5                  10                  15

Val Asp Pro Glu Val Ala Lys Asp Lys Ala Ser Phe Arg Asn Tyr Thr
                20                  25                  30

Ser Gly Pro Leu Leu Asp Arg Val Phe Thr Thr Tyr Lys Leu Met His
            35                  40                  45

Thr His Gln Thr Val Asp Phe Val Arg Ser Lys His Ala Gln Phe Gly
        50                  55                  60

Gly Phe Ser Tyr Lys Lys Met Thr Val Met Glu Ala Val Asp Leu Leu
65                  70                  75                  80

Asp Gly Leu Val Asp Glu Ser Asp Pro Asp Val Asp Phe Pro Asn Ser
                85                  90                  95

Phe His Ala Phe Gln Thr Ala Glu Gly Ile Arg Lys Ala His Pro Asp
            100                 105                 110

Lys Asp Trp Phe His Leu Val Gly Leu Leu His Asp Leu Gly Lys Val
        115                 120                 125

Leu Ala Leu Phe Gly Glu Pro Gln Trp Ala Val Val Gly Asp Thr Phe
130                 135                 140

Pro Val Gly Cys Arg Pro Gln Ala Ser Val Val Phe Cys Asp Ser Thr
145                 150                 155                 160

Phe Gln Asp Asn Pro Asp Leu Gln Asp Pro Arg Tyr Ser Thr Glu Leu
                165                 170                 175

Gly Met Tyr Gln Pro His Cys Gly Leu Asp Arg Val Leu Met Ser Trp
            180                 185                 190

Gly His Asp Glu Tyr Met Tyr Gln Val Met Lys Phe Asn Lys Phe Ser
        195                 200                 205

Leu Pro Pro Glu Ala Phe Tyr Met Ile Arg Phe His Ser Phe Tyr Pro
210                 215                 220

Trp His Thr Gly Arg Asp Tyr Gln Gln Leu Ser Trp
225                 230                 235

<210> SEQ ID NO 28
<211> LENGTH: 195
<212> TYPE: PRT
<213> ORGANISM: Arabidopsis thaliana

<400> SEQUENCE: 28

Met Gln His Ile His Gln Thr Tyr Asp Phe Val Lys Lys Met Arg Lys
 1               5                  10                  15

Glu Tyr Gly Lys Leu Asn Lys Met Glu Met Ser Ile Trp Glu Cys Cys
                20                  25                  30

Glu Leu Leu Asn Asn Val Val Asp Glu Ser Asp Pro Asp Leu Asp Glu
            35                  40                  45

Pro Gln Ile Gln His Leu Leu Gln Thr Ala Glu Ala Ile Arg Arg Asp
        50                  55                  60

Tyr Pro Asp Glu Asp Trp Leu His Leu Thr Ala Leu Ile His Asp Leu
65                  70                  75                  80
```

```
Gly Lys Val Leu Leu Pro Glu Phe Gly Leu Pro Gln Trp Ala
            85              90              95

Val Val Gly Asp Thr Phe Pro Val Gly Cys Thr Phe Asp Ser Ala Asn
            100             105             110

Ile His His Lys Tyr Phe Lys Gly Asn His Asp Ile Asn Asn Pro Lys
            115             120             125

Tyr Asn Thr Lys Asn Gly Val Tyr Thr Glu Gly Cys Gly Leu Asp Asn
        130             135             140

Val Leu Met Ser Trp Gly His Asp Asp Tyr Met Tyr Leu Val Ala Lys
145             150             155             160

Lys Asn Gly Thr Thr Leu Pro His Ala Gly Leu Phe Ile Arg Tyr
            165             170             175

His Ser Phe Tyr Pro Leu His Lys Ala Gly Ala Tyr Thr His Thr Lys
            180             185             190

Met Val Arg
        195

<210> SEQ ID NO 29
<211> LENGTH: 202
<212> TYPE: PRT
<213> ORGANISM: Mus musculus

<400> SEQUENCE: 29

Met Lys Val Asp Val Gly Pro Asp Pro Ser Leu Val Tyr Arg Pro Asp
1               5               10              15

Val Asp Pro Glu Met Ala Lys Ser Lys Asp Ser Phe Arg Asn Tyr Thr
            20              25              30

Ser Gly Pro Leu Leu Asp Arg Val Phe Thr Thr Tyr Lys Leu Met His
            35              40              45

Thr His Gln Thr Val Asp Phe Val Ser Arg Lys Arg Ile Gln Tyr Gly
        50              55              60

Gly Phe Ser Tyr Lys Lys Met Thr Ile Met Glu Ala Val Gly Met Leu
65              70              75              80

Asp Asp Leu Val Asp Glu Ser Asp Pro Asp Val Asp Phe Pro Asn Ser
            85              90              95

Phe His Ala Phe Gln Thr Ala Glu Gly Ile Arg Lys Ala His Pro Asp
            100             105             110

Lys Asp Trp Phe His Leu Val Gly Leu Leu His Asp Leu Gly Lys Ile
            115             120             125

Met Ala Leu Trp Gly Glu Pro Gln Trp Ala Val Val Gly Asp Thr Phe
        130             135             140

Pro Val Gly Cys Arg Pro Gln Ala Ser Val Val Phe Cys Asp Ser Thr
145             150             155             160

Phe Gln Asp Asn Pro Asp Leu Gln Asp Pro Arg Tyr Ser Thr Glu Leu
            165             170             175

Gly Met Tyr Gln Pro His Cys Gly Leu Glu Asn Val Leu Met Ser Trp
            180             185             190

Gly His Asp Glu Tyr Leu Tyr Leu Ser Trp
        195             200

<210> SEQ ID NO 30
<211> LENGTH: 199
<212> TYPE: PRT
<213> ORGANISM: Homo sapiens

<400> SEQUENCE: 30
```

```
Thr Gln Gly Pro Asp Pro Ser Leu Val Tyr Arg Pro Asp Val Asp Pro
  1               5                  10                  15

Glu Val Ala Lys Asp Lys Ala Ser Phe Arg Asn Tyr Thr Ser Gly Pro
             20                  25                  30

Leu Leu Asp Arg Val Phe Thr Thr Tyr Lys Leu Met His Thr His Gln
         35                  40                  45

Thr Val Asp Phe Val Arg Ser Lys His Ala Gln Phe Gly Gly Phe Ser
     50                  55                  60

Tyr Lys Lys Met Thr Val Met Glu Ala Val Asp Leu Leu Asp Gly Leu
 65                  70                  75                  80

Val Asp Glu Ser Asp Pro Asp Val Asp Phe Pro Asn Ser Phe His Ala
             85                  90                  95

Phe Gln Thr Ala Glu Gly Ile Arg Lys Ala His Pro Asp Lys Asp Trp
            100                 105                 110

Phe His Leu Val Gly Leu Leu His Asp Leu Gly Lys Val Leu Ala Leu
         115                 120                 125

Phe Gly Glu Pro Gln Trp Ala Val Val Gly Asp Thr Phe Pro Val Gly
    130                 135                 140

Cys Arg Pro Gln Ala Ser Val Val Phe Cys Asp Ser Thr Phe Gln Asp
145                 150                 155                 160

Asn Pro Asp Leu Gln Asp Pro Arg Tyr Ser Thr Glu Leu Gly Met Tyr
                165                 170                 175

Gln Pro His Cys Gly Leu Asp Arg Val Leu Met Ser Trp Gly His Asp
            180                 185                 190

Glu Tyr Met Tyr Leu Ser Trp
            195

<210> SEQ ID NO 31
<211> LENGTH: 202
<212> TYPE: PRT
<213> ORGANISM: Homo sapiens

<400> SEQUENCE: 31

Met Lys Val Thr Val Gly Pro Asp Pro Ser Leu Val Tyr Arg Pro Asp
  1               5                  10                  15

Val Asp Pro Glu Val Ala Lys Asp Lys Ala Ser Phe Arg Asn Tyr Thr
             20                  25                  30

Ser Gly Pro Leu Leu Asp Arg Val Phe Thr Thr Tyr Lys Leu Met His
         35                  40                  45

Thr His Gln Thr Val Asp Phe Val Arg Ser Lys His Ala Gln Phe Gly
     50                  55                  60

Gly Phe Ser Tyr Lys Lys Met Thr Val Met Glu Ala Val Asp Leu Leu
 65                  70                  75                  80

Asp Gly Leu Val Asp Glu Ser Asp Pro Asp Val Asp Phe Pro Asn Ser
             85                  90                  95

Phe His Ala Phe Gln Thr Ala Glu Gly Ile Arg Lys Ala His Pro Asp
            100                 105                 110

Lys Asp Trp Phe His Leu Val Gly Leu Leu His Asp Leu Gly Lys Val
         115                 120                 125

Leu Ala Leu Phe Gly Glu Pro Gln Trp Ala Val Val Gly Asp Thr Phe
    130                 135                 140

Pro Val Gly Cys Arg Pro Gln Ala Ser Val Val Phe Cys Asp Ser Thr
145                 150                 155                 160

Phe Gln Asp Asn Pro Asp Leu Gln Asp Pro Arg Tyr Ser Thr Glu Leu
```

165                 170                 175
Gly Met Tyr Gln Pro His Cys Gly Leu Asp Arg Val Leu Met Ser Trp
                180                 185                 190

Gly His Asp Glu Tyr Met Phe Leu Ser Trp
        195                 200

<210> SEQ ID NO 32
<211> LENGTH: 201
<212> TYPE: PRT
<213> ORGANISM: Rattus norvegicus

<400> SEQUENCE: 32

Met Lys Val Thr Val Gly Pro Asp Pro Ser Leu Val Tyr Arg Pro Asp
1               5                   10                  15

Val Asp Pro Glu Val Ala Lys Asp Lys Ala Ser Phe Arg Asn Tyr Thr
                20                  25                  30

Ser Gly Pro Leu Leu Asp Arg Val Phe Thr Thr Tyr Lys Leu Met His
            35                  40                  45

Thr His Gln Thr Val Asp Phe Val Arg Ser Lys His Ala Gln Phe Gly
        50                  55                  60

Ser Phe Ser Tyr Lys Lys Met Thr Val Met Glu Ala Val Asp Met Leu
65                  70                  75                  80

Asp Asp Leu Val Asp Glu Ser Asp Pro Asp Val Asp Phe Pro Asn Ser
                85                  90                  95

Phe His Ala Phe Thr Ala Glu Gly Ile Arg Lys Ala His Pro Asp Lys
            100                 105                 110

Asp Trp Phe His Leu Val Gly Leu Leu His Asp Leu Gly Lys Ile Leu
        115                 120                 125

Ala Leu Trp Gly Glu Pro Gln Trp Ala Val Val Gly Asp Thr Phe Pro
    130                 135                 140

Val Gly Cys Arg Pro Gln Ala Ser Val Val Phe Cys Asp Ser Thr Phe
145                 150                 155                 160

Gln Asp Asn Pro Asp Leu Gln Asp Pro Arg Tyr Ser Thr Glu Leu Gly
                165                 170                 175

Met Tyr Gln Pro His Cys Gly Leu Glu Asn Val Leu Met Ser Trp Gly
            180                 185                 190

His Asp Glu Tyr Leu Tyr Leu Ser Trp
        195                 200

<210> SEQ ID NO 33
<211> LENGTH: 202
<212> TYPE: PRT
<213> ORGANISM: Rattus norvegicus

<400> SEQUENCE: 33

Met Lys Val Asp Leu Gly Pro Asp Pro Ser Leu Val Tyr Arg Pro Asp
1               5                   10                  15

Val Asp Pro Glu Met Ala Lys Ser Lys Gly Ser Phe Arg Asn Tyr Thr
                20                  25                  30

Ser Gly Pro Leu Leu Asp Arg Val Phe Thr Thr Tyr Lys Leu Met His
            35                  40                  45

Thr His Gln Thr Val Asp Phe Val Met Arg Lys Arg Ile Gln Phe Gly
        50                  55                  60

Ser Phe Ser Tyr Lys Lys Met Thr Val Met Glu Ala Val Asp Met Leu
65                  70                  75                  80

Asp Asp Leu Val Asp Glu Ser Asp Pro Asp Val Asp Phe Pro Asn Ser

```
                     85                  90                  95
Phe His Ala Phe Gln Thr Ala Glu Gly Ile Arg Lys Ala His Pro Asp
                100                 105                 110
Lys Asp Trp Phe His Leu Val Gly Leu Leu His Asp Leu Gly Lys Ile
                115                 120                 125
Leu Ala Leu Trp Gly Glu Pro Gln Trp Ala Val Val Gly Asp Thr Phe
            130                 135                 140
Pro Val Gly Cys Arg Pro Gln Ala Ser Val Val Phe Cys Asp Ser Thr
145                 150                 155                 160
Phe Gln Asp Asn Pro Asp Leu Gln Asp Pro Arg Tyr Ser Thr Glu Leu
                165                 170                 175
Gly Met Tyr Gln Pro His Cys Gly Leu Glu Asn Val Leu Met Ser Trp
                180                 185                 190
Gly His Asp Glu Tyr Leu Tyr Leu Ser Trp
                195                 200

<210> SEQ ID NO 34
<211> LENGTH: 242
<212> TYPE: PRT
<213> ORGANISM: Arabidopsis thaliana

<400> SEQUENCE: 34

Met Thr Ile Leu Ile Asp Arg His Ser Asp Gln Asn Gly Asp Glu Ile
1               5                   10                  15
Val Glu Lys Asn Gln Gly Asn Gly Lys Glu Glu Thr Glu Leu Val
                20                  25                  30
Leu Asp Ala Gly Phe Glu Ala Pro His Thr Asn Ser Phe Gly Arg Thr
            35                  40                  45
Phe Arg Asp Tyr Asp Ala Glu Ser Glu Arg Arg Gly Val Glu Glu
50                  55                  60
Phe Tyr Arg Val Asn His Ile Gly Gln Thr Val Asp Phe Val Arg Lys
65                  70                  75                  80
Met Arg Glu Glu Tyr Glu Lys Leu Asn Arg Thr Glu Met Ser Ile Trp
                85                  90                  95
Glu Cys Cys Glu Leu Leu Asn Glu Phe Ile Asp Glu Ser Asp Pro Asp
                100                 105                 110
Leu Asp Glu Pro Gln Ile Glu His Leu Leu Gln Thr Ala Glu Ala Ile
            115                 120                 125
Arg Lys Asp Tyr Pro Asp Glu Asp Trp Leu His Leu Thr Gly Leu Ile
130                 135                 140
His Asp Leu Gly Lys Val Leu Leu His Ser Ser Phe Gly Glu Leu Pro
145                 150                 155                 160
Gln Trp Ala Val Val Gly Asp Thr Phe Pro Val Gly Cys Ala Phe Asp
                165                 170                 175
Glu Met Ile Glu Leu Asp Gly Ser Leu Ile Glu Lys Ser Leu Thr
                180                 185                 190
Ile Leu Leu His Gln Lys Glu Thr Pro Trp Tyr Leu Val Asp Trp Leu
            195                 200                 205
Ser Phe Gly Trp Lys Ala Lys Ile Val Glu Met Leu Gly Glu Ala Thr
        210                 215                 220
Gly Ile Leu Ala Ser Val Asp Gly Arg Arg Pro Leu Arg Tyr Gly
225                 230                 235                 240

Leu Arg
```

```
<210> SEQ ID NO 35
<211> LENGTH: 254
<212> TYPE: PRT
<213> ORGANISM: Arabidopsis thaliana

<400> SEQUENCE: 35

Met Gln Val Ser Arg Leu Leu Thr Pro Thr Leu Leu Val Ala Pro Ser
1               5                   10                  15

Gly Arg Tyr Ile His Ile Arg Asp Cys Lys Ile Lys Ser Leu Ile Phe
            20                  25                  30

Ile Tyr Leu Cys Cys Cys His Glu Arg Asp Tyr Asp Ala Glu Ser Glu
        35                  40                  45

Arg Arg Arg Gly Val Glu Glu Phe Tyr Arg Val Asn His Ile Gly Gln
    50                  55                  60

Thr Val Asp Phe Val Arg Lys Met Arg Glu Tyr Glu Lys Leu Asn
65                  70                  75                  80

Arg Thr Glu Met Ser Ile Trp Glu Cys Cys Glu Leu Leu Asn Glu Phe
                85                  90                  95

Ile Asp Glu Ser Asp Pro Asp Leu Asp Glu Pro Gln Ile Glu His Leu
            100                 105                 110

Leu Gln Thr Ala Glu Ala Ile Arg Lys Asp Tyr Pro Asp Glu Asp Trp
        115                 120                 125

Leu His Leu Thr Gly Leu Ile His Asp Leu Gly Lys Val Leu Leu His
    130                 135                 140

Ser Ser Phe Gly Glu Leu Pro Gln Trp Ala Val Val Gly Asp Thr Phe
145                 150                 155                 160

Pro Val Gly Cys Ala Phe Asp Glu Ser Ile Val His His Lys Val His
                165                 170                 175

Lys Tyr Phe Lys Glu Asn Pro Asp Tyr Asp Asn Pro Ser Tyr Asn Ser
            180                 185                 190

Lys Tyr Gly Ile Tyr Thr Glu Gly Cys Gly Leu Asp Asn Val Leu Met
        195                 200                 205

Ser Trp Gly His Asp Asp Tyr Met Tyr Leu Ala Ser Ile Ser Asp Asp
    210                 215                 220

Asp Leu His Asn Gln Leu Trp Ala Ser Gly Gly Trp Thr Glu Lys Thr
225                 230                 235                 240

Thr Ala Leu Trp Ala Ser Leu Ile Ser Asn Trp Ala Phe Ser
                245                 250

<210> SEQ ID NO 36
<211> LENGTH: 325
<212> TYPE: PRT
<213> ORGANISM: Rattus norvegicus

<400> SEQUENCE: 36

Met Thr Ala Ser Ser Val Leu Leu His Thr Gly Gln Lys Met Pro Leu
1               5                   10                  15

Ile Gly Leu Gly Thr Trp Lys Ser Glu Pro Gly Gln Val Lys Ala Ala
            20                  25                  30

Ile Lys Tyr Ala Leu Ser Val Gly Tyr Arg His Ile Asp Cys Ala Ser
        35                  40                  45

Val Tyr Gly Asn Glu Thr Glu Ile Gly Glu Ala Leu Lys Glu Ser Val
    50                  55                  60

Gly Ala Gly Lys Ala Val Pro Arg Glu Glu Leu Phe Val Thr Ser Lys
65                  70                  75                  80

Leu Trp Asn Thr Lys His His Pro Glu Asp Val Glu Pro Ala Val Arg
```

-continued

```
                    85                  90                  95
Lys Thr Leu Ala Asp Leu Gln Leu Glu Tyr Leu Asp Leu Tyr Leu Met
                100                 105                 110

His Trp Pro Tyr Ala Phe Glu Arg Gly Asp Asn Pro Phe Pro Lys Asn
                115                 120                 125

Ala Asp Gly Thr Val Lys Tyr Asp Ser Thr His Tyr Lys Glu Thr Trp
            130                 135                 140

Lys Ala Leu Glu Ala Leu Val Ala Lys Gly Leu Val Lys Ala Leu Gly
145                 150                 155                 160

Leu Ser Asn Phe Ser Ser Arg Gln Ile Asp Asp Val Leu Ser Val Ala
                165                 170                 175

Ser Val Arg Pro Ala Val Leu Gln Val Glu Cys His Pro Tyr Leu Ala
                180                 185                 190

Gln Asn Glu Leu Ile Ala His Cys Gln Ala Arg Gly Leu Glu Val Thr
            195                 200                 205

Ala Tyr Ser Pro Leu Gly Ser Ser Asp Arg Ala Trp Arg His Pro Asp
        210                 215                 220

Glu Pro Val Leu Leu Glu Pro Val Val Leu Ala Leu Ala Glu Lys
225                 230                 235                 240

His Gly Arg Ser Pro Ala Gln Ile Leu Leu Arg Trp Gln Val Gln Arg
                245                 250                 255

Lys Val Ile Cys Ile Pro Lys Ser Ile Thr Pro Ser Arg Ile Leu Gln
                260                 265                 270

Asn Ile Gln Val Phe Asp Phe Thr Phe Ser Pro Glu Glu Met Lys Gln
            275                 280                 285

Leu Asp Ala Leu Asn Lys Asn Trp Arg Tyr Ile Val Pro Met Ile Thr
        290                 295                 300

Val Asp Gly Lys Arg Val Pro Arg Asp Ala Gly His Pro Leu Tyr Pro
305                 310                 315                 320

Phe Asn Asp Pro Tyr
                325

<210> SEQ ID NO 37
<211> LENGTH: 320
<212> TYPE: PRT
<213> ORGANISM: Zymomonas mobilis

<400> SEQUENCE: 37

Met Thr Thr Gly Arg Met Ser Arg Arg Glu Cys Leu Ser Ala Ala Val
1               5                   10                  15

Met Val Pro Ile Ala Ala Met Thr Ala Thr Ala Thr Ile Thr Gly Ser
                20                  25                  30

Ala Glu Ala Ala Lys Asn Asn Met Asn Gly Ser Thr Ile Gly Lys Ile
            35                  40                  45

Thr Lys Phe Ser Pro Arg Leu Asp Ala Ile Leu Asp Val Ser Thr Pro
        50                  55                  60

Ile Glu Val Ile Ala Ser Asp Ile Gln Trp Ser Glu Gly Pro Val Trp
65                  70                  75                  80

Val Lys Asn Gly Asn Phe Leu Leu Phe Ser Asp Pro Ala Asn Ile
                85                  90                  95

Met Arg Lys Trp Thr Pro Asp Ala Gly Val Ser Ile Phe Leu Lys Pro
                100                 105                 110

Ser Gly His Ala Glu Pro Ile Pro Ala Gly Gln Phe Arg Glu Pro Gly
            115                 120                 125
```

```
Ser Asn Gly Met Lys Val Gly Pro Asp Gly Lys Ile Trp Val Ala Asp
130                 135                 140

Ser Gly Thr Arg Ala Ile Met Lys Val Asp Pro Val Thr Arg Gln Arg
145                 150                 155                 160

Ser Val Val Asp Asn Tyr Lys Gly Lys Arg Phe Asn Ser Pro Asn Asp
                165                 170                 175

Leu Phe Phe Ser Lys Ser Gly Ala Val Tyr Phe Thr Asp Pro Pro Tyr
            180                 185                 190

Gly Leu Thr Asn Leu Asp Glu Ser Asp Ile Lys Glu Met Asn Tyr Asn
        195                 200                 205

Gly Val Phe Arg Leu Ser Pro Asp Gly Arg Leu Asp Leu Ile Glu Ala
    210                 215                 220

Gly Leu Ser Arg Pro Asn Gly Leu Ala Leu Ser Pro Asp Glu Thr Lys
225                 230                 235                 240

Leu Tyr Val Ser Asn Ser Asp Arg Ala Ser Pro Asn Ile Trp Val Tyr
                245                 250                 255

Ser Leu Asp Ser Asn Gly Leu Pro Thr Ser Arg Thr Leu Leu Arg Asn
            260                 265                 270

Phe Arg Lys Glu Tyr Phe Asp Gln Gly Leu Ala Gly Leu Pro Asp Gly
        275                 280                 285

Met Asn Ile Asp Lys Gln Gly Asn Leu Phe Ala Ser Ala Pro Gly Gly
    290                 295                 300

Ile Tyr Ile Phe Ala Pro Asp Gly Glu Cys Leu Gly Leu Ile Phe Trp
305                 310                 315                 320

<210> SEQ ID NO 38
<211> LENGTH: 400
<212> TYPE: PRT
<213> ORGANISM: Fusarium oxysporum

<400> SEQUENCE: 38

Met Pro Ser Ser Ile Ser Val Leu Ala Gly Val Leu Pro Val Leu
1               5                   10                  15

Gly Ala Val Ala Ala Lys Leu Pro Ser Thr Ala Gln Ile Ile Asp Gln
                20                  25                  30

Lys Ser Phe Asn Val Leu Lys Asp Val Pro Pro Ala Val Ala Asn
            35                  40                  45

Asp Ser Leu Val Phe Thr Trp Pro Gly Val Thr Glu Glu Ser Leu Val
        50                  55                  60

Glu Lys Pro Phe His Val Tyr Asp Glu Phe Tyr Asp Val Ile Gly
65                  70                  75                  80

Lys Asp Pro Ser Leu Thr Leu Ile Ala Thr Ser Asp Thr Asp Pro Ile
                85                  90                  95

Phe His Glu Ala Val Val Trp Tyr Pro Pro Thr Glu Glu Val Phe Phe
            100                 105                 110

Val Gln Asn Ala Gly Ala Pro Ala Gly Thr Gly Leu Asn Lys Ser
        115                 120                 125

Ser Ile Ile Gln Lys Ile Ser Leu Lys Glu Ala Asp Ala Val Arg Lys
130                 135                 140

Gly Lys Gln Asp Glu Val Lys Val Thr Val Val Asp Ser Asn Pro Gln
145                 150                 155                 160

Val Ile Asn Pro Asn Gly Gly Thr Tyr Tyr Lys Gly Asn Ile Ile Phe
                165                 170                 175

Ala Gly Glu Gly Gln Gly Asp Asp Val Pro Ser Ala Leu Tyr Leu Met
            180                 185                 190
```

```
Asn Pro Leu Pro Pro Tyr Asn Thr Thr Thr Leu Leu Asn Asn Tyr Phe
        195                 200                 205

Gly Arg Gln Phe Asn Ser Leu Asn Asp Val Gly Ile Asn Pro Arg Asn
        210                 215                 220

Gly Asp Leu Tyr Phe Thr Asp Thr Leu Tyr Gly Tyr Leu Gln Asp Phe
225                 230                 235                 240

Arg Pro Val Pro Gly Leu Arg Asn Gln Val Tyr Arg Tyr Asn Phe Asp
                245                 250                 255

Thr Gly Ala Val Thr Val Ala Asp Asp Phe Thr Leu Pro Asn Gly
        260                 265                 270

Ile Gly Phe Gly Pro Asp Gly Lys Lys Val Tyr Val Thr Asp Thr Gly
        275                 280                 285

Ile Ala Leu Gly Phe Tyr Gly Arg Asn Leu Ser Ser Pro Ala Ser Val
        290                 295                 300

Tyr Ser Phe Asp Val Asn Gln Asp Gly Thr Leu Gln Asn Arg Lys Thr
305                 310                 315                 320

Phe Ala Tyr Val Ala Ser Phe Ile Pro Asp Gly Val His Thr Asp Ser
                325                 330                 335

Lys Gly Arg Val Tyr Ala Gly Cys Gly Asp Gly Val His Val Trp Asn
                340                 345                 350

Pro Ser Gly Lys Leu Ile Gly Lys Ile Tyr Thr Gly Thr Val Ala Ala
                355                 360                 365

Asn Phe Gln Phe Ala Gly Lys Gly Arg Met Ile Ile Thr Gly Gln Thr
        370                 375                 380

Lys Leu Phe Tyr Val Thr Leu Gly Ala Ser Gly Pro Lys Leu Tyr Asp
385                 390                 395                 400
```

<210> SEQ ID NO 39
<211> LENGTH: 440
<212> TYPE: PRT
<213> ORGANISM: Rattus norvegicus

<400> SEQUENCE: 39

```
Met Val His Gly Tyr Lys Gly Val Gln Phe Gln Asn Trp Ala Lys Thr
1               5                   10                  15

Tyr Gly Cys Ser Pro Glu Val Tyr Tyr Gln Pro Thr Ser Val Glu Glu
                20                  25                  30

Val Arg Glu Val Leu Ala Leu Ala Arg Glu Gln Lys Lys Lys Val Lys
        35                  40                  45

Val Val Gly Gly Gly His Ser Pro Ser Asp Ile Ala Cys Thr Asp Gly
    50                  55                  60

Phe Met Ile His Met Gly Lys Met Asn Arg Val Leu Gln Val Asp Lys
65                  70                  75                  80

Glu Lys Lys Gln Ile Thr Val Glu Ala Gly Ile Leu Leu Ala Asp Leu
                85                  90                  95

His Pro Gln Leu Asp Glu His Gly Leu Ala Met Ser Asn Leu Gly Ala
            100                 105                 110

Val Ser Asp Val Thr Val Ala Gly Val Ile Gly Ser Gly Thr His Asn
        115                 120                 125

Thr Gly Ile Lys His Gly Ile Leu Ala Thr Gln Val Val Ala Leu Thr
    130                 135                 140

Leu Met Thr Ala Asp Gly Glu Val Leu Glu Cys Ser Glu Ser Arg Asn
145                 150                 155                 160

Ala Asp Val Phe Gln Ala Ala Arg Val His Leu Gly Cys Leu Gly Ile
```

```
                    165                 170                 175
Ile Leu Thr Val Thr Leu Gln Cys Val Pro Gln Phe Gln Leu Gln Glu
                180                 185                 190

Thr Ser Phe Pro Ser Thr Leu Lys Glu Val Leu Asp Asn Leu Asp Ser
            195                 200                 205

His Leu Lys Arg Ser Glu Tyr Phe Arg Phe Leu Trp Phe Pro His Thr
        210                 215                 220

Glu Asn Val Ser Ile Ile Tyr Gln Asp His Thr Asn Lys Ala Pro Ser
225                 230                 235                 240

Ser Ala Ser Asn Trp Phe Trp Asp Tyr Ala Ile Gly Phe Tyr Leu Leu
                245                 250                 255

Glu Phe Leu Leu Trp Thr Ser Thr Tyr Leu Pro Cys Leu Val Gly Trp
            260                 265                 270

Ile Asn Arg Phe Phe Phe Trp Met Leu Phe Asn Cys Lys Lys Glu Ser
        275                 280                 285

Ser Asn Leu Ser His Lys Ile Phe Thr Tyr Glu Cys Arg Phe Lys Gln
290                 295                 300

His Val Gln Asp Trp Ala Ile Pro Arg Glu Lys Thr Lys Glu Ala Leu
305                 310                 315                 320

Leu Glu Leu Lys Ala Met Leu Glu Ala His Pro Lys Val Val Ala His
                325                 330                 335

Tyr Pro Val Glu Val Arg Phe Thr Arg Gly Asp Asp Ile Leu Leu Ser
            340                 345                 350

Pro Cys Phe Gln Arg Asp Ser Cys Tyr Met Asn Ile Ile Met Tyr Arg
        355                 360                 365

Pro Tyr Gly Lys Asp Val Pro Arg Leu Asp Tyr Trp Leu Ala Tyr Glu
        370                 375                 380

Thr Ile Met Lys Lys Phe Gly Gly Arg Pro His Trp Ala Lys Ala His
385                 390                 395                 400

Asn Cys Thr Gln Lys Asp Phe Glu Glu Met Tyr Pro Thr Phe His Lys
                405                 410                 415

Phe Cys Asp Ile Arg Glu Lys Leu Asp Pro Thr Gly Met Phe Leu Asn
            420                 425                 430

Ser Tyr Leu Glu Lys Val Phe Tyr
        435                 440

<210> SEQ ID NO 40
<211> LENGTH: 526
<212> TYPE: PRT
<213> ORGANISM: Saccharomyces cerevisiae

<400> SEQUENCE: 40

Met Ser Thr Ile Pro Phe Arg Lys Asn Tyr Val Phe Lys Asn Trp Ala
1               5                   10                  15

Gly Ile Tyr Ser Ala Lys Pro Glu Arg Tyr Phe Gln Pro Ser Ser Ile
                20                  25                  30

Asp Glu Val Val Glu Leu Val Lys Ser Ala Arg Leu Ala Glu Lys Ser
            35                  40                  45

Leu Val Thr Val Gly Ser Gly His Ser Pro Ser Asn Met Cys Val Thr
        50                  55                  60

Asp Glu Trp Leu Val Asn Leu Asp Arg Leu Lys Val Gln Lys Phe
65                  70                  75                  80

Val Glu Tyr Pro Glu Leu His Tyr Ala Asp Val Thr Val Asp Ala Gly
                85                  90                  95
```

-continued

```
Met Arg Leu Tyr Gln Leu Asn Glu Phe Leu Gly Ala Lys Gly Tyr Ser
            100                 105                 110
Ile Gln Asn Leu Gly Ser Ile Ser Glu Gln Ser Val Ala Gly Ile Ile
            115                 120                 125
Ser Thr Gly Ser His Gly Ser Ser Pro Tyr His Gly Leu Ile Ser Ser
    130                 135                 140
Gln Tyr Val Asn Leu Thr Ile Val Asn Gly Lys Gly Glu Leu Lys Phe
145                 150                 155                 160
Leu Asp Ala Glu Asn Asp Pro Glu Val Phe Lys Ala Leu Leu Ser
                165                 170                 175
Val Gly Lys Ile Gly Ile Ile Val Ser Ala Thr Ile Arg Val Val Pro
                180                 185                 190
Gly Phe Asn Ile Lys Ser Thr Gln Glu Val Ile Thr Phe Glu Asn Leu
            195                 200                 205
Leu Lys Gln Trp Asp Thr Leu Trp Thr Ser Ser Glu Phe Ile Arg Val
    210                 215                 220
Trp Trp Tyr Pro Tyr Thr Arg Lys Cys Val Leu Trp Arg Gly Asn Lys
225                 230                 235                 240
Thr Thr Asp Ala Gln Asn Gly Pro Ala Lys Ser Trp Trp Gly Thr Lys
                245                 250                 255
Leu Gly Arg Phe Phe Tyr Glu Thr Leu Leu Trp Ile Ser Thr Lys Ile
            260                 265                 270
Tyr Ala Pro Leu Thr Pro Phe Val Glu Lys Phe Val Phe Asn Arg Gln
    275                 280                 285
Tyr Gly Lys Leu Glu Lys Ser Ser Thr Gly Asp Val Asn Val Thr Asp
290                 295                 300
Ser Ile Ser Gly Phe Asn Met Asp Cys Leu Phe Ser Gln Phe Val Asp
305                 310                 315                 320
Glu Trp Gly Cys Pro Met Asp Asn Gly Leu Glu Val Leu Arg Ser Leu
                325                 330                 335
Asp His Ser Ile Ala Gln Ala Ala Ile Asn Lys Glu Phe Tyr Val His
            340                 345                 350
Val Pro Met Glu Val Arg Cys Ser Asn Thr Thr Leu Pro Ser Glu Pro
    355                 360                 365
Leu Asp Thr Ser Lys Arg Thr Asn Thr Ser Pro Gly Pro Val Tyr Gly
370                 375                 380
Asn Val Cys Arg Pro Phe Leu Asp Asn Thr Pro Ser His Cys Arg Phe
385                 390                 395                 400
Ala Pro Leu Glu Asn Val Thr Asn Ser Gln Leu Thr Leu Tyr Ile Asn
                405                 410                 415
Pro Thr Ile Tyr Arg Pro Phe Gly Cys Asn Thr Pro Ile His Lys Trp
            420                 425                 430
Phe Thr Leu Phe Glu Asn Thr Met Met Val Ala Gly Lys Pro His
    435                 440                 445
Trp Ala Lys Asn Phe Leu Gly Ser Thr Thr Leu Ala Ala Gly Pro Val
    450                 455                 460
Lys Lys Asp Thr Asp Tyr Asp Asp Phe Glu Met Arg Gly Met Ala Leu
465                 470                 475                 480
Lys Val Glu Glu Trp Tyr Gly Glu Asp Leu Lys Lys Phe Arg Lys Ile
                485                 490                 495
Arg Lys Glu Gln Asp Pro Asp Asn Val Phe Leu Ala Asn Lys Gln Trp
                500                 505                 510
Ala Ile Ile Asn Gly Ile Ile Asp Pro Ser Glu Leu Ser Asp
```

<210> SEQ ID NO 41
<211> LENGTH: 432
<212> TYPE: PRT
<213> ORGANISM: Escherichia coli

<400> SEQUENCE: 41

```
Met Lys Ala Ile Leu Ile Pro Phe Leu Ser Leu Leu Ile Pro Leu Thr
 1               5                  10                  15
Pro Gln Ser Ala Phe Ala Gln Ser Glu Pro Glu Leu Lys Leu Glu Ser
            20                  25                  30
Val Val Ile Val Ser Arg His Gly Val Arg Ala Pro Thr Lys Ala Thr
        35                  40                  45
Gln Leu Met Gln Asp Val Thr Pro Asp Ala Trp Pro Thr Trp Pro Val
    50                  55                  60
Lys Leu Gly Trp Leu Thr Pro Arg Gly Gly Glu Leu Ile Ala Tyr Leu
65                  70                  75                  80
Gly His Tyr Gln Arg Gln Arg Leu Val Ala Asp Gly Leu Leu Ala Lys
                85                  90                  95
Lys Gly Cys Pro Gln Ser Gly Gln Val Ala Ile Ile Ala Asp Val Asp
            100                 105                 110
Glu Arg Thr Arg Lys Thr Gly Glu Ala Phe Ala Ala Gly Leu Ala Pro
        115                 120                 125
Asp Cys Ala Ile Thr Val His Thr Gln Ala Asp Thr Ser Ser Pro Asp
    130                 135                 140
Pro Leu Phe Asn Pro Leu Lys Thr Gly Val Cys Gln Leu Asp Asn Ala
145                 150                 155                 160
Asn Val Thr Asp Ala Ile Leu Ser Arg Ala Gly Gly Ser Ile Ala Asp
                165                 170                 175
Phe Thr Gly His Arg Gln Thr Ala Phe Arg Glu Leu Glu Arg Val Leu
            180                 185                 190
Asn Phe Pro Gln Ser Asn Leu Cys Leu Lys Arg Glu Lys Gln Asp Glu
        195                 200                 205
Ser Cys Ser Leu Thr Gln Ala Leu Pro Ser Glu Leu Lys Val Ser Ala
    210                 215                 220
Asp Asn Val Ser Leu Thr Gly Ala Val Ser Leu Ala Ser Met Leu Thr
225                 230                 235                 240
Glu Ile Phe Leu Leu Gln Gln Ala Gln Gly Met Pro Glu Pro Gly Trp
                245                 250                 255
Gly Arg Ile Thr Asp Ser His Gln Trp Asn Thr Leu Leu Ser Leu His
            260                 265                 270
Asn Ala Gln Phe Tyr Leu Leu Gln Arg Thr Pro Glu Val Ala Arg Ser
        275                 280                 285
Arg Ala Thr Pro Leu Leu Asp Leu Ile Lys Thr Ala Leu Thr Pro His
    290                 295                 300
Pro Pro Gln Lys Gln Ala Tyr Gly Val Thr Leu Pro Thr Ser Val Leu
305                 310                 315                 320
Phe Ile Ala Gly His Asp Thr Asn Leu Ala Asn Leu Gly Gly Ala Leu
                325                 330                 335
Glu Leu Asn Trp Thr Leu Pro Gly Gln Pro Asp Asn Thr Pro Pro Gly
            340                 345                 350
Gly Glu Leu Val Phe Glu Arg Trp Arg Arg Leu Ser Asp Asn Ser Gln
        355                 360                 365
```

```
Trp Ile Gln Val Ser Leu Val Phe Gln Thr Leu Gln Met Arg Asp
    370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
                420                 425                 430

<210> SEQ ID NO 42
<211> LENGTH: 354
<212> TYPE: PRT
<213> ORGANISM: Bacillus subtilis

<400> SEQUENCE: 42

Leu Ser Asp Pro Tyr His Phe Thr Val Asn Ala Ala Glu Thr Glu
  1               5                  10                  15

Pro Val Asp Thr Ala Gly Asp Ala Ala Asp Pro Ala Ile Trp Leu
                 20                  25                  30

Asp Pro Lys Asn Pro Gln Asn Ser Lys Leu Ile Thr Thr Asn Lys Lys
                 35                  40                  45

Ser Gly Leu Val Val Tyr Ser Leu Glu Gly Lys Thr Leu His Ser Tyr
 50                  55                  60

His Thr Gly Lys Leu Asn Asn Val Asp Ile Arg Tyr Asp Phe Pro Leu
 65                  70                  75                  80

Asn Gly Lys Lys Val Asp Ile Ala Ala Ser Asn Arg Ser Glu Gly
                 85                  90                  95

Lys Asn Thr Ile Glu Ile Tyr Ala Ile Asp Gly Lys Asn Gly Thr Leu
                100                 105                 110

Gln Ser Ile Thr Asp Pro Asp Arg Pro Ile Ala Ser Ala Ile Asp Glu
            115                 120                 125

Val Tyr Gly Phe Ser Leu Tyr His Ser Gln Lys Thr Gly Arg Tyr Tyr
        130                 135                 140

Ala Met Val Thr Gly Lys Glu Gly Glu Phe Glu Gln Tyr Glu Leu Asn
145                 150                 155                 160

Ala Asp Lys Asn Gly Tyr Ile Ser Gly Lys Lys Val Arg Ala Phe Lys
                165                 170                 175

Met Asn Ser Gln Thr Glu Gly Met Ala Ala Asp Asp Glu Tyr Gly Ser
                180                 185                 190

Leu Tyr Ile Ala Glu Glu Asp Glu Ala Ile Trp Lys Phe Ser Ala Glu
            195                 200                 205

Pro Asp Gly Gly Ser Asn Gly Thr Val Ile Asp Arg Ala Asp Gly Arg
        210                 215                 220

His Leu Thr Pro Asp Ile Glu Gly Leu Thr Ile Tyr Tyr Ala Ala Asp
225                 230                 235                 240

Gly Lys Gly Tyr Leu Leu Ala Ser Ser Gln Gly Asn Ser Ser Tyr Ala
                245                 250                 255

Ile Tyr Glu Arg Gln Gly Gln Asn Lys Tyr Val Ala Asp Phe Gln Ile
            260                 265                 270

Thr Asp Gly Pro Glu Thr Asp Gly Thr Ser Asp Thr Asp Gly Ile Asp
        275                 280                 285

Val Leu Gly Phe Gly Leu Gly Pro Glu Tyr Pro Phe Gly Leu Phe Val
        290                 295                 300

Ala Gln Asp Gly Glu Asn Ile Asp His Gly Gln Lys Val Asn Gln Asn
305                 310                 315                 320
```

```
Phe Lys Met Val Pro Trp Glu Arg Ile Ala Asp Lys Ile Gly Phe His
            325                 330                 335

Pro Gln Val Asn Lys Gln Val Asp Pro Arg Glu Leu Thr Asp Arg Ser
            340                 345                 350

Gly Lys

<210> SEQ ID NO 43
<211> LENGTH: 461
<212> TYPE: PRT
<213> ORGANISM: Schwanniomyces occidentalis

<400> SEQUENCE: 43

Met Val Ser Ile Ser Lys Leu Ile Asn Asn Gly Leu Leu Ala Gly
  1               5                  10                  15

Gln Ser Val Tyr Gln Asp Leu Ala Thr Pro Gln Gln Ser Ser Val Glu
             20                  25                  30

Gln Tyr Asn Ile Ile Arg Phe Leu Gly Gly Ser Gly Pro Tyr Ile Gln
         35                  40                  45

Arg Ser Gly Tyr Gly Ile Ser Thr Asp Ile Pro Asp Gln Cys Thr Ile
 50                  55                  60

Lys Gln Val Gln Leu Met Ser Arg His Gly Glu Arg Tyr Pro Ser Lys
 65                  70                  75                  80

Asn Ser Gly Lys Lys Leu Lys Thr Ile Tyr Gly Lys Leu Lys Ser Tyr
                 85                  90                  95

Asn Gly Thr Phe Thr Gly Ser Leu Ala Phe Leu Asn Asp Tyr Glu Tyr
            100                 105                 110

Phe Val Pro Asp Asp Ser Leu Tyr Glu Lys Glu Thr Ser Ala Leu Asn
            115                 120                 125

Ser Gln Gly Leu Phe Ala Gly Thr Thr Asp Ala Leu Arg His Gly Ala
        130                 135                 140

Ala Phe Arg Ala Lys Tyr Gly Ser Leu Tyr Lys Gln Asn Ser Thr Leu
145                 150                 155                 160

Pro Val Phe Thr Ser Asn Ser Asn Arg Val Tyr Gln Thr Ser Glu Tyr
                165                 170                 175

Phe Ala Arg Gly Phe Leu Gly Asp Glu Phe Ser Asp Ala Thr Val His
            180                 185                 190

Phe Ala Ile Ile Asp Glu Asp Pro Lys Met Gly Val Asn Ser Leu Thr
        195                 200                 205

Pro Arg Ala Ala Cys Asp Asn Tyr Asn Glu Asp Val Asn Asp Gly Ile
    210                 215                 220

Val Asn Gln Tyr Ser Thr Asp Tyr Leu Asp Glu Ala Leu Lys Arg Phe
225                 230                 235                 240

Gln Ser Ser Asn Pro Gly Leu Asn Leu Thr Ser Glu Asp Val Tyr Gln
                245                 250                 255

Leu Phe Ala Tyr Cys Ala Tyr Glu Thr Asn Val Lys Gly Ala Ser Pro
            260                 265                 270

Phe Cys Asp Leu Phe Thr Asn Glu Glu Tyr Ile Gln Tyr Ser Tyr Ser
        275                 280                 285

Val Asp Leu Ser Asn Tyr Tyr Ser His Gly Ala Gly His Asn Leu Thr
    290                 295                 300

Lys Thr Ile Gly Ser Thr Leu Leu Asn Ala Ser Leu Thr Leu Leu Lys
305                 310                 315                 320

Asp Gly Thr Asn Asp Asn Lys Ile Trp Leu Ser Phe Ser His Asp Thr
                325                 330                 335
```

-continued

```
Asp Leu Glu Ile Phe His Ser Ala Leu Gly Ile Val Glu Pro Ala Glu
            340                 345                 350

Asp Leu Pro Val Asp Tyr Ile Pro Phe Pro Ser Pro Tyr Ile His Ser
            355                 360                 365

Gln Ile Val Pro Gln Gly Ala Arg Ile Tyr Thr Glu Lys Tyr Ser Cys
            370                 375                 380

Gly Asn Glu Thr Tyr Val Arg Tyr Ile Leu Asn Asp Ala Val Val Pro
385                 390                 395                 400

Ile Pro Lys Cys Ser Ser Gly Pro Gly Phe Ser Cys Glu Leu Ser Lys
                405                 410                 415

Phe Glu Glu Tyr Ile Asn Lys Arg Leu Arg Asp Val Asp Phe Val Glu
            420                 425                 430

Gln Cys Asp Leu Lys Asp Ala Pro Thr Glu Val Thr Phe Tyr Trp Asp
            435                 440                 445

Tyr Thr Ser Val Asn Tyr Ser Ala Ser Leu Ile Asn Gly
            450                 455                 460

<210> SEQ ID NO 44
<211> LENGTH: 531
<212> TYPE: PRT
<213> ORGANISM: Schizosaccharomyces pombe

<400> SEQUENCE: 44

Met Ala Ser Glu Arg Asp Pro Leu Leu Pro Val His Gly Glu Gly Pro
1               5                   10                  15

Glu Ser Pro Ser Arg Arg Asn Trp Lys Thr Trp Ile Lys His Gly Ile
            20                  25                  30

Leu Leu Ile Leu Val Leu Ser Thr Val Ile Phe Phe Tyr Phe Phe Ser
            35                  40                  45

Ser His Lys Ser Lys Gly Thr Asn Glu Lys Pro Lys Phe Val Ile Met
        50                  55                  60

Met Val Ser Asp Gly Met Gly Pro Gly Ser Leu Ser Met Thr Arg Ser
65              70                  75                  80

Phe Val Glu Thr Leu Asn Asp Lys Glu Gly Tyr Arg Leu Pro Leu Asp
            85                  90                  95

Glu His Leu Ile Gly Ser Ser Arg Thr Arg Ser Ser Ser Leu Ile
            100                 105                 110

Thr Asp Ser Ala Ala Gly Ala Thr Ala Phe Ser Cys Ala Asn Lys Thr
            115                 120                 125

Tyr Asn Gly Ala Val Gly Val Leu Asp Asn Glu Lys Pro Cys Gly Thr
        130                 135                 140

Ile Leu Glu Ala Ala Lys Glu Ala Gly Tyr Leu Thr Gly Ile Val Val
145                 150                 155                 160

Thr Ser Arg Val Thr Asp Ala Thr Pro Ala Ser Phe Ser Ala His Ala
                165                 170                 175

Ala Asn Arg Phe Met Gln Asp Leu Ile Ala Glu Tyr Gln Val Gly Met
            180                 185                 190

Gly Pro Leu Gly Arg Ser Val Asp Leu Leu Phe Gly Gly Gly Leu Cys
            195                 200                 205

Ser Phe Leu Pro Lys Ser Thr Tyr Arg Ser Cys Arg Ser Asp Asn Leu
        210                 215                 220

Asp Leu Leu Lys Tyr Ala Arg Lys Lys Glu Gly Phe Gln Ile Leu Leu
225                 230                 235                 240

Asn Arg Thr Asp Phe Asp Glu Leu Ser Asn Ala Gln Leu Pro Leu Leu
```

```
                245                 250                 255
Gly Leu Phe Ser Asp Tyr His Leu Ser Tyr Asp Ile Asp Tyr Gln Pro
                260                 265                 270
Glu Val Gln Pro Lys Leu Ser Glu Met Val Glu Thr Ala Leu Asp Val
            275                 280                 285
Leu Leu Asn Ala Thr Asn Glu Asp Thr Ser Lys Gly Phe Phe Leu Leu
        290                 295                 300
Ile Glu Gly Ser Arg Ile Asp Met Ala Ser His Asn Asn Asp Pro Ile
305                 310                 315                 320
Ala His Val Tyr Glu Val Met Glu Tyr Asn Arg Ala Phe Glu Ile Ala
                325                 330                 335
Ser Ala Phe Val Glu Lys Asn Gly Gly Ser Leu Ile Ser Thr Ser Asp
                340                 345                 350
His Glu Thr Gly Gly Leu Thr Val Gly Arg Gln Val Ser Lys Lys Tyr
            355                 360                 365
Pro Glu Tyr Leu Trp Lys Pro Gln Val Leu Ser Leu Ala Leu His Ser
        370                 375                 380
Ile Glu Tyr Leu Ala Ser Ala Val Asn His Asn Gln Asn Thr Leu Leu
385                 390                 395                 400
Pro Tyr Ile Glu Gln Phe Val Leu Pro Ala Ile Gly Ile Pro Asp Pro
                405                 410                 415
Asn Pro Lys Gln Ile His Asp Ile Tyr Val Ala Arg His Asn Ile Phe
                420                 425                 430
Asn Leu Ile Asn Val Leu Ser Asp Ile Val Ser Val Glu Ala Gln Ile
            435                 440                 445
Gly Trp Thr Thr His Gly His Thr Ala Val Asp Val Asn Val Tyr Gly
        450                 455                 460
Val Gly Glu Val Thr Glu His Leu Arg Gly Asn Met Glu Asn Ile Glu
465                 470                 475                 480
Ile Gly Gln Phe Met Glu Ile Tyr Leu Asn Val Ser Leu Ser Asp Val
                485                 490                 495
Thr Glu Lys Leu Lys Asp Ala Pro Ile His Gly Ala Pro Asp Arg His
            500                 505                 510
Cys Leu Val Glu Thr Ser Phe Ser Asp Arg Leu Val Gly Phe Gly Ala
        515                 520                 525
Asp Leu Phe
    530

<210> SEQ ID NO 45
<211> LENGTH: 34
<212> TYPE: DNA
<213> ORGANISM: Artificial Sequence
<220> FEATURE:
<223> OTHER INFORMATION: primer

<400> SEQUENCE: 45
attatgtaca atgaaggtga cggtgggccc agac                              34

<210> SEQ ID NO 46
<211> LENGTH: 28
<212> TYPE: DNA
<213> ORGANISM: Artificial Sequence
<220> FEATURE:
<223> OTHER INFORMATION: primer

<400> SEQUENCE: 46
ctatggtacc tcaccagctc aggatgcc                                    28
```

<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47
cgcggatcca tggctaagct tccttctacg                                    30

<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48
cgactcgagc taatcataga gcttgggacc                                    30

<210> SEQ ID NO 49
<211> LENGTH: 43
<212> TYPE: DNA
<213> ORGANISM: Artificial Sequence
<220> FEATURE:
<223> OTHER INFORMATION: primer

<400> SEQUENCE: 49
ggcggctagc gaaggagata taccatggtc catgggtaca aag                     43

<210> SEQ ID NO 50
<211> LENGTH: 49
<212> TYPE: DNA
<213> ORGANISM: Artificial Sequence
<220> FEATURE:
<223> OTHER INFORMATION: primer

<400> SEQUENCE: 50
cttcgggagc gtgcatggta tatctccttc tgcatgctcg agttagtag               49

<210> SEQ ID NO 51
<211> LENGTH: 51
<212> TYPE: DNA
<213> ORGANISM: Artificial Sequence
<220> FEATURE:
<223> OTHER INFORMATION: primer

<400> SEQUENCE: 51
ctactaactc gagcatgcag aaggagatat accatgcacg ctcccgaagt c            51

<210> SEQ ID NO 52
<211> LENGTH: 58
<212> TYPE: DNA
<213> ORGANISM: Artificial Sequence
<220> FEATURE:
<223> OTHER INFORMATION: primer

<400> SEQUENCE: 52
gaggccgcca tggtatatct ccttcacgcg tggcgcgcct accactgcac ctcctcag     58

<210> SEQ ID NO 53
<211> LENGTH: 52
<212> TYPE: DNA
<213> ORGANISM: Artificial Sequence
<220> FEATURE:

<223> OTHER INFORMATION: primer

<400> SEQUENCE: 53
ggtaggcgcg ccacgcgtga aggagatata ccatggcggc ctccagtgtc ct     52

<210> SEQ ID NO 54
<211> LENGTH: 33
<212> TYPE: DNA
<213> ORGANISM: Artificial Sequence
<220> FEATURE:
<223> OTHER INFORMATION: primer

<400> SEQUENCE: 54
cggcttaatt aatgcggccc tctagatcag tat     33

<210> SEQ ID NO 55
<211> LENGTH: 54
<212> TYPE: DNA
<213> ORGANISM: Artificial Sequence
<220> FEATURE:
<223> OTHER INFORMATION: primer

<400> SEQUENCE: 55
cgcaggcgcg ccccgcggaa ggagatatac catgttagtt ttatccttga ttta     54

<210> SEQ ID NO 56
<211> LENGTH: 41
<212> TYPE: DNA
<213> ORGANISM: Artificial Sequence
<220> FEATURE:
<223> OTHER INFORMATION: primer

<400> SEQUENCE: 56
gcatacgcgt gggcccgtta caacaatctc tcttcgaatc t     41

<210> SEQ ID NO 57
<211> LENGTH: 52
<212> TYPE: DNA
<213> ORGANISM: Artificial Sequence
<220> FEATURE:
<223> OTHER INFORMATION: primer

<400> SEQUENCE: 57
cgcaggcgcg ccgggcccga aggagatata ccatgggaat acacatacca ta     52

<210> SEQ ID NO 58
<211> LENGTH: 36
<212> TYPE: DNA
<213> ORGANISM: Artificial Sequence
<220> FEATURE:
<223> OTHER INFORMATION: primer

<400> SEQUENCE: 58
gcatacgcgt ccgcggccta tatatcctct ataatc     36

<210> SEQ ID NO 59
<211> LENGTH: 30
<212> TYPE: DNA
<213> ORGANISM: Artificial Sequence
<220> FEATURE:
<223> OTHER INFORMATION: primer

<400> SEQUENCE: 59
ggccgtcgac cataatggtc catgggtaca     30

<210> SEQ ID NO 60
<211> LENGTH: 33
<212> TYPE: DNA
<213> ORGANISM: Artificial Sequence
<220> FEATURE:
<223> OTHER INFORMATION: primer

<400> SEQUENCE: 60
aattctcgag ttagtagaag actttctcca ggt                              33

<210> SEQ ID NO 61
<211> LENGTH: 34
<212> TYPE: DNA
<213> ORGANISM: Artificial Sequence
<220> FEATURE:
<223> OTHER INFORMATION: primer

<400> SEQUENCE: 61
gggcccataa tggcggcctc cagtgtcctc ctgc                             34

<210> SEQ ID NO 62
<211> LENGTH: 30
<212> TYPE: DNA
<213> ORGANISM: Artificial Sequence
<220> FEATURE:
<223> OTHER INFORMATION: primer

<400> SEQUENCE: 62
ggccaagctt tagatcagta tgggtcatta                                  30

<210> SEQ ID NO 63
<211> LENGTH: 30
<212> TYPE: DNA
<213> ORGANISM: Artificial Sequence
<220> FEATURE:
<223> OTHER INFORMATION: primer

<400> SEQUENCE: 63
ccggactagt ataatggcca ctggtcgtat                                  30

<210> SEQ ID NO 64
<211> LENGTH: 36
<212> TYPE: DNA
<213> ORGANISM: Artificial Sequence
<220> FEATURE:
<223> OTHER INFORMATION: primer

<400> SEQUENCE: 64
ggcgttaatt aaccctctag attaccagaa aataag                           36

<210> SEQ ID NO 65
<211> LENGTH: 40
<212> TYPE: DNA
<213> ORGANISM: Artificial Sequence
<220> FEATURE:
<223> OTHER INFORMATION: primer

<400> SEQUENCE: 65
cggcactagt ataatggcta agcttccttc tacggctcag                       40

<210> SEQ ID NO 66
<211> LENGTH: 39
<212> TYPE: DNA
<213> ORGANISM: Artificial Sequence
<220> FEATURE:
<223> OTHER INFORMATION: primer

```
<400> SEQUENCE: 66
ggccttaatt aactaatcat agagcttggg acccgaagc                    39

<210> SEQ ID NO 67
<211> LENGTH: 32
<212> TYPE: DNA
<213> ORGANISM: Artificial Sequence
<220> FEATURE:
<223> OTHER INFORMATION: primer

<400> SEQUENCE: 67
ggccactagt ataatggacg ctcccgaagt ca                           32

<210> SEQ ID NO 68
<211> LENGTH: 36
<212> TYPE: DNA
<213> ORGANISM: Artificial Sequence
<220> FEATURE:
<223> OTHER INFORMATION: primer

<400> SEQUENCE: 68
ggccttaatt aatagactac cactgcacct cctcag                       36

<210> SEQ ID NO 69
<211> LENGTH: 34
<212> TYPE: DNA
<213> ORGANISM: Artificial Sequence
<220> FEATURE:
<223> OTHER INFORMATION: primer

<400> SEQUENCE: 69
aatctctaga atgaaggtga cggtgggccc agac                         34

<210> SEQ ID NO 70
<211> LENGTH: 28
<212> TYPE: DNA
<213> ORGANISM: Artificial Sequence
<220> FEATURE:
<223> OTHER INFORMATION: primer

<400> SEQUENCE: 70
ctatggtacc tcaccagctc aggatgcc                                28

<210> SEQ ID NO 71
<211> LENGTH: 39
<212> TYPE: DNA
<213> ORGANISM: Artificial Sequence
<220> FEATURE:
<223> OTHER INFORMATION: primer

<400> SEQUENCE: 71
gcgattccat atgtctgtga tcacggaaca aaacacgta                    39

<210> SEQ ID NO 72
<211> LENGTH: 40
<212> TYPE: DNA
<213> ORGANISM: Artificial Sequence
<220> FEATURE:
<223> OTHER INFORMATION: primer

<400> SEQUENCE: 72
gcgcggatcc aggcttaatt aagcttagac aggcaacgat                   40
```